(12) United States Patent
van der Burg et al.

(10) Patent No.: US 10,966,710 B2
(45) Date of Patent: *Apr. 6, 2021

(54) SUTURE PASSER SYSTEMS AND METHODS FOR TONGUE OR OTHER TISSUE SUSPENSION AND COMPRESSION

(71) Applicant: Siesta Medical, Inc., Los Gatos, CA (US)

(72) Inventors: Erik van der Burg, Los Gatos, CA (US); Peter Martin, Mountain View, CA (US); Chris Feezor, San Jose, CA (US); Mark Hirotsuka, San Jose, CA (US); Jasper Jackson, Newark, CA (US); Christopher T. Cheng, Los Altos, CA (US); Michael Kolber, Los Gatos, CA (US); Adam H. Liston, Davis, CA (US)

(73) Assignee: Siesta Medical, Inc., Los Gatos, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/213,079

(22) Filed: Dec. 7, 2018

(65) Prior Publication Data

US 2019/0175169 A1 Jun. 13, 2019

Related U.S. Application Data

(63) Continuation of application No. 15/201,234, filed on Jul. 1, 2016, now Pat. No. 10,182,810, which is a (Continued)

(51) Int. Cl.
*A61B 17/04* (2006.01)
*A61B 17/00* (2006.01)
(Continued)

(52) U.S. Cl.
CPC ...... *A61B 17/0483* (2013.01); *A61B 17/0401* (2013.01); *A61B 17/0469* (2013.01); (Continued)

(58) Field of Classification Search
CPC ............ A61B 17/0401; A61B 17/0483; A61B 17/0469; A61B 17/0485; A61B 17/0487; (Continued)

(56) References Cited

U.S. PATENT DOCUMENTS 2,143,910 A 1/1939 Didusch
2,167,251 A 7/1939 Rogers
(Continued)

FOREIGN PATENT DOCUMENTS

RU 108286 9/2011
WO WO 1999/003402 1/1999
(Continued)

OTHER PUBLICATIONS

U.S. Appl. No. 16/128,816, filed Sep. 12, 2018, Feezor et al.
(Continued)

*Primary Examiner* — Julian W Woo
(74) *Attorney, Agent, or Firm* — Knobbe, Martens, Olson & Bear, LLP

(57) ABSTRACT

Suture passer systems for tissue suspension and tissue compression, and more particularly for tongue suspension, are described. The system can include at least a first elongate tubular body or shaft, a needle having a lateral bias carried by the elongate body, and a retrieval element operably connected to the elongate tubular body. The needle can have a substantially straight configuration when located within the elongate tubular body, and be configured to exit an opening at or near a distal end of the elongate tubular body and assume a laterally biased or curved shape to form a path through tissue. The needle is configured to carry a suture.

(Continued)

The retrieval element can be configured to retrieve the suture carried by the needle after the needle has formed a curved or otherwise angled path through tissue. The system can also include one or more bone anchors to secure the suture loops. Methods of placing one or more suture loops into tissue, such as the base of the tongue, are also described.

20 Claims, 67 Drawing Sheets

Related U.S. Application Data continuation of application No. 13/913,123, filed on Jun. 7, 2013, now Pat. No. 9,386,981, which is a continuation of application No. 13/077,813, filed on Mar. 31, 2011, now Pat. No. 8,460,322.

(60) Provisional application No. 61/319,822, filed on Mar. 31, 2010, provisional application No. 61/363,618, filed on Jul. 12, 2010, provisional application No. 61/435,230, filed on Jan. 21, 2011.

(51) Int. Cl.
A61B 17/06 (2006.01)
A61B 90/00 (2016.01)
A61B 90/30 (2016.01)
A61B 17/24 (2006.01)

(52) U.S. Cl.
CPC .......... *A61B 17/0485* (2013.01); *A61B 90/39* (2016.02); *A61B 17/0487* (2013.01); *A61B 2017/00814* (2013.01); *A61B 2017/044* (2013.01); *A61B 2017/0414* (2013.01); *A61B 2017/0448* (2013.01); *A61B 2017/0454* (2013.01); *A61B 2017/0461* (2013.01); *A61B 2017/0472* (2013.01); *A61B 2017/06052* (2013.01); *A61B 2017/248* (2013.01); *A61B 2090/309* (2016.02); *A61B 2090/3966* (2016.02)

(58) Field of Classification Search
CPC .......... A61B 19/54; A61B 2017/00814; A61B 2017/0414; A61B 2017/044; A61B 2017/0448; A61B 2017/0454; A61B 2017/0461; A61B 2017/0472; A61B 2017/06052; A61B 2017/248; A61B 2019/521

See application file for complete search history.

(56) References Cited

U.S. PATENT DOCUMENTS

| | | |
|---|---|---|
| 3,194,239 A | 7/1965 | Sullivan |
| 3,570,497 A | 3/1971 | Lemole |
| 3,709,373 A | 1/1973 | Aguilar |
| 4,034,763 A | 7/1977 | Frazier |
| 4,185,626 A | 1/1980 | Jones et al. |
| 4,372,293 A | 2/1983 | Vijil-Rosales |
| 4,441,497 A | 4/1984 | Paudler |
| 4,557,264 A | 12/1985 | Hinsch |
| 4,792,336 A | 12/1988 | Hlavacek et al. |
| 4,959,069 A | 9/1990 | Brenann et al. |
| 5,250,055 A | 10/1993 | Moore et al. |
| 5,330,488 A | 7/1994 | Goldrath |
| 5,336,231 A | 8/1994 | Adair |
| 5,337,736 A | 8/1994 | Reddy |
| 5,364,407 A | 11/1994 | Poll |
| 5,391,174 A | 2/1995 | Weston |
| 5,411,523 A | 5/1995 | Goble |
| 5,443,482 A | 8/1995 | Stone et al. |
| 5,501,691 A | 3/1996 | Goldrath |
| 5,534,011 A | 7/1996 | Greene, Jr. et al. |
| 5,620,012 A | 4/1997 | Benderev |
| 5,672,316 A | 9/1997 | Knapp |
| 5,692,520 A | 12/1997 | Lavoisier |
| 5,692,530 A | 12/1997 | Bible et al. |
| 5,722,981 A | 3/1998 | Stevens |
| 5,868,789 A | 2/1999 | Huebner |
| 5,895,395 A | 4/1999 | Yeung |
| 5,906,624 A | 5/1999 | Wenstrom, Jr. |
| 5,980,559 A | 11/1999 | Bonutti |
| 5,988,171 A | 11/1999 | Sohn |
| 6,096,051 A | 8/2000 | Kortenbach et al. |
| 6,161,541 A | 12/2000 | Woodson |
| 6,258,106 B1 | 7/2001 | Leonard |
| 6,264,677 B1 | 7/2001 | Simon et al. |
| 6,273,852 B1 | 8/2001 | Lehe et al. |
| 6,368,326 B1 | 4/2002 | Dakin |
| 6,554,845 B1 | 4/2003 | Fleenor et al. |
| 6,610,080 B2 | 8/2003 | Morgan |
| 6,638,283 B2 | 10/2003 | Thal |
| 6,638,286 B1 | 10/2003 | Burbank |
| 6,660,023 B2 | 12/2003 | McDevitt et al. |
| 6,672,316 B1 | 1/2004 | Weihrauch |
| 6,746,456 B2 | 6/2004 | Xiao |
| 6,786,913 B1 | 9/2004 | Sancoff et al. |
| 6,984,237 B2 | 1/2006 | Hatch et al. |
| 6,991,636 B2 | 1/2006 | Rose |
| 7,081,126 B2 | 7/2006 | McDevitt et al. |
| 7,090,672 B2 | 8/2006 | Underwood et al. |
| 7,213,599 B2 | 5/2007 | Conrad et al. |
| 7,232,448 B2 | 6/2007 | Battles |
| 7,237,554 B2 | 7/2007 | Conrad et al. |
| 7,306,613 B2 | 12/2007 | Kawashima et al. |
| 7,337,781 B2 | 3/2008 | Vassallo |
| 7,367,340 B2 | 5/2008 | Nelson et al. |
| 7,401,611 B2 | 7/2008 | Conrad et al. |
| 7,625,386 B2 | 12/2009 | Abe et al. |
| 7,673,635 B2 | 3/2010 | Conrad et al. |
| 7,674,276 B2 | 3/2010 | Stone et al. |
| 7,703,460 B2 | 4/2010 | Conrad et al. |
| 7,867,251 B2 | 1/2011 | Colleran et al. |
| 7,892,256 B2 | 2/2011 | Grafton |
| 7,918,868 B2 | 4/2011 | Marshall et al. |
| 8,038,712 B2 | 10/2011 | van der Burg et al. |
| 8,096,303 B2 | 1/2012 | Dineen et al. |
| 8,167,787 B2 | 5/2012 | Gillis |
| 8,177,795 B2 | 5/2012 | Niese et al. |
| 8,186,355 B2 | 5/2012 | van der Burg et al. |
| 8,236,027 B2 | 8/2012 | Wu |
| 8,460,322 B2 | 6/2013 | van der Burg et al. |
| 8,561,616 B2 | 10/2013 | Rousseau et al. |
| 8,561,617 B2 * | 10/2013 | Lindh ................. A61F 5/566 128/848 |
| 8,821,495 B2 | 9/2014 | van der Burg et al. |
| 8,911,347 B2 | 12/2014 | Browning |
| 9,386,981 B2 | 7/2016 | van der Burg et al. |
| 9,463,014 B2 | 10/2016 | Feezor et al. |
| 9,877,862 B2 * | 1/2018 | Weadock ............. A61F 5/566 |
| 10,182,810 B2 * | 1/2019 | Van der Burg .... A61B 17/0469 |
| 2003/0149447 A1 | 8/2003 | Morency et al. |
| 2004/0134491 A1 | 7/2004 | Pflueger et al. |
| 2005/0119696 A1 | 6/2005 | Walters et al. |
| 2005/0126563 A1 | 6/2005 | van der Burg et al. |
| 2005/0149122 A1 | 7/2005 | McDevitt et al. |
| 2005/0192631 A1 | 9/2005 | Grafton |
| 2005/0245932 A1 | 11/2005 | Fanton |
| 2005/0288690 A1 | 12/2005 | Bourque et al. |
| 2006/0070626 A1 | 4/2006 | Frazier et al. |
| 2006/0106423 A1 | 5/2006 | Weisel et al. |
| 2006/0150986 A1 | 7/2006 | Roue et al. |
| 2006/0201519 A1 | 9/2006 | Frazier et al. |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0271060 A1 | 11/2006 | Gordon |
| 2006/0276817 A1 | 12/2006 | Vassallo et al. |

(56) References Cited

U.S. PATENT DOCUMENTS

| | | |
|---|---|---|
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2006/0282088 A1 | 12/2006 | Ryan |
| 2007/0144539 A1 | 6/2007 | Van Der Burg et al. |
| 2007/0149986 A1 | 6/2007 | Morris et al. |
| 2007/0149987 A1 | 6/2007 | Wellman et al. |
| 2007/0179509 A1 | 8/2007 | Nagata et al. |
| 2007/0179529 A1 | 8/2007 | Doyle |
| 2007/0213770 A1 | 9/2007 | Dreyfuss |
| 2007/0225763 A1 | 9/2007 | Zwolinski et al. |
| 2007/0261701 A1 | 11/2007 | Sanders |
| 2007/0288057 A1 | 12/2007 | Kuhnel |
| 2008/0023012 A1 | 1/2008 | Dineen et al. |
| 2008/0027273 A1 | 1/2008 | Gutternman |
| 2008/0027480 A1 | 1/2008 | Van Der Burg et al. |
| 2008/0027560 A1 | 1/2008 | Jackson et al. |
| 2008/0035160 A1 | 2/2008 | Woodson et al. |
| 2008/0053461 A1 | 3/2008 | Hirotsuka et al. |
| 2008/0058584 A1 | 3/2008 | Hirotsuka et al. |
| 2008/0066766 A1 | 3/2008 | Paraschac et al. |
| 2008/0066767 A1 | 3/2008 | Paraschac et al. |
| 2008/0066769 A1 | 3/2008 | Dineen et al. |
| 2008/0077162 A1 | 3/2008 | Domingo |
| 2008/0082113 A1 | 4/2008 | Bishop et al. |
| 2008/0091219 A1 | 4/2008 | Marshall et al. |
| 2008/0103506 A1 | 5/2008 | Volpi et al. |
| 2008/0154286 A1 | 6/2008 | Abbott et al. |
| 2008/0208265 A1 | 8/2008 | Frazier et al. |
| 2008/0275469 A1 | 11/2008 | Fanton et al. |
| 2009/0014012 A1 | 1/2009 | Sanders |
| 2009/0018554 A1 | 1/2009 | Thorne et al. |
| 2009/0026236 A1 | 1/2009 | Krause |
| 2009/0069824 A1 | 3/2009 | Chu |
| 2009/0099598 A1 | 4/2009 | McDevitt et al. |
| 2009/0105751 A1 | 4/2009 | Zentgraf |
| 2009/0105753 A1 | 4/2009 | Greenhalgh et al. |
| 2009/0125043 A1 | 5/2009 | Dehnad |
| 2009/0210005 A1 | 8/2009 | Dinger |
| 2009/0228041 A1 | 9/2009 | Domingo |
| 2009/0248071 A1 | 10/2009 | Saint et al. |
| 2009/0318938 A1 | 12/2009 | Hathaway et al. |
| 2009/0318958 A1 | 12/2009 | Ochiai |
| 2009/0319046 A1 | 12/2009 | Krespi |
| 2010/0004683 A1 | 1/2010 | Hoof et al. |
| 2010/0106169 A1 | 4/2010 | Niese et al. |
| 2010/0114123 A1 | 5/2010 | Nason |
| 2010/0132719 A1 | 6/2010 | Jacobs et al. |
| 2010/0160962 A1 | 6/2010 | Dreyfuss et al. |
| 2010/0198235 A1 | 8/2010 | Pierce et al. |
| 2010/0262184 A1 | 10/2010 | Dreyfuss |
| 2011/0004242 A1 | 1/2011 | Stchur |
| 2011/0155142 A1 | 6/2011 | Boucher |
| 2011/0230974 A1 | 9/2011 | Musani |
| 2011/0245850 A1 | 10/2011 | van der Burg et al. |
| 2011/0308529 A1 | 12/2011 | Gillis et al. |
| 2012/0017919 A1 | 1/2012 | Gillis et al. |
| 2012/0132214 A1 | 5/2012 | Gillis et al. |
| 2012/0277767 A1 | 11/2012 | Powers et al. |
| 2013/0233324 A1 | 9/2013 | Witt et al. |
| 2013/0345724 A1 | 12/2013 | van der Burg et al. |
| 2014/0074158 A1 | 3/2014 | Feezor et al. |
| 2015/0250476 A1 | 9/2015 | Feezor et al. |
| 2017/0000477 A1 | 1/2017 | van der Burg et al. |
| 2017/0020506 A1 | 1/2017 | Feezor et al. |
| 2019/0167264 A1 | 6/2019 | Feezor et al. |
| 2019/0175169 A1 | 6/2019 | van der Burg et al. |
| 2020/0078194 A1 | 3/2020 | Feezor et al. |

FOREIGN PATENT DOCUMENTS

| | | |
|---|---|---|
| WO | WO 2002/039905 | 5/2002 |
| WO | WO 2007/073931 | 7/2007 |
| WO | WO 2011/123714 | 10/2011 |
| WO | WO 2011/151745 | 12/2011 |
| WO | WO 2014/039848 | 3/2014 |
| WO | WO 2015/134763 | 9/2015 |

OTHER PUBLICATIONS

Abraham Lapidot, M.D. and Nahum Ben-Hur, M.D., Fastening the Base of the Tongue Forward to the Hyoid for Relief of Respiratory Distress in Pierre Robin Syndrome, 56 Plastic & Reconstructive Surgery 89 in 4 pages (1975).

Beverly Douglas, M.D., The Treatment of Micrognathia Associated with Obstruction by a Plastic Procedure, in 1 Plastic & Reconstructive Surgery 300, in 12 pages (Warren B. Davis ed., The Williams & Wilkins Co. 1946).

Chris T. Oeconomopoulos, M.D., The Value of Glossopexy in Pierre-Robin Syndrome, 262 NEJM 1267 in 3 pages (1960).

Frank G. DeLuca, M.D., and Conrad W. Wesselhoeft, M.D., Surgically Treatable Causes of Neonatal Respiratory Distress, 5 Clinics in Perinatology 377 in 19 pages (1978).

H. Faye-Lund, G. Djupesland, & T. Lyberg, Glossopexia—Evaluation of a New Surgical Method for Treating Obstructive Sleep Apnea Syndrome, 492 Acta Oto-Laryngologica 46 in 4 pages (1990).

M.R. Wexler, H. Kaplan, K. Abu-Dalu, & M. Rousso, A Dynamic Fixation of the Base of the Tongue to the Mandible Using De-epithelized Tongue Flap in the Pierre Robin Syndrome, 4 Chirurgia Plastica 297 in 5 pages (1979).

Peter Randall, M.D., The Robin Anomalad: Micrognathia and Glossoptosis with Airway Obstruction, Reconstructive Plastic Surgery 2241 in 13 pages (2d ed., W.B. Saunders Co. 1977).

Robert M. Woolf, M.D., Nicholas Georgiade, M.D., and Kenneth L. Pickrell, M.D., Micrognathia and Associated Cleft Palate, 26 Plastic & Reconstructive Surgery 199 in 4 pages (1960).

Robert W. Riley, DDS, MD, Nelson B. Powell, MD and Christian Guilleminault, MD, Obstructive Sleep Apnea and the Hyoid: A Revised Surgical Procedure, 111 Otolaryngol Head Neck Surgery 717 in 5 pages (1994).

Stephen R. Lewis, M.D., John B. Lynch, M.D., & Truman G. Blocker, Jr., M.D., Fascial Slings for Tongue Stabilization in the Pierre Robin Syndrome, 42 Plastic & Reconstructive Surgery 237 in 6 pages (1968).

International Search Report dated Jun. 10, 2011 in International Patent Application No. PCT/US2011/030829 in 16 pages.

International Search Report dated Dec. 12, 2013 in International Patent Application No. PCT/US2013/058547 in 7 pages.

International Search Report/Written Opinion for application No. PCT/US2015/018944 dated Jun. 10, 2015 in 10 pages.

Search Report dated Apr. 28, 2015 in EP Patent Application No. 11763477.4 in 2 pages.

\* cited by examiner

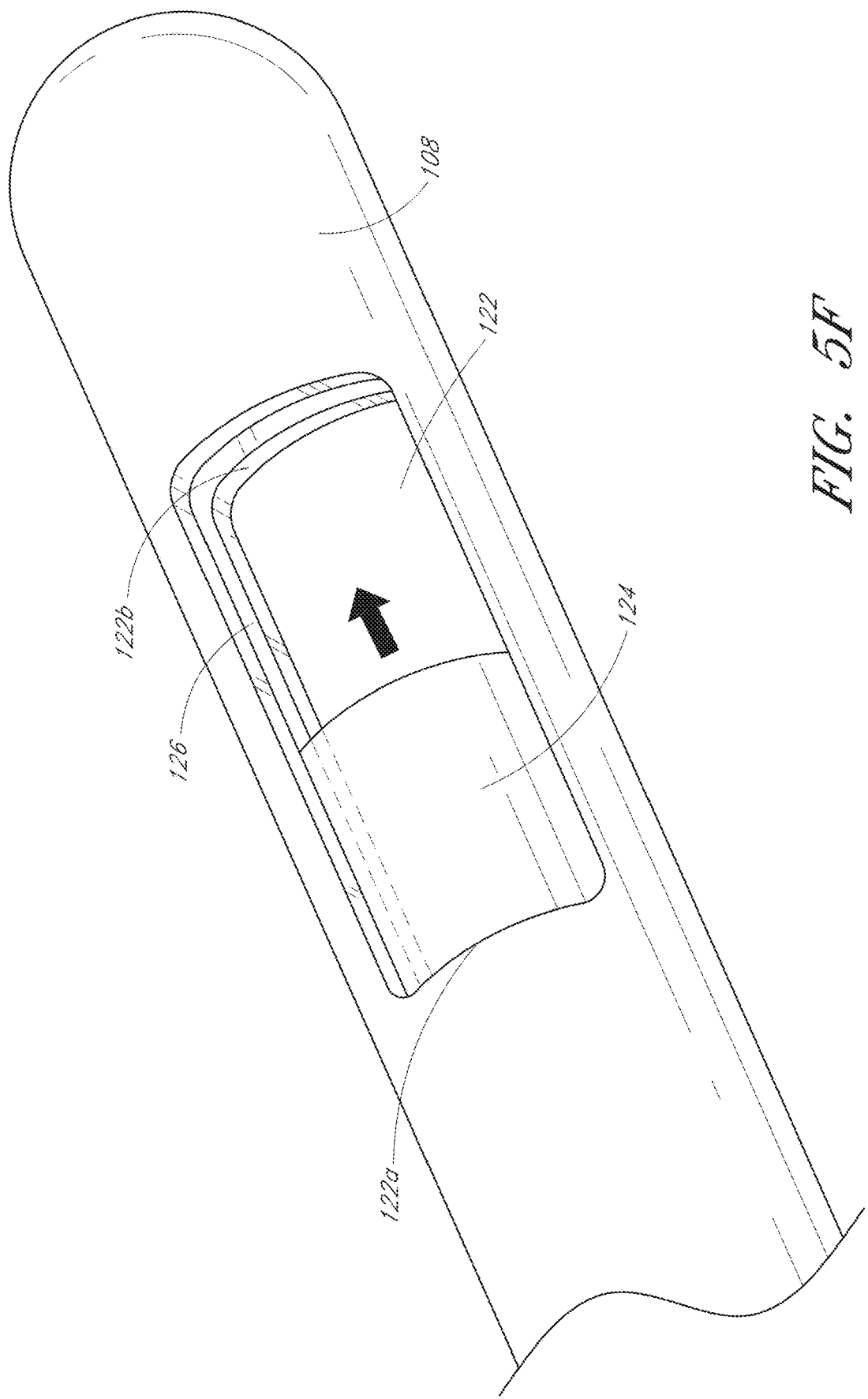

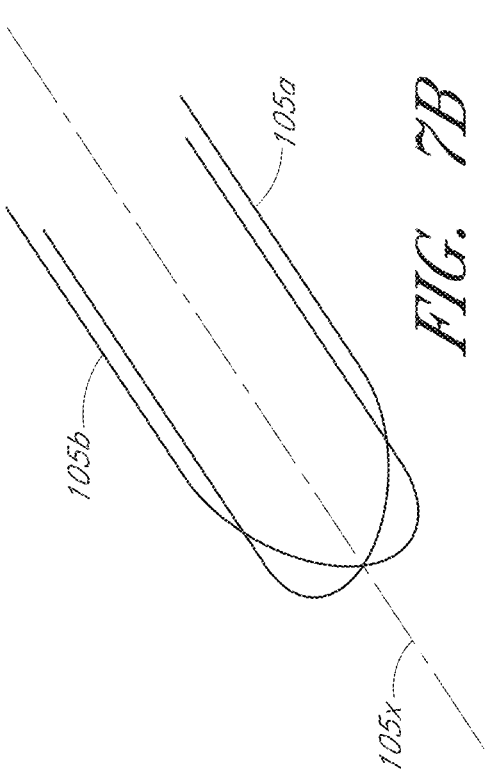
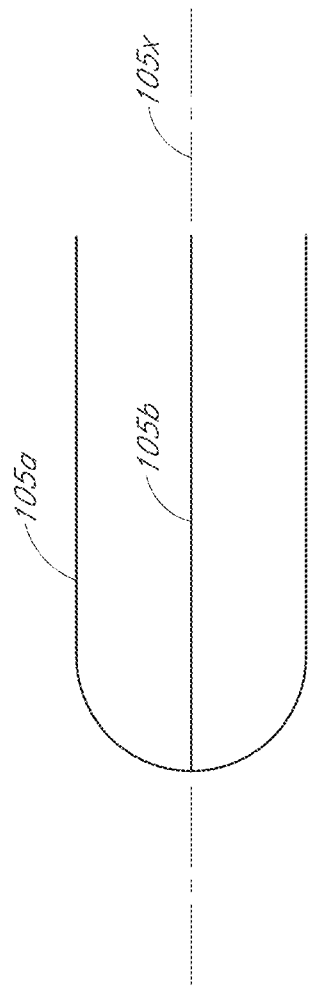
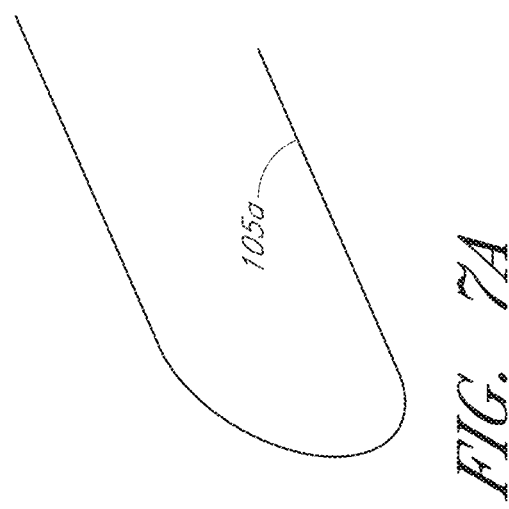
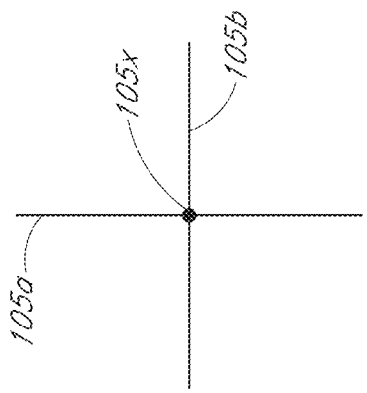
FIG. 7B
FIG. 7D
FIG. 7A
FIG. 7C

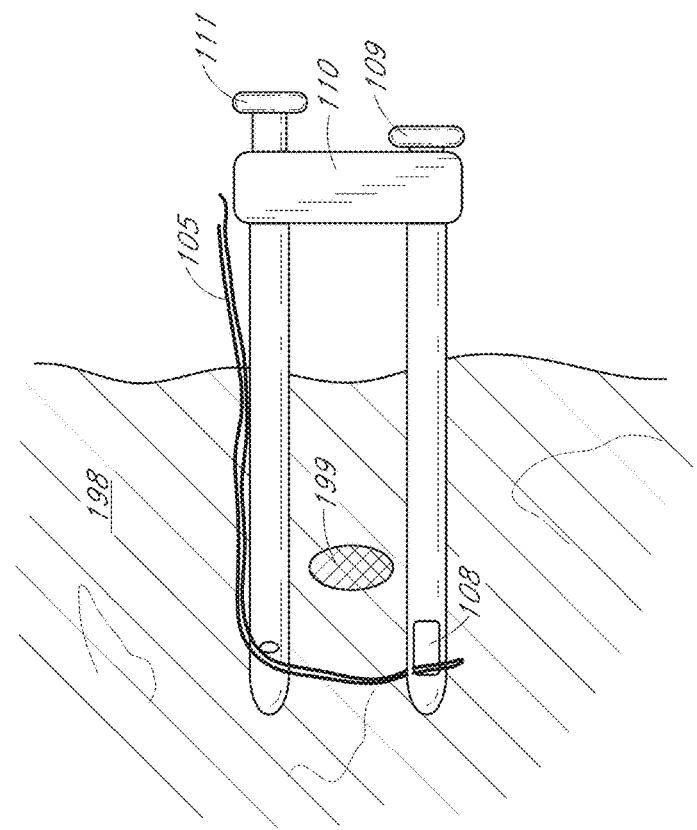
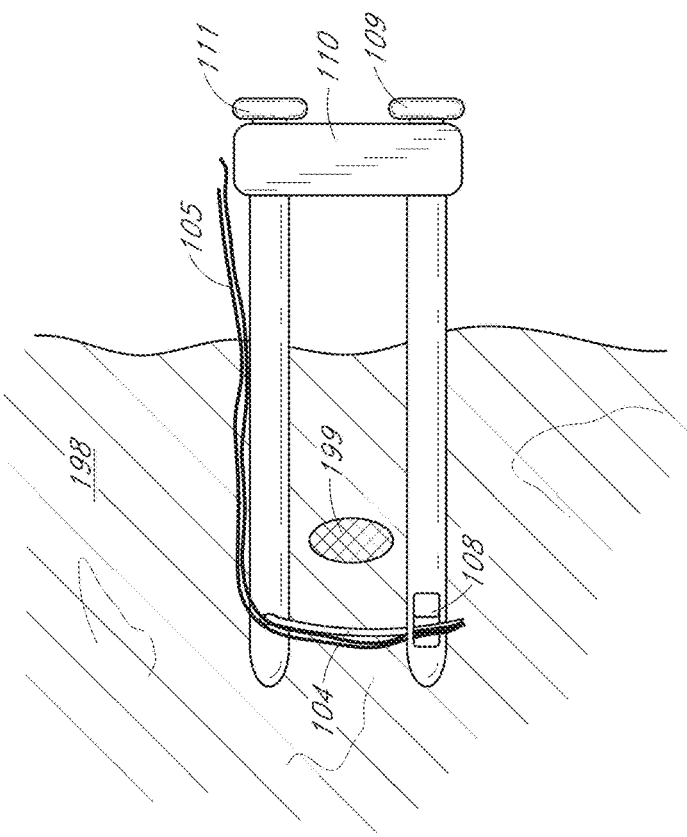

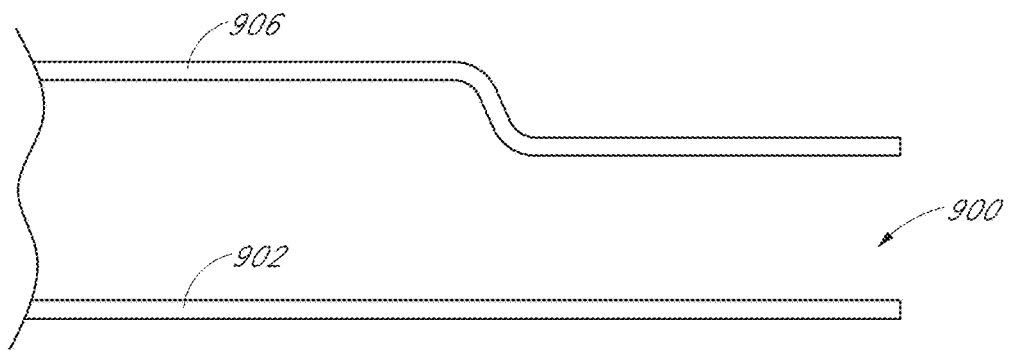
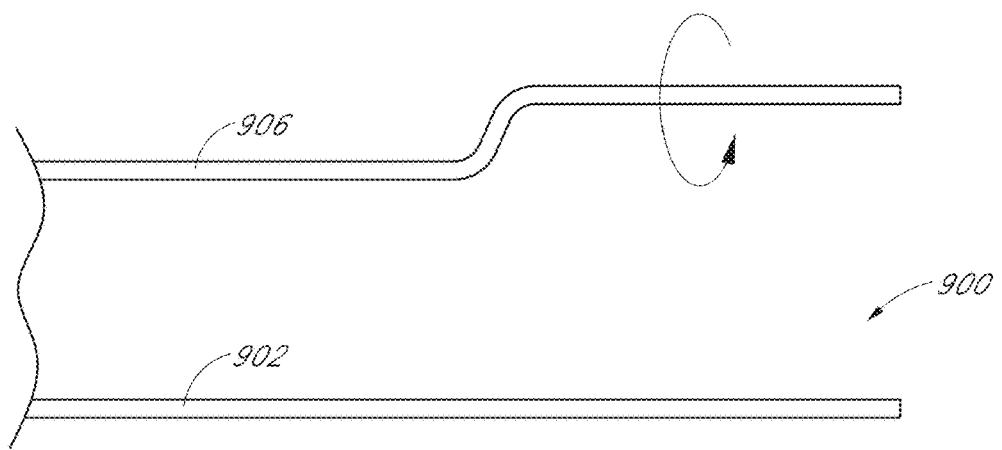
FIG. 9A
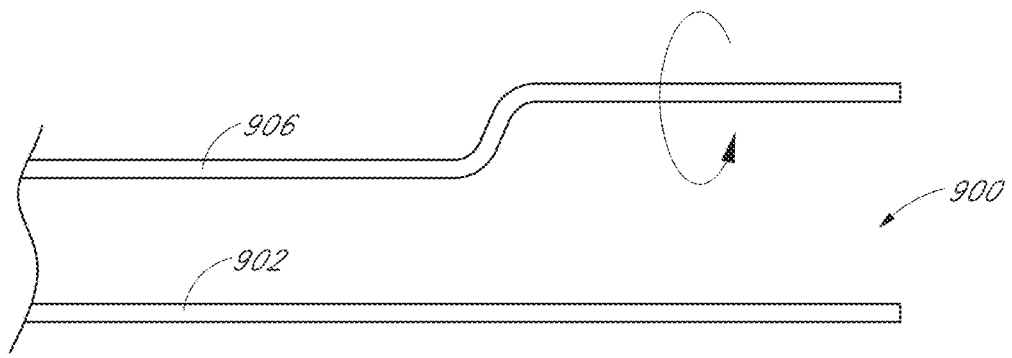
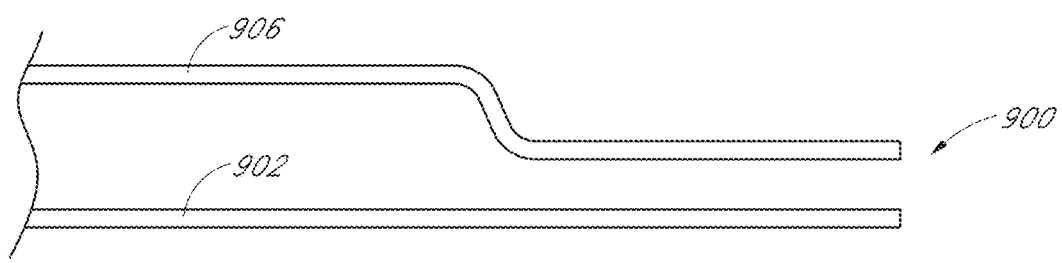
FIG. 9B

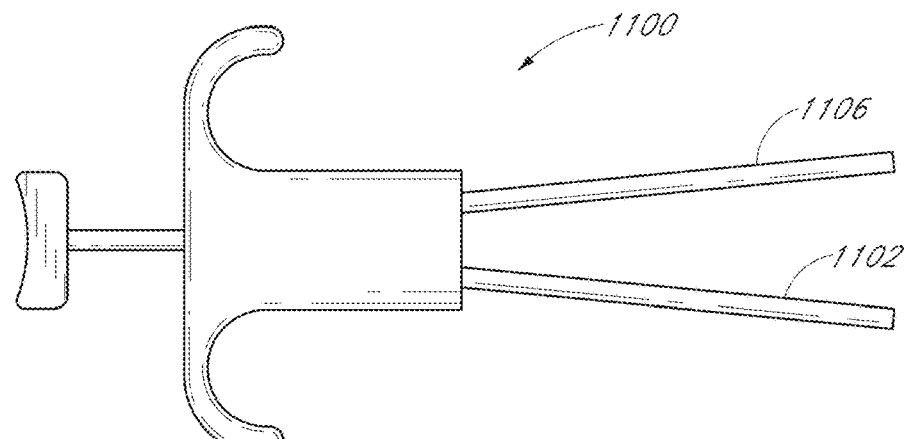
FIG. 11A
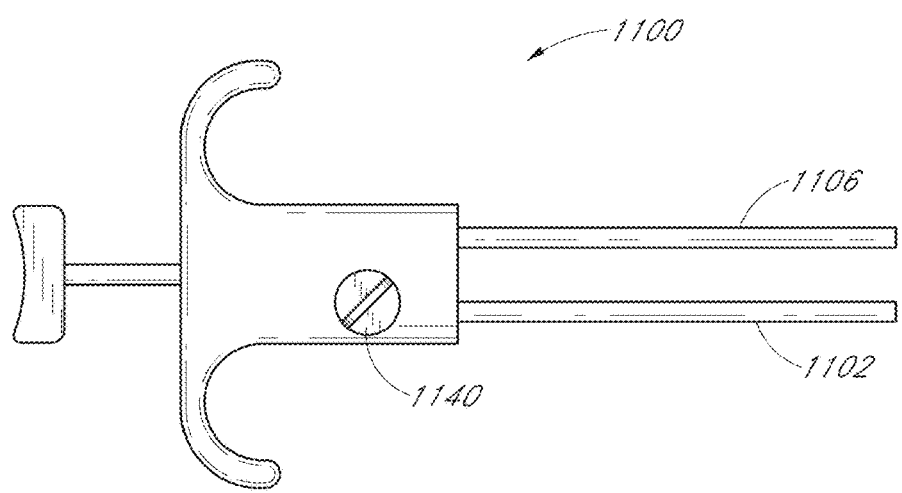
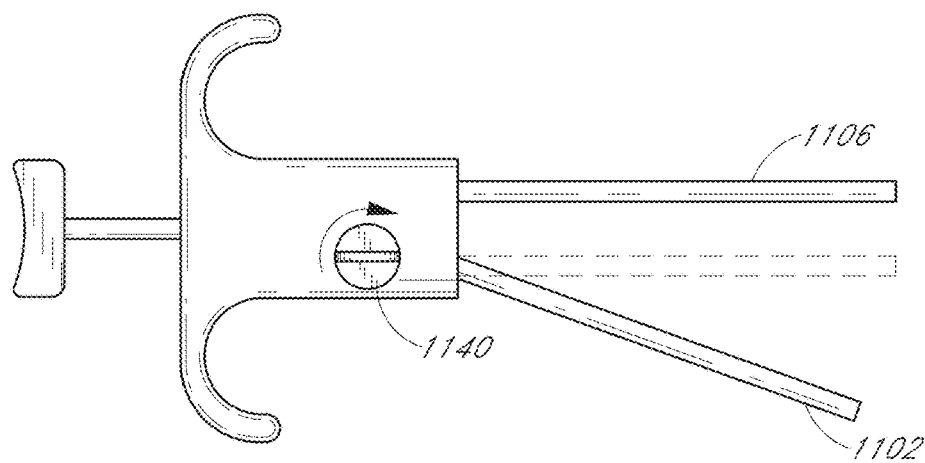
FIG. 11B

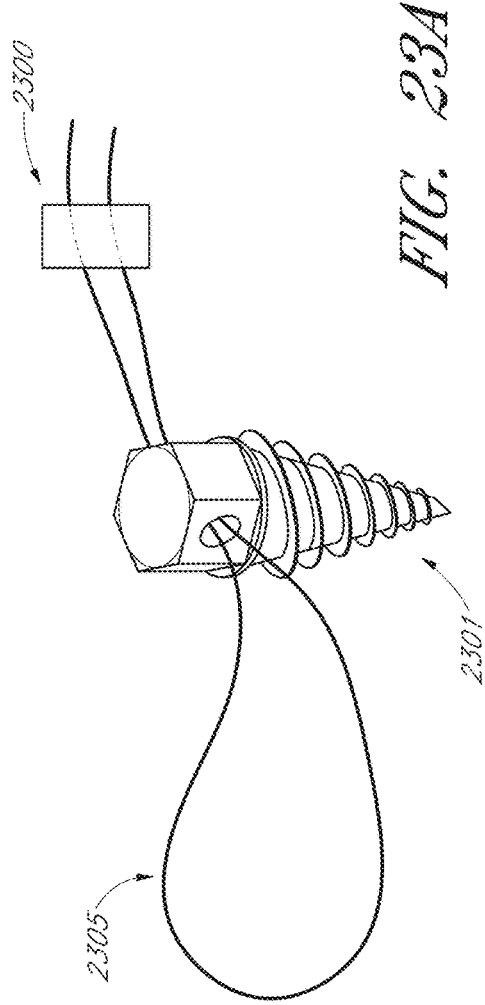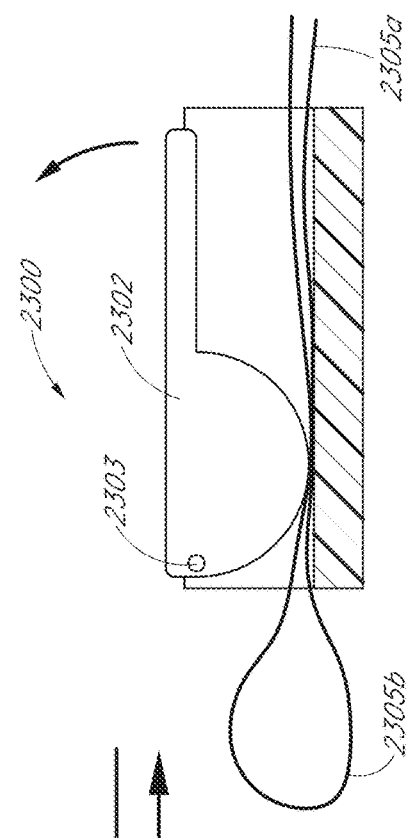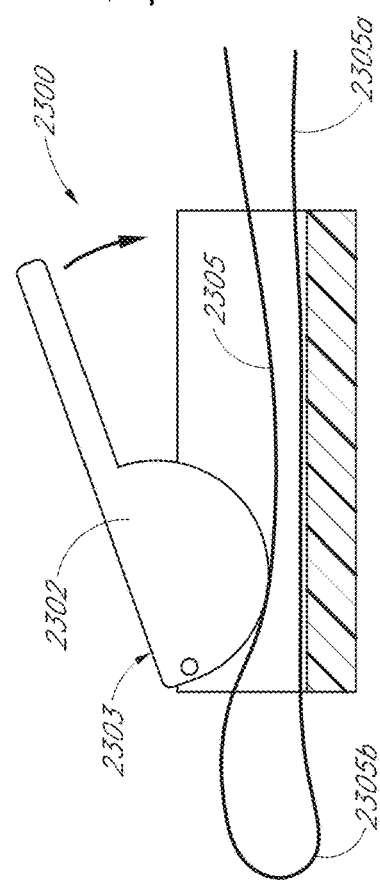
FIG. 23A
FIG. 23B

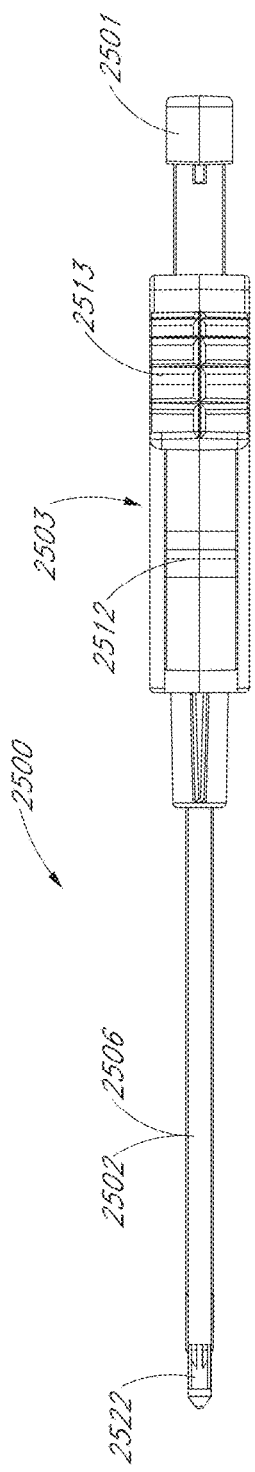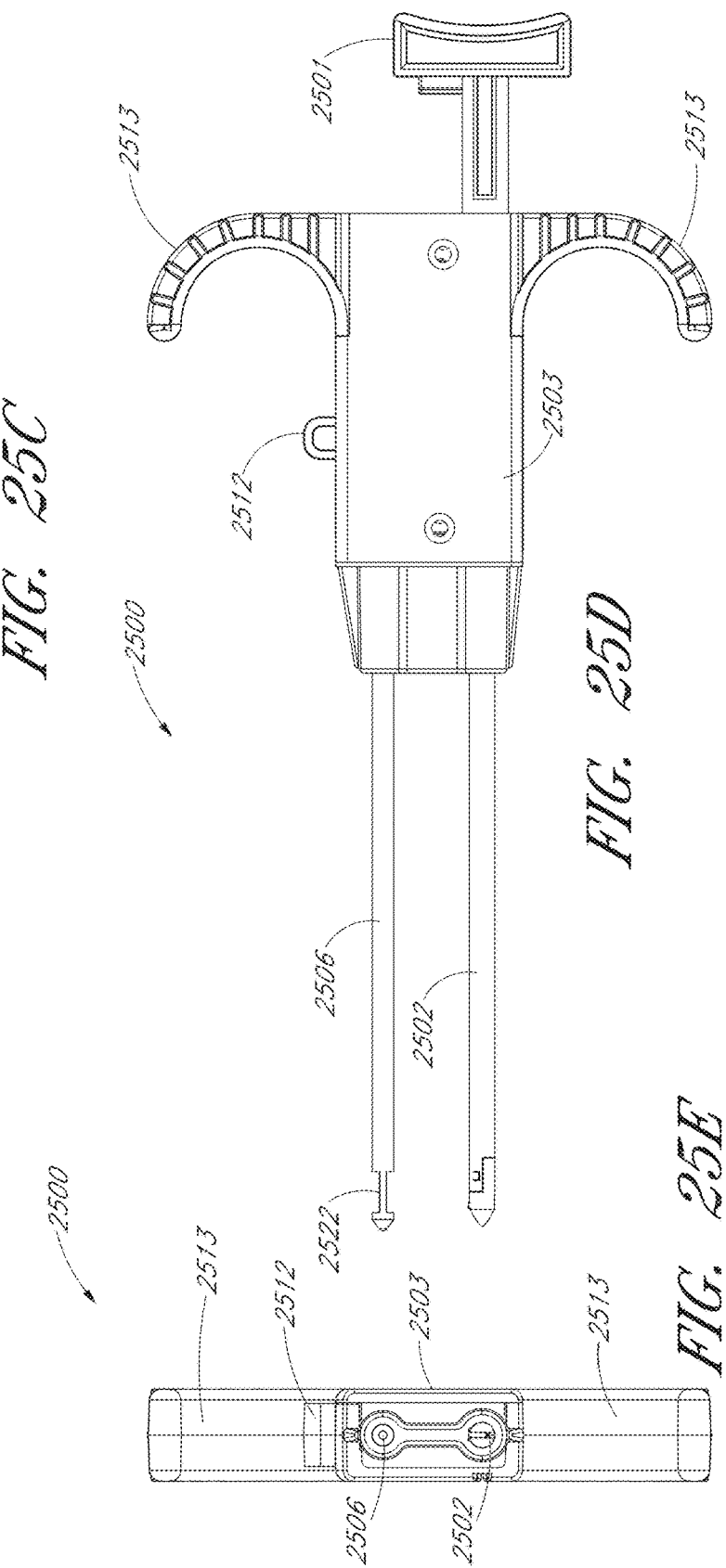

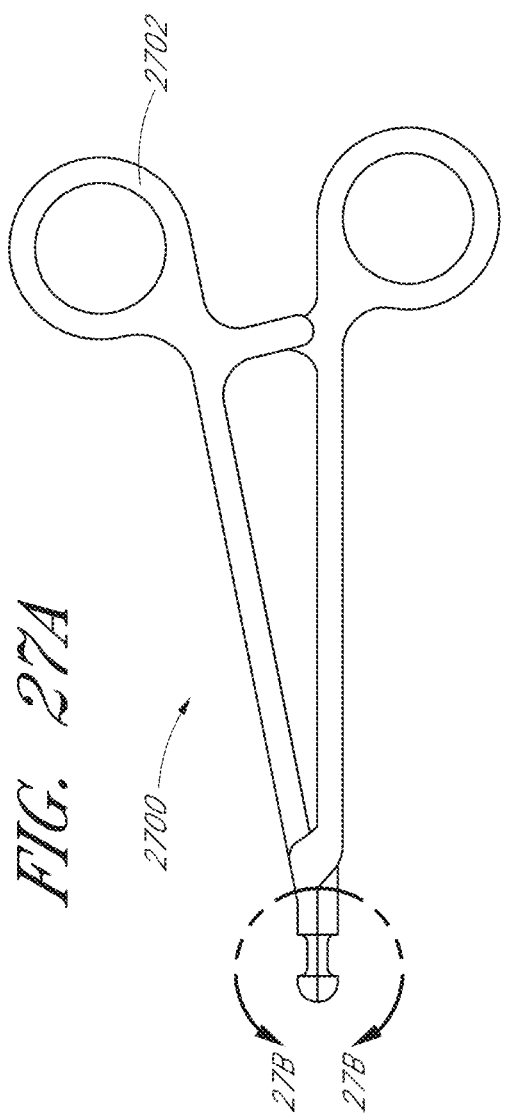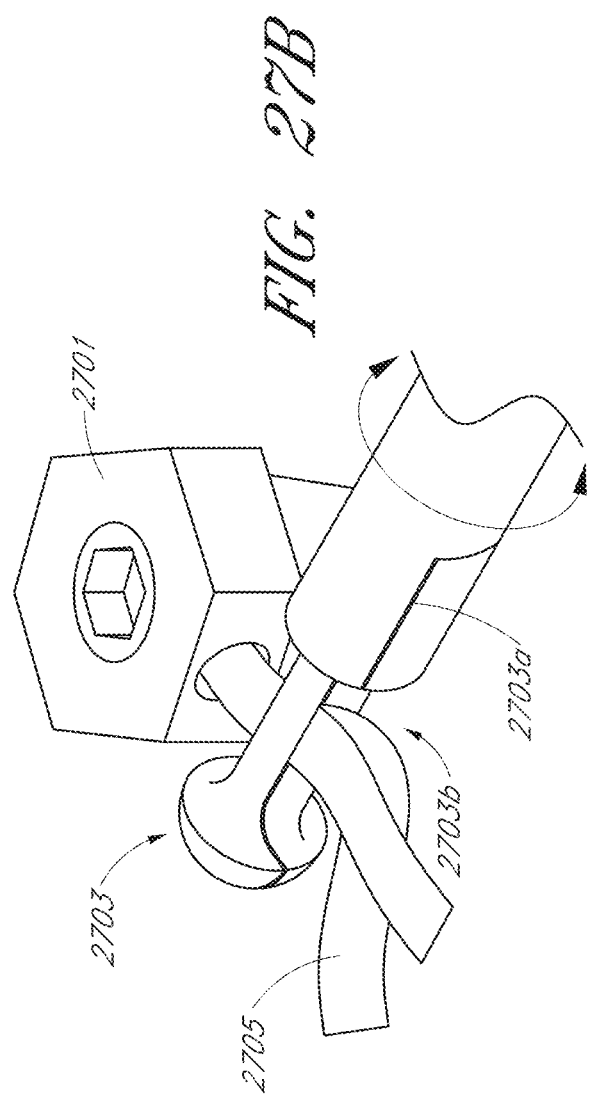

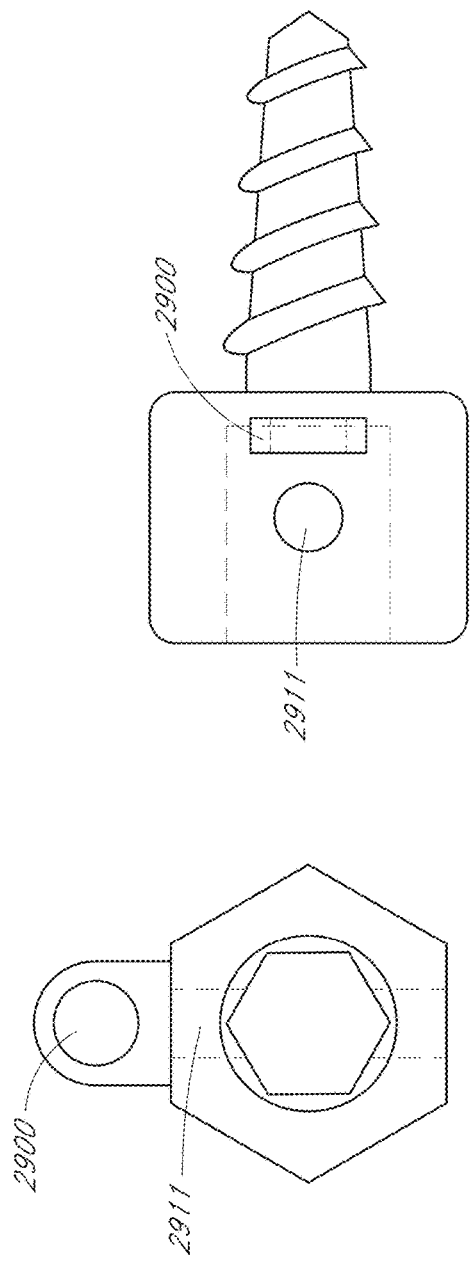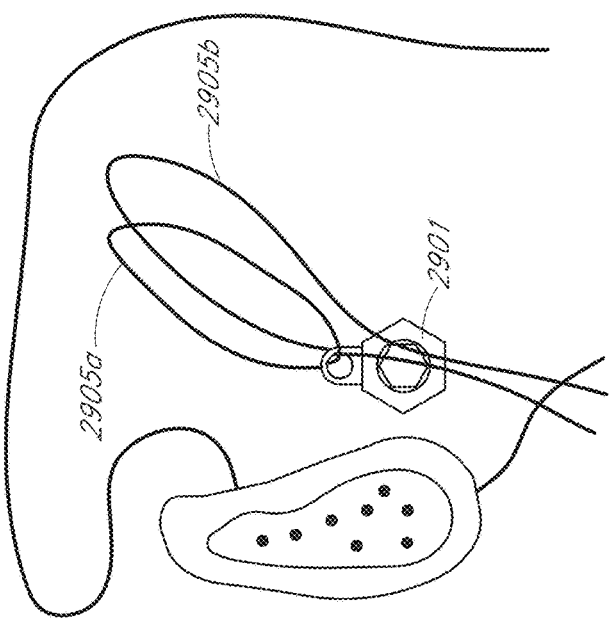
FIG. 29A  FIG. 29B  FIG. 29C

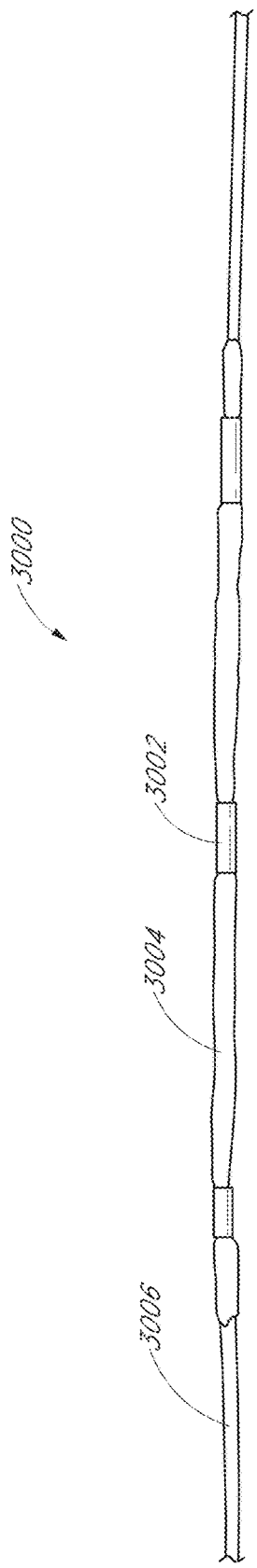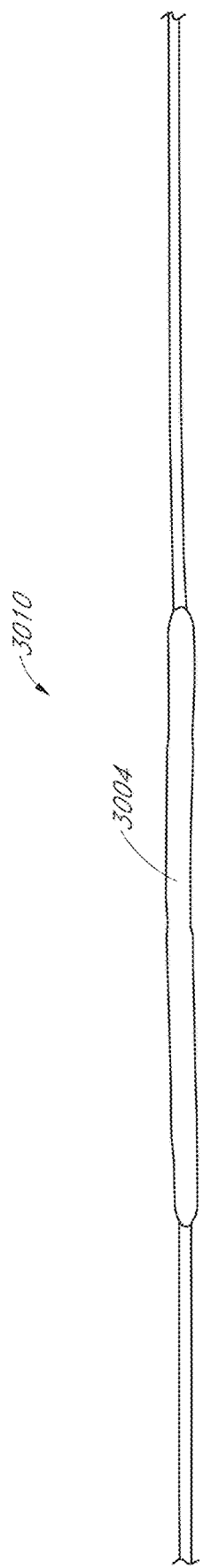

SUTURE PASSER SYSTEMS AND METHODS FOR TONGUE OR OTHER TISSUE SUSPENSION AND COMPRESSION

PRIORITY CLAIM

This application is a continuation of U.S. patent application Ser. No. 15/201,234 filed on Jul. 1, 2016, now issued as U.S. Pat. No. 10,182,810, which is a continuation of U.S. patent application Ser. No. 13/913,123 filed on Jun. 7, 2013, now issued as U.S. Pat. No. 9,386,981, which is a continuation of U.S. patent application Ser. No. 13/077,813 filed Mar. 31, 2011, now issued as U.S. Pat. No. 8,460,322, which in turn claims the benefit under 35 U.S.C, § 119(e) of U.S. Provisional Pat. App. No. 61/319,822 filed on Mar. 31, 2010, U.S. Provisional Pat. App. No. 61/363,618 filed on Jul. 12, 2010, and U.S. Provisional Pat. App. No. 61/435,230 filed on Jan. 21, 2011. Each of the aforementioned priority applications are hereby expressly incorporated by reference in their entireties.

BACKGROUND OF THE INVENTION

Field of the Invention

This invention relates generally to suture passer systems and methods for tissue suspension and tissue compression. In one embodiment this invention relates to systems and methods for tongue suspension using a suture passer and bone anchor for treating obstructive sleep apnea.

Description of the Related Art

In many surgical procedures, there is a need to pass a suture deep into tissue. Sometimes, a surgeon needs to pass a suture deep into tissue to suspend the tissue by fixing the suture to bone. In particular, one such surgical procedure is suspension of the genioglossus muscle of the tongue for treating conditions such as obstructive sleep apnea (OSA). Currently, however, surgeons pass suture needles all the way through the tongue, from anterior to posterior. As a result, the suture may be exposed to a non-sterile environment by virtue of organisms resident in the oral cavity. Furthermore, the surgeon may have greater difficulty locating anterior-to-posterior positions to pass the suture through. This conventional technique also limits the position that the surgeon can place the suture to one that can be reached from the oral cavity.

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velo-pharyngeal insufficiency where food and liquids enter into the nasopharynx during swallowing.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Another surgical procedure performed to treat OSA is suture based tongue suspension. However, current techniques for suture based tongue suspension require the passage of suture through the tongue and into the oral space. This technique carries with it significant risks of infection as well as difficulty in accessing the optimal placement for the suspension suture.

Notwithstanding the foregoing, there remains a need for improved methods and devices for treating various conditions, including but not limited to obstructive sleep apnea. There is also a need for improved devices and methods for delivering suture into tissue. Specifically with respect to current methods for tongue suspension, there is a need to reduce infection risk due to suture exposure to the oral cavity, to improve the surgeon's range and ability to precisely locate and orient the suture loop, and to improve the ability of surgeons to properly tension the suture the implanted suture loop by eliminating the need to perform knot-tying while simultaneously controlling the final tension of the suture loop.

SUMMARY OF THE INVENTION

The present disclosure provides suture passer system and methods for tongue or other tissue suspension or compression. In certain embodiments, the suture passer may be delivered into tissue and can comprise at least an elongate shaft and a needle carried within the elongate shaft. The needle may be configured to carry a suture, and the suture may be grabbed by a retrieval element to form suture loop(s) within the tissue. The system can also include one or more bone anchors to secure the suture loop(s).

Some embodiments of the present disclosure relate to a method of treating a condition of an airway. The method comprises providing a suture passer, which comprises a proximal handle, a first elongate shaft extending distally from the proximal handle, a second elongate shaft extending distally from the proximal handle, a needle carried within the first elongate shaft, the needle being extendable from and retractable into the first elongate shaft, the needle having a substantially straight configuration when located within the first elongate shaft, the needle configured to exit an opening at or near a distal end of the first elongate shaft and form a curved or lateral path through tissue toward the second elongate shaft, and a suture carried by the needle, wherein the second elongate shaft comprises a suture-receiving element having an opening configured to capture the suture. The method further comprises inserting the suture passer into a patient's tongue, wherein said inserting advances the suture distally into and through tongue tissue; moving the needle from a retracted position within the first elongate shaft through the opening in the first elongate shaft to an extended position within the tongue tissue to form a curved or lateral path through the tongue tissue, the needle carrying the suture along the path; capturing the suture from the needle at a location within the tongue tissue with the suture-receiving element; retracting the needle into the first elongate shaft; withdrawing the suture passer from the tongue while the suture remains captured by the suture-receiving element to place a suture loop in the tongue; and advancing the patient's tongue forward to relieve airway obstruction using a suture that follows the path of the suture loop placed by the suture passer, wherein the suture is secured near the patient's mandible to suspend the tongue. In some embodiments, the suture used to advance the patient's tongue can be a second suture and the suture loop placed by the suture passer can be placed using a first suture, and wherein the second suture can be advanced into the tongue tissue by pulling the first suture out of the tongue tissue, the second suture attached to the first suture. The first suture can be a guide suture, wherein the guide suture can have a width that is less than the width of the second suture. In some other embodiments, the suture can be attached to the patient's mandible with a bone anchor. In still some other embodiments, the suture-receiving element can comprise a snare that is extendable and retractable with respect to the second elongate shaft. In still yet some other embodiments, the suture-receiving element can comprise an aperture configured to house the suture therethrough, and an axially movable wall for closing the aperture to reversibly retain the suture. In some embodiments, the suture loop can be substantially vertically oriented after being placed within the tongue tissue. In other embodiments, the suture loop can be substantially horizontally oriented after being placed within the tongue tissue. In still some other embodiments, the first and second elongate shafts can comprise blunt distal tips. In yet some other embodiments, the method can further comprise, after withdrawing the suture passer to place the suture loop, reloading a suture onto the needle and placing a second suture loop in the tongue. In still yet some other embodiments, a distal end of the needle can comprise a first lateral portion, a central portion, and a second lateral portion, the central portion protruding distally beyond the first lateral portion and the second lateral portion. In some embodiments, the first elongate shaft and the second elongate shaft can be substantially the same length. In other embodiments, the method can further comprise adjusting the distance between the first elongate shaft and the second elongate shaft to adjust the amount of tongue tissue to be captured. In still some other embodiments, the first and second elongate shafts can be substantially parallel to one another.

In another embodiment of the present disclosure, a method of treating tissue is provided. The method comprises delivering an elongate shaft into tissue; delivering a needle having a distal end configured to be laterally biased and carried within the elongate shaft further through the tissue, the needle carrying a suture, the needle exiting an opening in the elongate shaft and forming a curved or lateral path through tissue not coaxial with a longitudinal axis of the elongate shaft to carry the suture along the path; and grabbing the suture with a retrieval element at a location within the tissue; wherein the needle is retractable back into the elongate shaft; wherein the retrieval element is operably connected to the elongate shaft. The tissue can be tongue tissue. In some embodiments, the elongate shaft can comprise a first elongate shaft member and a second elongate shaft member, the first elongate shaft member releasably housing the needle and the second elongate shaft member comprising the retrieval element. In other embodiments, delivering the elongate shaft can comprise delivering the elongate shaft into tongue tissue without passing through the tongue mucosa. In still some other embodiments, the method can further comprise withdrawing the elongate shaft from the tissue to place at least one suture loop within the tongue tissue; and suspending the tongue by securing suture passed through the tongue tissue to a bone anchor. In yet some other embodiments, the suture passed through the tongue tissue can be the suture placed by the elongate shaft. In still yet some other embodiments, the suture passed through the tongue tissue can be a tension element inserted into the tongue tissue that follows the path of the suture loop placed by the elongate shaft, wherein the suture loop can have a width that is less than the width of the tension element. The tension element can be advanced into the tissue by pulling the suture loop placed by the elongate shaft out of the tongue tissue, the tension element attached to the suture loop. In some embodiments, the method can further comprise attaching the bone anchor to bone before grabbing the suture with a retrieval element at a location within the tongue tissue. In other embodiments, securing suture passed through the tongue tissue to the bone anchor can be accomplished after grabbing the suture with a retrieval element at a location within the tongue tissue. In still some other embodiments, securing suture passed through the tongue tissue to the bone anchor can comprise threading a portion of suture through an eyelet of the bone anchor, and reducing a height dimension of the eyelet such that the portion of suture is retained within the eyelet. Reducing the height dimension of the eyelet can comprise reducing the height dimension of the eyelet to between about 0.005 inches and about 0.020 inches. In some embodiments, the bone anchor can be attached to a mandible. The bone anchor can comprise a proximal head portion having an eyelet having a sidewall with a distal surface defining a first cavity therein and configured for at least one suture to pass therethrough and a distal threaded portion for engaging a bone, wherein the proximal head portion comprises a locking screw having a proximal end and a distal end, the locking screw configured to fit within a second cavity that communicates with the first cavity, wherein rotation of the locking screw to move the locking screw in a distal direction allows the locking screw to enter the first cavity and decrease the height dimension sufficient to prevent movement of the suture within the eyelet, wherein the height dimension is defined by the distance between the distal surface of the cavity and the distal end of the locking screw, wherein the height dimension is greater than zero. The height dimension sufficient to prevent movement of suture within the eyelet can be between about 0.005 inches and about 0.02 inches. In other embodiments, the bone anchor can comprise a proximal head portion having an eyelet defining a cavity therein and configured for at least one suture to pass therethrough, wherein the proximal head portion comprises a cam lock configured to rotate within the cavity, the cam lock comprising a shaft member radially offset from a longitudinal axis of the cam lock and connected between two cylindrical bearings, wherein the rotation of the cam lock can be configured rotate the shaft member to reduce a space between an inner wall of the cavity and an outer surface of the shaft member, the rotation of the cam lock defining an open state and a closed state; and a distal threaded portion for engaging tissue; wherein the space in the closed state can be dimensioned to effectively secure the suture between outer surface of the shaft member and the inner wall of the cavity. The proximal head portion can comprise a plurality of faces forming a symmetrical polygonal shape, the eyelet radially offset from an axis of symmetry of the polygonal shape. In some other embodiments, the method can further comprise suspending the tongue with a suture comprising a substantially flattened section. The suture used for suspending the tongue can comprise a radiopaque marker.

In yet another embodiment of the present disclosure, a method for treating tissue is provided. The method comprises creating a first pathway within the tissue; creating a second pathway within the tissue; passing a flexible elongate member extending through the first pathway through tissue from the first pathway to the second pathway; and withdrawing the flexible elongate member through the second pathway, leaving the flexible elongate member to form a looped path through the tissue. The tissue can be tongue tissue. In some embodiments, the method can further comprise advancing a tensioning structure through the looped path, wherein the structure is attached to the flexible elongate member and the flexible elongate member is removed from the tongue tissue; and securing the tensioning structure to a body structure to apply force to the tongue. In other embodiments, the body structure can be a bone. The bone can be the mandible. Or, the bone can be the hyoid. In still some other embodiments, the first pathway and second pathway can be created with a suture passer having two elongate shafts connected to one another, and the flexible elongate member can be a suture that is passed from one elongate shaft to the other with a needle that passes through the tongue tissue. In still yet some other embodiments, the flexible elongate member can be a guide suture having a width that is less than the width of the structure.

In still yet another embodiment of the present disclosure, a suture passer is provided. The suture passer comprises a proximal handle having an actuator control; a first elongate shaft extending distally from the handle; a second elongate shaft extending distally from the handle; a needle carried within the first elongate shaft, the needle configured to extend from and retract into the first elongate shaft, the needle having a substantially straight configuration when located within the first elongate shaft, the needle configured to exit an opening at or near a distal end of the first elongate shaft and form a curved or lateral path through tissue toward the second elongate shaft upon actuation of the actuator control; and a suture carried by the needle; wherein the second elongate shaft comprises a suture-receiving element having an opening configured to capture the suture, wherein the first elongate shaft and the second elongate shaft have substantially the same lengths. In some embodiments, the suture passer can be configured for delivering suture into tongue tissue. The first elongate shaft and the second elongate shaft can have blunt distal ends that are configured to prevent penetration of the tongue mucosa. In some other embodiments, the suture-receiving element can comprise a snare extendable from and retractable from an elongate shaft. In other embodiments, the suture-receiving element can comprise a hypotube having an aperture sized and configured to receive the suture. In yet some other embodiments, the first and second elongate shafts can be substantially parallel to one another. In still yet some other embodiments, the needle can comprise a distal end made of a superelastic material. In some embodiments, the method can further comprise a light source configured to emit light through the first and second elongate shafts to transilluminate tissue.

In another embodiment of the present disclosure, a system for treating a condition of an airway is provided. The system comprises a suture passer configured to deliver suture into tongue tissue. The suture passer can comprise a proximal handle; a first elongate shaft extending distally from the proximal handle; a second elongate shaft extending distally from the proximal handle; a needle carried within the first elongate shaft, the needle being extendable from and retractable into the first elongate shaft, the needle having a substantially straight configuration when located within the first elongate shaft, the needle configured to exit an opening at or near a distal end of the first elongate shaft and form a curved or lateral path through tongue tissue toward the second elongate shaft; and a suture carried by the needle; wherein the second elongate shaft comprises a suture-receiving element having an opening configured to capture the suture. The system can further comprise a bone anchor for anchoring into a patient's bone and configured to tension a tensioning element positioned in a path in tongue tissue formed by the suture passer. In some embodiments, the first elongate shaft and the second elongate shaft can have blunt distal ends that may be configured to prevent penetration of the tongue mucosa. In other embodiments, the tensioning element can be the same as the suture delivered by the suture passer into tongue tissue. In some other embodiments, the tension element can be a separate element configured to be guided into the tongue tissue by the suture delivered by the suture passer. In still some other embodiments, the suture-receiving element can comprise a snare extendable from and retractable from an elongate shaft. In yet some other embodiments, the suture-receiving element can comprise a hypotube having an aperture sized and configured to receive the suture. In some embodiments, the first and second elongate shafts can be parallel to one another. In other embodiments, the needle can comprise a distal end made of a superelastic material. In some other embodiments, the system can further comprise a light source configured to emit light through the first and second elongate shafts to transilluminate tissue. In yet some other embodiments, the first elongate shaft and the second elongate shaft can be the same length. In still yet some other embodiments, a distance between the first elongate shaft and the second elongate shaft can be adjustable to adjust the amount of tongue tissue to be captured. In some embodiments, the bone anchor can be configured for anchoring into a patient's mandible. In other embodiments, the bone anchor can comprise an eyelet for receiving the tensioning element. In still some other embodiments, the bone anchor can comprise a proximal head portion having an eyelet having a sidewall with a distal surface defining a first cavity therein and configured for at least one suture to pass therethrough and a distal threaded portion for engaging a bone, wherein the proximal head portion comprises a locking screw having a proximal end and a distal end, the locking screw configured to fit within a second cavity that communicates with the first cavity, wherein rotation of the locking screw to move the locking screw in a distal direction allows the locking screw to enter the first cavity and decrease the height dimension sufficient to prevent movement of the suture within the eyelet, wherein the height dimension is defined by the distance between the distal surface of the cavity and the distal end of the locking screw, wherein the height dimension is greater than zero. In still yet some other embodiments, the bone anchor can comprises a proximal head portion having an eyelet defining a cavity therein and configured for at least one suture to pass therethrough, wherein the proximal head portion comprises a cam lock configured to rotate within the cavity, the cam lock comprising a shaft member radially offset from a longitudinal axis of the cam lock and connected between two cylindrical bearings, wherein the rotation of the cam lock is configured rotate the shaft member to reduce a space between an inner wall of the cavity and an outer surface of the shaft member, the rotation of the cam lock defining an open state and a closed state; and a distal threaded portion for engaging tissue; wherein the space in the closed state is dimensioned to effectively secure the suture between outer surface of the shaft member and the inner wall of the cavity. In some embodiments, the tensioning element is a suture. The suture can comprise a flattened section. In still yet some other embodiments, the tensioning element can comprise a radiopaque marker.

Other embodiments of the present disclosure include bone anchors, screws, sutures, suture locking and tensioning elements, and suture adjustment tools as described herein. All of these embodiments are also intended to be within the scope of the invention herein disclosed, and may be used in the systems and methods described herein.

BRIEF DESCRIPTION OF THE DRAWINGS

FIG. 5F illustrates an embodiment of a suture receiving element within a hypotube.

FIGS. 7A-7D illustrate a method of delivering a plurality of suture loops into tissue having a common midline axis, according to one embodiment of the invention.

FIGS. 7F-7N illustrate one embodiment of a method to create a suture loop in the base of the tongue.

FIGS. 7S-7W illustrate a method of passing a suture loop around a structure other than tissue, according to one embodiment of the invention.

FIG. 9A depicts a suture passer system in one embodiment showing bite adjustment by rotational control after insertion.

FIG. 9B depicts a suture passer system in the embodiment in FIG. 9A showing bite adjustment by rotational control before insertion.

FIG. 11A depicts a suture passer system in an embodiment illustrating non-parallel shafts.

FIG. 11B depicts a suture passer system in another embodiment illustrating a shaft angle control to adjust one or both shaft angles.

FIG. 15A provides an isometric view, FIG. 15B provides an end view, and FIG. 15C provides a side view.

FIG. 16A provides a side view and FIG. 16B provides an end view.

FIG. 17A provides an isometric view, FIG. 17B provides a side view, and FIG. 17C provides an end view.

FIG. 23A illustrates one embodiment of a method of locking or tensioning a suture loop.

FIG. 23B illustrates another embodiment of a method of locking or tensioning a suture loop.

FIGS. 25C and 25D represent rotated side views, and FIG. 25E is a view of the proximal end of the suture passer system 2500, with one non-limiting example of various dimensions of the device.

FIG. 27A illustrates an embodiment of a suture adjustment tool for spooling or releasing one or more sutures.

FIG. 27B illustrates a magnified view of a distal end of the suture adjustment tool of FIG. 27A.

FIG. 29A illustrates an embodiment of a bone anchor having a second eyelet.

FIG. 29B illustrates a top view of the bone anchor of FIG. 29A.

FIG. 29C illustrates an embodiment of a method of securing a second suture loop to the bone anchor of FIG. 29A.

FIGS. 30A-30B illustrate embodiments of sutures having a portion with a flattened configuration, and optionally radiopaque elements.

DETAILED DESCRIPTION OF THE PREFERRED EMBODIMENTS

Figure 1B:
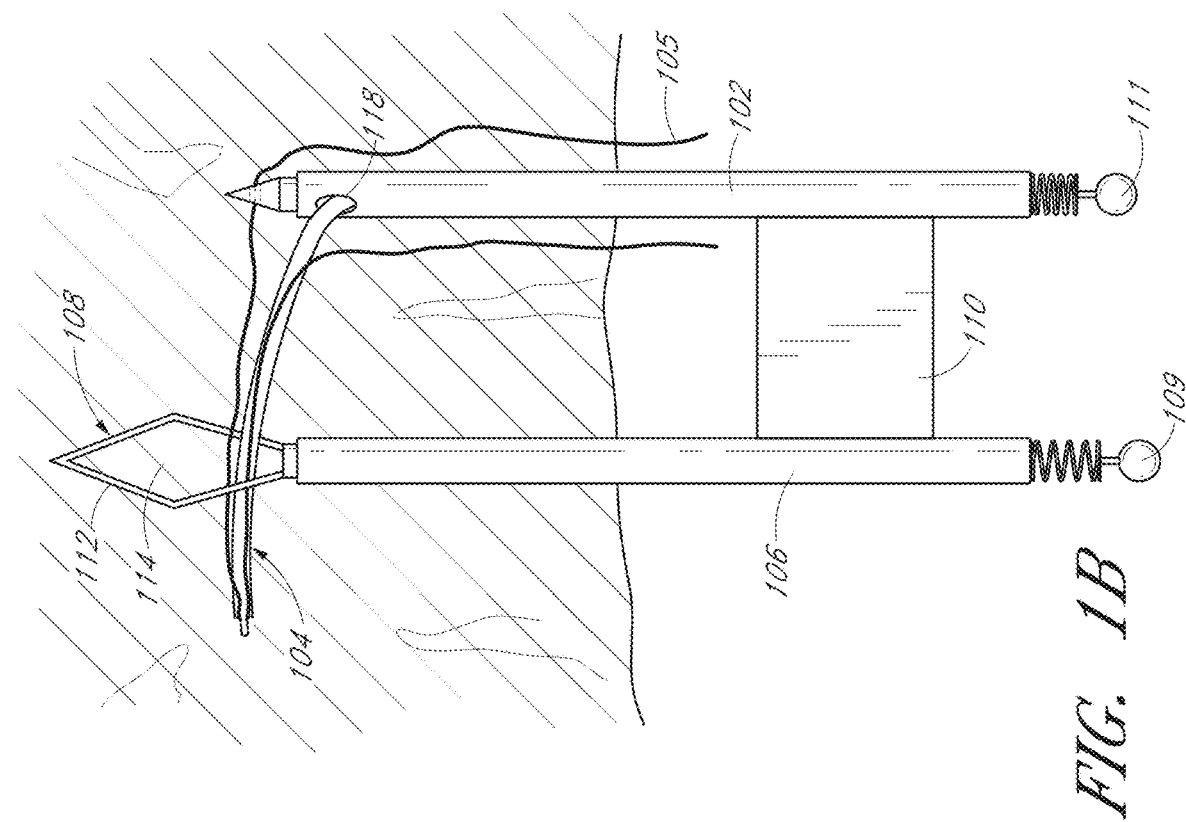
FIGS. 1A-1B illustrate one embodiment of a suture passer system with a first and second shaft, housing respective suture-passing and suture-receiving elements.

In one embodiment, disclosed is a suture passer system and method for passing a suspension line, such as a tether, tether loop, suture or suture loop through tissue to suspend or compress the tissue. The term "suture" as used herein, unless otherwise specified or limited, is intended to have its ordinary meaning and is also intended to include all structures, including any of the aforementioned or later-described examples, that can be passed through tissue using the devices described herein. One example of tissue that can be suspended or compressed is the genioglossus muscle of the tongue. Such a system could be useful in treating a wide range of conditions, including, for example, obstructive sleep apnea. Other non-limiting examples of tissues that can be suspended or compressed include using systems and methods as described herein include facial soft tissue such as in the forehead, brow, mid face, jowls, lateral face, lips, eyelids, nose, and neck to treat wrinkles or asymmetry; the breast and/or nipple-areola complex to treat ptosis; the bladder, such as the bladder neck to treat incontinence or a cystocele; the uterus or vagina to treat prolapse; or muscles, tendons, and/or ligaments to treat a partial or complete tear. The suture passer system could be used to ligate blood vessels such as arteries or veins that are not easily accessible without a surgical access procedure. Other non-limiting examples of anatomical structures that can be suspended other luminal structures such as a lymphatic, fallopian tube, bile duct, or ureter; or an organ such as, for example, the esophagus, stomach, small intestine, colon, rectum, bladder, uterus, vagina, eye, liver, lung, gallbladder, spleen, pancreas, or kidney. The suture passer can also be used to suspend other structures located within tissue, such as bone, as will be described further below.

In some embodiments of the invention, the tether loop comprises sutures or wires. Such materials are generally inelastic and may be useful to fix the distance between the distal end of the loop in the tissue to be fixed and the proximal anchor. However, a tether with elastic properties or comprising structures that provide a length/tension relationship may be preferred in some instances. A tether capable of lengthening in response to increased load or tension may be optimized to provide sufficient bias to reduce the effects of oropharyngeal occlusion while providing a more physiologic range of tongue motion than that produced by fixed length tethers. Fixed length glossoplasty or suspension of the tongue may be the cause of odynophagia, dysphagia and deglutition problems seen with existing tongue remodeling devices, but the current invention is not limited to this purpose. A tether with elastomeric properties may be provided by using materials such as but not limited to urethane or silicone. One skilled in the art can select the particular material, tether length, diameter, cross-sectional shape and other features based upon the desired effect, tolerances, and the particular patient's anatomical characteristics. Other materials that may comprise the tether include but are not limited to Nitinol, spring steel, tantalum, polyethylene, polyester, silk, polypropylene, polyolefin or a combination thereof.

Other tether configurations that may be used include passive and active variable length or bias structures such as braided or woven structures, electropolymers, springs, coils, magnets or solenoids. Thus, in some of the embodiments, the tether configuration may actively change in length in length or configuration resulting from the application of external energy or force such as electrical current or magnets. These active tether configurations may be further configured with local or distal sensor components that may modulate the activity of the external energy or force acting on the active tether. The modulation may be influenced or triggered by detection of diaphragm movement or depolarization activity, nerve depolarization, pressure changes and/or mechanical contact in the airway.

The tether may also be covered by a lubricious biocompatible coating. In another embodiment, the tether comprises a bioabsorbable coating that may cause scar or connective tissue formation about the tether. Scar tissue formation may further enhance the effect of the tether loop by tightening the tongue tissue and/or to resist cheese-cutter type migration of the loop. In still other embodiments, the tongue element may comprise multiple distal anchors and multiple tethers arranged in a serial or branching fashion. While the use of suture(s) or suture loops are described herein, the use of non-suture tethers including those described above and elsewhere herein may also be utilized in any of the disclosed embodiments as well.

Figure 1A:
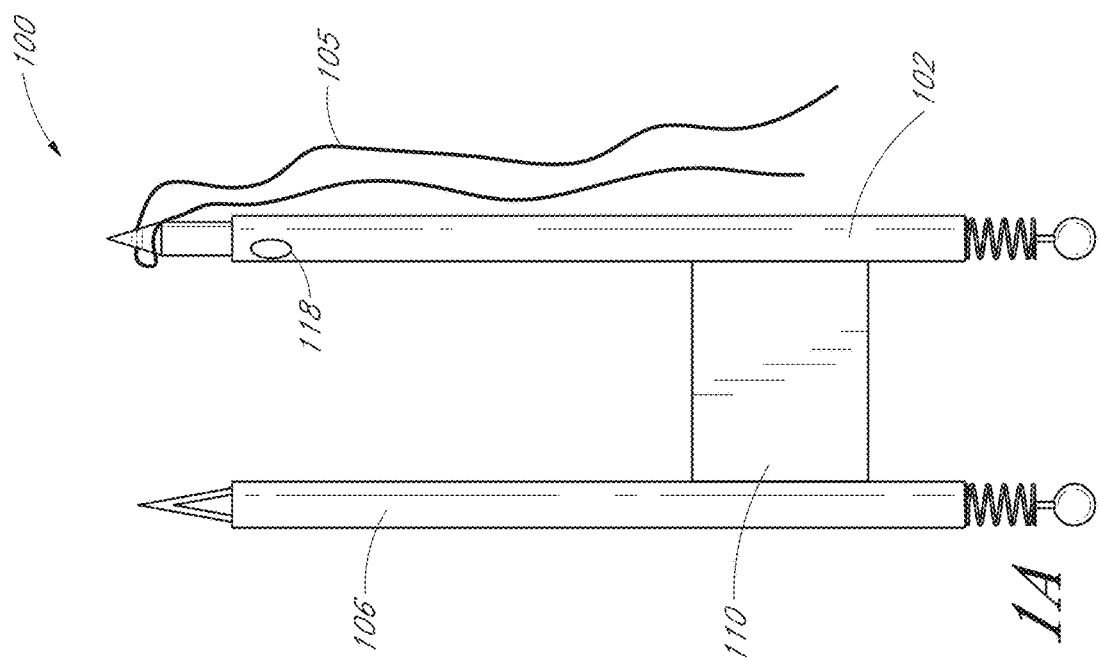

As illustrated in FIGS. 1A-1B, the suture passer 100 can include a first elongate tubular body or shaft 102 configured to releasably house a suture passing element 104 (e.g., a flexible needle) and one, two, or more tethers, e.g., sutures 105 therethrough carried by the suture passing element 104, and a second elongate tubular body or shaft 106 configured to house a suture receiving element 108 (e.g., a snare) therethrough. The second elongate shaft 106 serves as a retrieval element described further below. Portions of the one or more sutures 105 may reside outside of the first elongate shaft 102. The first elongate shaft 104 and second elongate shaft 106 can be operably connected via connector 110. The connector can be near the proximal end of the suture passer 100 as illustrated, or alternatively near the midpoint or distal end of the suture passer 100. In some embodiments, the first elongate shaft 104 and the second elongate shaft 106 are integrally formed together, or otherwise glued, welded, or otherwise attached. In some embodiments, the first elongate shaft 104 and second elongate shaft 106 are removably attached, such as via reversibly interlocking elements for example, to facilitate use of different needles 104 or suture-receiving elements 108 depending on the desired clinical result. While the distal ends of shafts 104, 106 may be sharpened to facilitate tissue penetration, in some embodiments, one or both distal tips of shafts 104, 106 may be blunt to prevent distal penetration through the mucosa, thus preventing a through-and-through puncture. The first elongate shaft 102 and the second elongate shaft 106 may be parallel or substantially parallel to one another.

In some embodiments, the first elongate shaft 102 and the second elongate shaft 106 can extend distally from a proximal handle 111. The first elongate shaft 102 and the second elongate shaft 106 can be substantially the same length, having a length of between about 4 cm to about 30 cm, with lengths from the connection 110 to the distal end of the shafts of between 4 cm and 10 cm in some embodiments. In other embodiments, the first elongate shaft 102 could have a length that is no more than about 90%, 80%, 70%, 60%, 50%, 40%, 30%, or less of the length of the second elongate shaft 106. In still other embodiments, the first elongate shaft 102 could have a length that is at least about 110%, 120%, 130%, 140%, 150%, or more of the length of the second elongate shaft 106.

In one embodiment for tongue suspension, the shafts are separated by distance of 0.5 cm to about 5 cm, with a separation of 0.5 cm to 2.5 cm in some embodiments. The first elongate shaft can include bent-out tabs or extensions to secure and guide the portions of the one or more sutures 105 that are not housed within the first elongate shaft 102. In some embodiments, at least a portion of the first elongate shaft 102 and/or the second elongate shaft 106 has a flattened cross-section to better maintain alignment.

Figure 1C:
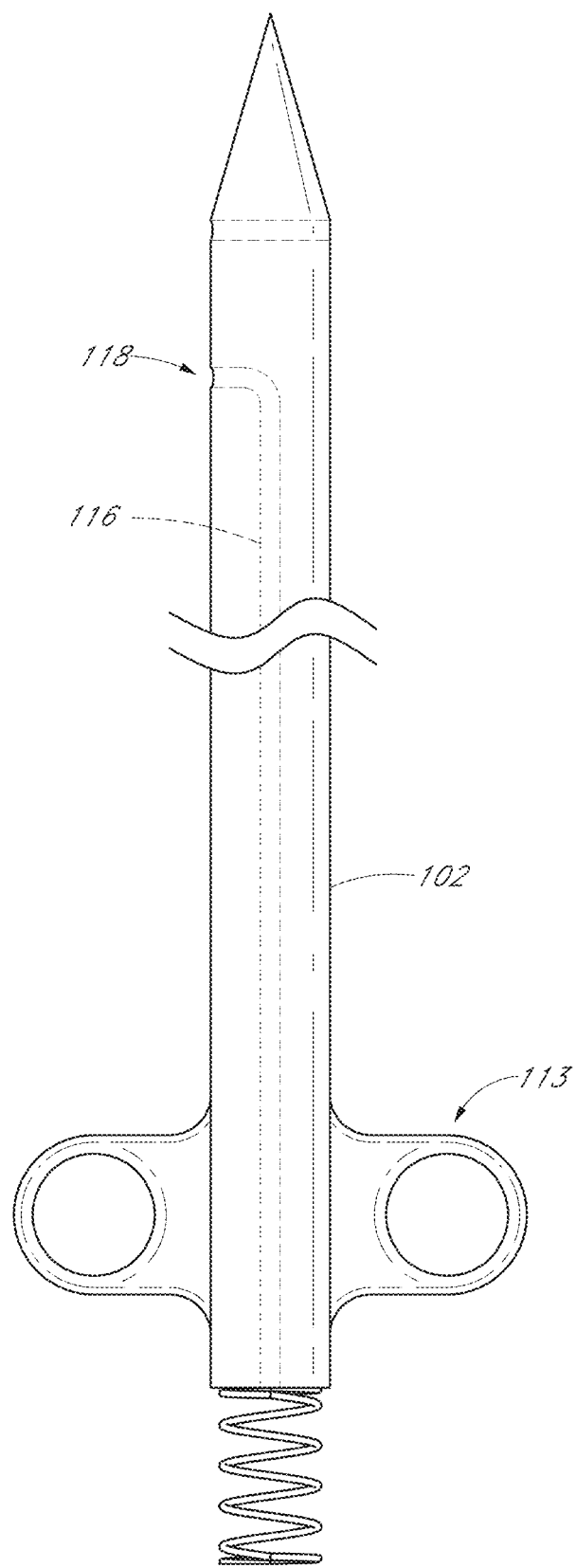
FIG. 1C illustrates a cross-sectional view of a first shaft of a suture passer system.

As illustrated in FIGS. 1B and 1C, the flexible needle 104 is housed within the first elongate shaft 102 in a lumen 116 which has a proximal portion that is coaxial with the longitudinal axis of the first elongate shaft 102, and a distal portion and an exit aperture 118 that extends at an angle with respect to the long axis of the first elongate shaft 102. In some embodiments, the angle is between about 10-170 degrees, such as between about 45-135 degrees, or about 90 degrees in some embodiments. The flexible needle 104 is in a substantially straight configuration while within the lumen 116 of the first elongate shaft 102, but has a distal end that reversibly assumes a laterally biased (e.g., curved or bent) configuration that is not coaxial with the longitudinal axis of the first elongate shaft 102 upon emerging out of exit aperture 118, such as, for example, by distal advancement of the proximal handle 111, or by actuation of a control such as a wheel, switch, or the like. The needle 104 can be retracted back into the first elongate shaft 102 in a similar manner. In some embodiments, distal advancement of the proximal handle 111 can occur by actuation of springs. A distal end 120 of needle 104 may be biased to have an unstressed curved configuration by being made of a shape memory or superelastic material, such as Nitinol or a shape memory polymer, for example. In other embodiments, needle 104 can assume a curved configuration via internal pullwires, for example. In still other embodiments, the distal end 120 of the needle 104 is substantially straight in an unstressed configuration, and can be laterally biased as it emerges from the exit aperture 118 of the first elongate shaft 102 via a needle-redirecting element such as a laser-cut tang or plug placed proximate to the exit aperture 118 and causing the distal end 120 of the needle 104 to laterally bend. In some embodiments, the distal end 120 of the needle 104 can comprise a first lateral portion, a central portion, and a second lateral portion, the central portion protruding distally beyond the first lateral portion and the second lateral portion.

Figure 1D:
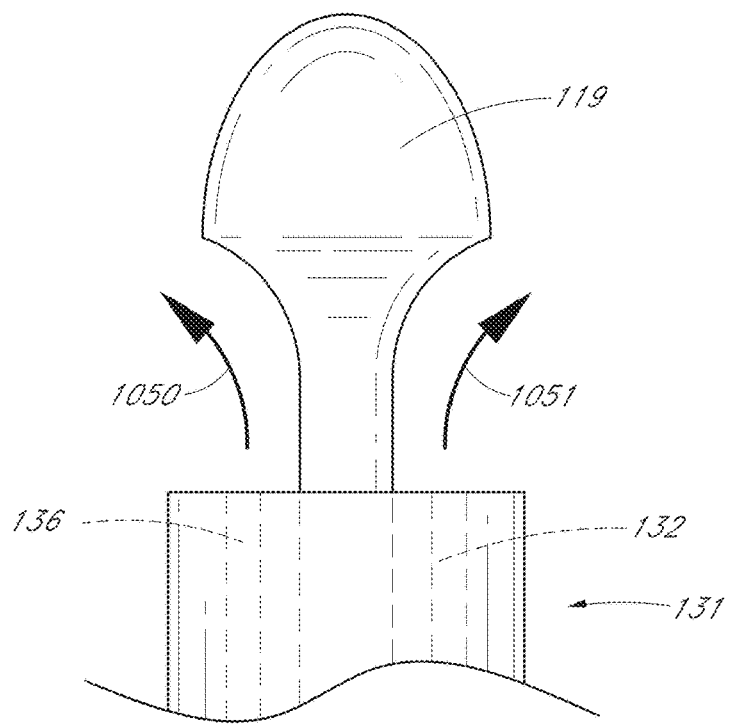
FIGS. 1D-1G illustrate another embodiment of a suture passer system with a deflecting element.

In some embodiments, the suture-receiving element 108 and/or the needle can be deflected along different trajectories. For example, the suture-receiving element 108 can be deflected along a first trajectory (e.g., arrow 1050), and the needle 104 can be deflected along a second trajectory (e.g., arrow 1051). With reference to FIGS. 1D-1G, one embodiment of a suture passer system 100 is illustrated having a deflecting element 119. In such an embodiment, the suture passer 100 comprises a single elongate shaft 131 that can have a first pathway 136 configured such that the distal end of the suture-receiving element 108 passes therethrough and a second pathway 132 configured such that the distal end of the suture-passing element 104 passes therethrough. Embodiments as described wherein the suture-passing element 104 and suture-receiving element 108 share a common elongate shaft 131 advantageously provides a single insertion point for the suture passer system 100. As shown in FIG. 1D, one, two, or more deflecting elements 119 can be located proximate the distal end of the common elongate shaft 131 which can extend at least partially distally along the longitudinal axis of the single elongate shaft 131. The deflecting element 119 may extend from within the single elongate shaft 131, integrally formed with the shaft 131, or otherwise attached to the single elongate shaft 131. In some embodiments, instead of a single deflecting element 119 with surfaces to both deflect the suture-passing element 104 and suture-receiving element 108, two separate deflecting elements could be used, one for the suture-passing element 104 and one for the suture-receiving element 108.

Figure 1E:
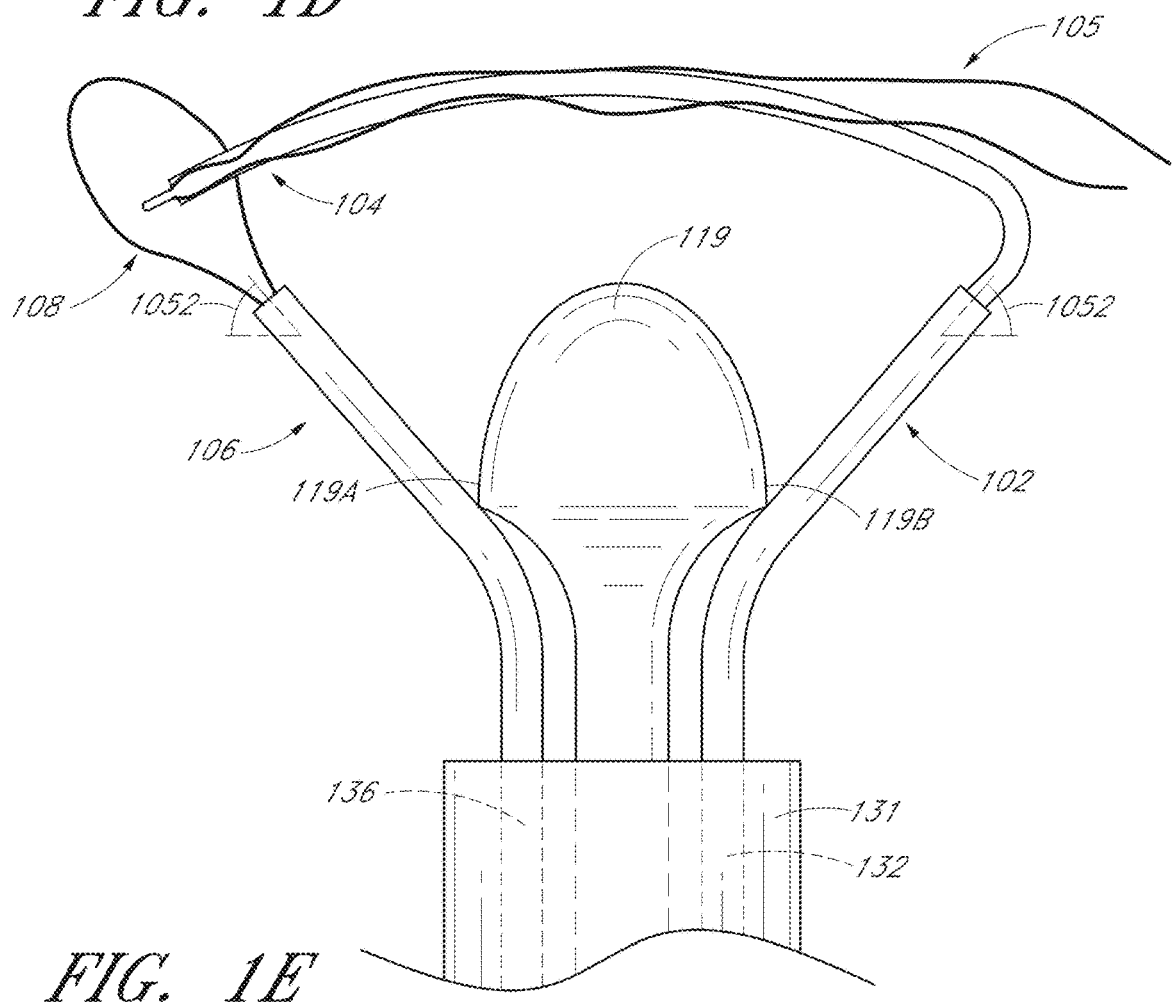
Figure 1F:
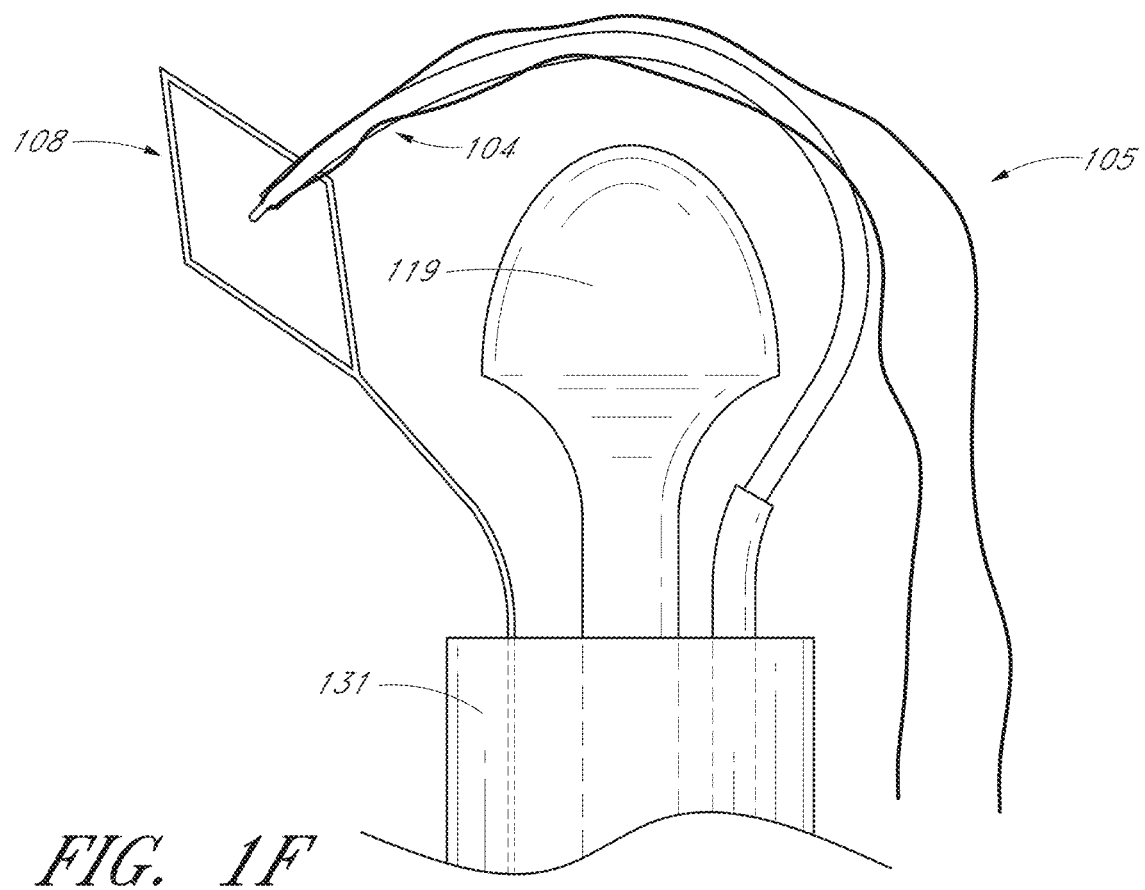

Still referring to FIG. 1D, the deflecting element 119 can have one, two, or more surfaces that may include a laterally facing or curved segment configured to deflect the snare 108 and the needle 104 along different trajectories. The deflecting element 119 may be configured to have a first surface 119A and/or a second surface 119B to deflect the snare 108 and the needle 104 respectively away from the longitudinal axis of the single elongate shaft 131. In some embodiments, the first surface 119A and the second surface 119B cause the deflected distal ends of the suture-receiving element 108 and/or the suture-passing element 104 to form an angle with the longitudinal axis of the elongate shaft 131 that is between about 0-180 degrees, 0-90 degrees, 10-80 degrees, or 30-60 degrees. The aforementioned angles could be the same, or different in some embodiments by at least 10, 20, 30 degrees, or more. Controlling the deflection angle of the suture-receiving 108 and suture-passing 104 elements can advantageously improve the accuracy of the snare 108 in capturing the needle 104. As illustrated in FIG. 1E, the deflecting element 119 extends from a central portion of the single elongate shaft 131. On one side near surface 119B of the deflecting element 119, the suture-passing element 104 or a first elongate shaft 102 of the suture-passing element 104 extends distally from a first pathway 132 and is deflected along a laterally biased or curved path. Furthermore, on another side near surface 119A of the deflecting element 119, a suture-receiving element 108 or a second elongate shaft 106 of the suture-receiving element 108 extends distally from a second pathway 136 and is also deflected along another laterally biased or curved path. In some embodiments, the distal ends of suture-receiving element or suture-receiving element shaft and the distal end of suture-passing element and suture-passing element shaft can form an angle 1052 that is between about 0-180 degrees, such as between about 45-135 degrees, 60-120 degrees, or about 90 degrees. In some embodiments, the first and the second elongate shafts 102 and 106 are made of a flexible material, and may comprise an elongate element with a window as described elsewhere herein, e.g., in FIGS. 5F-5I below. In some embodiments, as shown in FIG. 1F, the snare 108 and/or the needle 104 may comprise a shape memory material (e.g., Nitinol or a shape memory polymer) to extend from the single elongate shaft 131 without separately requiring deflection of the first 102 and the second 106 elongate shaft.

Figure 1G:
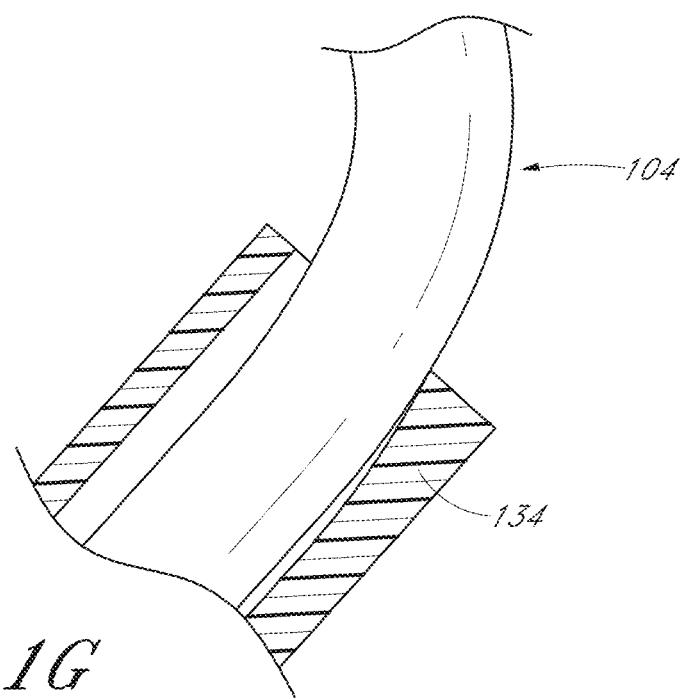

FIG. 1G provides a cross-sectional view of the distal end of the first elongate shaft 102 from FIG. 1E. In the illustrated embodiment, a needle guide 134 is provided at the distal end of the first elongate shaft 102 to control the trajectory of the needle 104, in addition to or in combination with the deflecting element 119. The needle guide 134 may have a curved or laterally biased portion configured to deflect the needle 104 along a curved or laterally biased path to improve the accuracy of the snare 108 capturing the needle 104. When the sutures 105 are captured in the snare 108 and the suture passer 100 is withdrawn from tissue, the sutures 105 advantageously form a loop that can be centered on the longitudinal axis of the single elongate shaft 131.

An elongated distal tip may be added to the deflecting element 119 or to the end of the elongated shaft of the suture passer. In this embodiment the elongated shaft of the suture passer is inserted to a desired tissue depth (by appropriate imaging or palpation of the distal tip). The suture is then passed just at or at a set distance beyond the distal tip of the suture passer. Passing the suture at or beyond the distal tip of the suture passer, can be advantageous. In the case of tongue suspension, the suture passer is inserted through the muscle of the tongue, but encounters much stiffer resistance when it contacts the mucosal layer. With the distal tip of the suture passer thus inserted at the interface of the muscle and mucosa, the suture pass can then be made right at this interface or at a known depth in the mucosa. This type of suture pass can be advantageous in tongue suspension: it places the suture at the closest possible location to the tissues that obstruct the airway and it may provide more secure anchoring of the suture in some embodiments by having it pass into the tougher tissues of the mucosal layer.

Figure 1H:
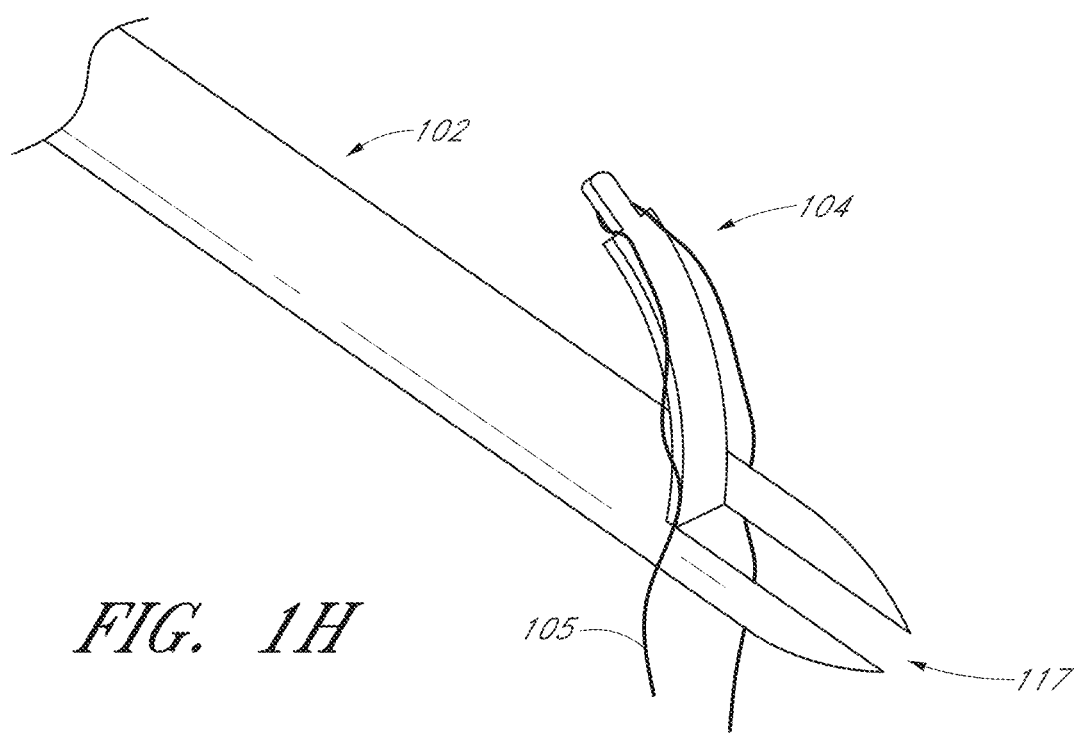
FIGS. 1H-1I illustrate views of a suture-receiving element having a slot for receiving a suture, according to one embodiment of the invention.
Figure 1I:
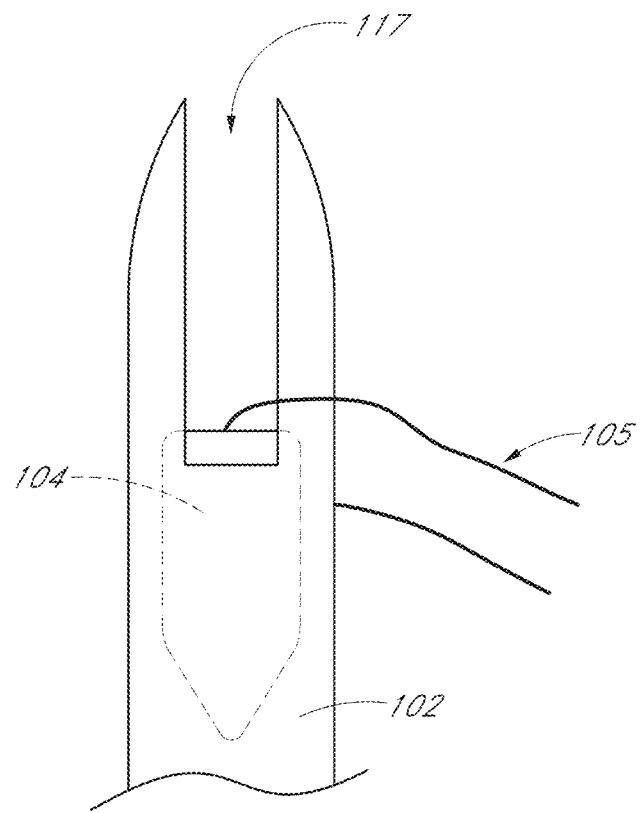

Excessive suture drag during needle extension can affect the trajectory and path of the needle, potentially keeping the needle from properly engaging the snare. In some embodiments, suture drag of the system is minimized by the presence of a pathway 117 such as a slot at the distal end of the elongated needle shaft, which can in some embodiments oriented lengthwise substantially parallel to the long axis of the first elongate shaft 102, as illustrated in the side and bottom views of FIGS. 1H and 1I, respectively. This pathway allows the suture to closely follow the intended needle path and minimizes suture drag resistance by eliminating unnecessary suture pathway bends, twists, or lengths.

In some embodiments, the flexible needle 104 may have a distal laterally biased length that is between about 0.5 cm to about 5 cm for tongue applications. The flexible needle 104 can include a shouldered-tip or one, two, or more apertures, slots, notches, grooves, clips, or other features at or near its distal end (not shown) for releasably carrying the one or more sutures 105. Carrying the suture on a shouldered distal tip of the suture needle allows a suture loop to be easily loaded from the end of the suture needle. It provides the ability to carry a loop of suture versus a suture strand and it also keeps the suture on the backside of the suture needle during the suture pass, thus ensuring that the suture passes through the pathway created by the suture needle and does not cut or erode into surrounding tissues during the suture pass.

In some embodiments, the needle 104 comprises an elongate ribbon, such as a ribbon having a first length or width dimension that is at least about 10%, 50%, 100%, 500%, 1000%, or more of a second length or width dimension. In some embodiments, the needle 104 can have a variable stiffness to control the flexibility of the needle 104 in various locations. For example, the needle 104 could have a first stiffness in a proximal portion of the needle 104 and a second stiffness in a distal portion of the needle 104, the second stiffness less than about 90%, 80%, 70%, 60%, 50%, or less of the first stiffness, to allow the distal portion to flex, bend, or curve. Variable stiffness or shape-memory features may also be used to reduce or improve suture needle extension or retraction forces.

FIG. 1C additionally illustrates a proximal grip 113 operably connected to the proximal end of the suture passer 100. As noted above, the needle 104 is axially and/or radially movable with respect to the first elongate shaft 102 to facilitate intra-tissue suturing. However, in other embodiments, the needle is not axially movable with respect to the shaft, as described, for example, in FIGS. 1-7 and paragraphs [0011] to [0020] of U.S. Pat. Pub. No. 2009/0018554 A1 to Thorne et al., hereby incorporated by reference in its entirety.

In some embodiments of the invention, the tethers to be passed through tissue comprise sutures or wires as known in the art. Such materials are generally inelastic. However, in some embodiments a tether with elastic properties or comprising structures that provide a length/tension relationship may be preferred in some instances. A tether capable of lengthening in response to increased load or tension may be optimized to provide sufficient bias to reduce the effects of oropharyngeal occlusion while providing a more physiologic range of tongue motion than that produced by fixed length tethers. Fixed length glossoplasty or suspension of the tongue may be the cause of odynophagia, dysphagia and deglutition problems seen with existing tongue remodeling devices, but the current invention is not limited to this purpose. A tether with elastomeric properties may be provided by using materials such as but not limited to urethane or silicone. One skilled in the art can select the particular material, tether length, diameter, cross-sectional shape and other features based upon the desired effect, tolerances, and the particular patient's anatomical characteristics. Other materials that may comprise the tether include but are not limited to Nitinol, spring steel, tantalum, polyethylene, polyester, silk, polypropylene, polyolefin or a combination thereof. In some embodiments, the tether can be at least partially or completely radioopaque that may be advantageous, for example, if fluoroscopic visualization is used. In some embodiments, one or more of the tether ends could have enlarged portions, for example, crimped metal tips or tabs to better facilitate gripping of the ends.

Other tether configurations that may be used include passive and active variable length or bias structures such as braided or woven structures, electropolymers, springs, coils, magnets or solenoids. Thus, in some of the embodiments, the tether configuration may actively change in length in length or configuration resulting from the application of external energy or force such as electrical current or magnets. These active tether configurations may be further configured with local or distal sensor components that may modulate the activity of the external energy or force acting on the active tether. The modulation may be influenced by or triggered by detection of diaphragm movement or depolarization activity, nerve depolarization, pressure changes and/ mechanical contact in the airway.

The suture-receiving element, such as snare 108 can transform from a first open configuration when receiving the suture 105 to a second closed configuration to latch onto and move the suture 105, and also reversibly transform back to the first open configuration to release the suture 105. In some embodiments, the second closed configuration is a radially compressed configuration while constrained within the second elongate shaft 106 and the first open configuration is a radially expanded configuration, as illustrated in FIGS. 1A-1B, allowing the snare 108 to be moved axially forward as well as retracted with respect to the shaft 106. This can be accomplished, for example, by pushing the proximal handle 109 of the snare 108 in a distal direction. The proximal handle 109 may also be spring-loaded to actuate the snare 108 between a compressed and expanded configuration. In some embodiments, the proximal section of the snare opening is designed with a fairly wide angle of opening in order to provide quick collapse of the snare when pulled back into the elongated shaft. In some embodiments, the distal end of the snare opening is designed with a narrow slot that can capture the suture even in its radially expanded configuration or with the snare only partially compressed within the elongate shaft. The snare opening can have, in some embodiments a length of between about 0.3 cm to about 3.0 cm and width dimensions between about 0.2 cm to about 1.5 cm, such as between about 0.3 cm to about 1.0 cm in length and between about 0.2 cm to 0.5 cm in width.

The distal end of the snare 108 can have, in some embodiments, lateral struts 112 surrounding a central aperture 114 configured to receive suture 105 from the flexible needle 104. The snare 108 could be arcuate, rhomboid, square, triangular, or another appropriate shape. In other embodiments, the snare 108 may have movable jaws, pincers, or another mechanism to receive the suture 105 from the suture-passing element 104, or a window element as described in connection with FIGS. 5F-5I below. Further, the snare 108 can in one embodiment include a slotted pathway formed at a distal end of the aperture 114 to better capture and secure the suture 105 from the suture passing element 104.

Actuation of the proximal handle 109, such as proximal retraction by a physician will cause the snare 108 to retract back into the second elongate shaft 106, which can secure the suture 105 between lateral struts 112 of the snare 108 as the snare 108 transforms back to the first radially compressed configuration within the second elongate shaft 106. In some embodiments, the snare 108 can include mesh, webbing, or another material that can improve suture capture. The snare 108 may be formed by laser cutting a single piece of metal such as Nitinol, Elgiloy, or stainless steel, for example, or alternatively by forming a wire structure into a desired configuration. Other non-metallic materials such as nylon, polypropylene, or another polymeric material, for example, could also be used to form the snare 108. The snare 108 can include a sharpened distal tip to alternatively facilitate tissue penetration, or have a blunt tip in other embodiments. This and other embodiments of suture passers can be particularly advantageous, in certain cases, for use in creating a suture loop while the operative components of the suture passers are entirely within the tissue. In the case of tongue suspension, a blunt tip on the snare or elongated snare shaft and on the elongated needle shaft allows the distal end of suture passer to be located against the interior surface of the posterior mucosa of the tongue base. This provides for the deepest possible suture loop within the genioglossus and thus places the implanted suture closest to the tissues directly associated with the collapse of the tongue base against the posterior wall of the pharynx. The single shaft embodiments of the suture passer are additionally advantageous for use in tongue suspension as the anterior lateral neurovascular bundles of the tongue may easily be avoided with a single insertion point.

Figure 2:
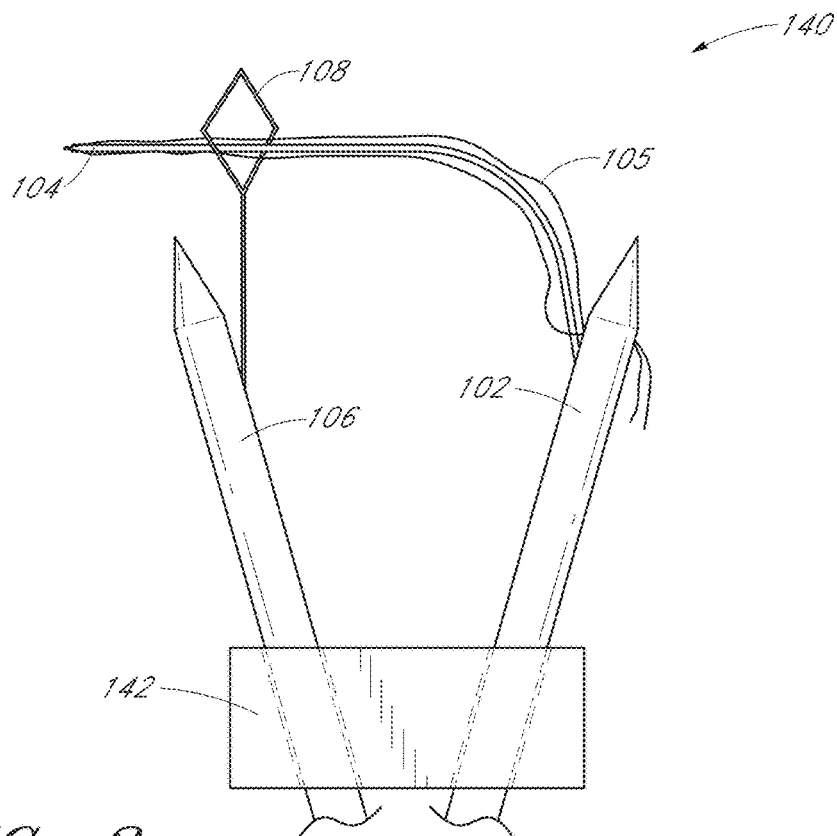
FIG. 2 illustrates another embodiment of a suture passer system with angle, depth, and orientation control.

FIG. 2 illustrates another embodiment of a suture passer 140 similar to that previously described in connection with FIGS. 1A-1C, except the suture passer 140 has a proximal angle control element 142, such as, for example, a releasably locking pivot or ratchet to adjustably control the angle, depth, and orientation between the first elongate shaft 102 and the second elongate shaft 106 depending on the desired tissue suspension. In one embodiment, the angle can be between 1-180 degrees, such as between about 1-90 degrees, or 30-60 degrees in some embodiments, in order to capture the desired amount of tissue.

Figure 3:
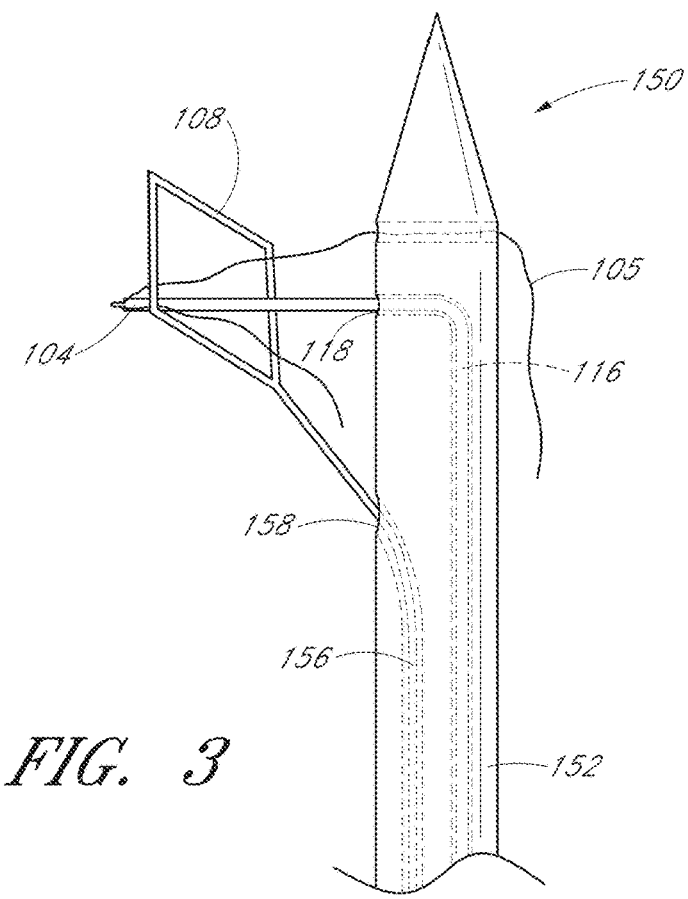
FIG. 3 illustrates another embodiment of a suture passer system with a single shaft.

FIG. 3 illustrates another embodiment of a suture passer 150 in which the suture-passing element 104 (e.g., a needle) and the suture receiving element 108 (e.g., a snare) are both housed within a single common elongate shaft 152. As illustrated below, controlling the angle and distance between the needle 104 and the snare 108 can impact the amount of tissue that can be captured, depending on the desired clinical result. In this embodiment, the snare 108 is housed within a lumen 156 that has an exit aperture 158 at the distal end of lumen 156. In some embodiments, the angle between the exposed part of the snare 108 and the long axis of the common elongate shaft 152 is between about 1-90 degrees, such as between about 15-60 degrees. The shaft of the snare 108 can be made of a shape memory material such as Nitinol or a polymer that bends at an angle in its unstressed shape once removed from the second elongate shaft 106.

Figure 4A:
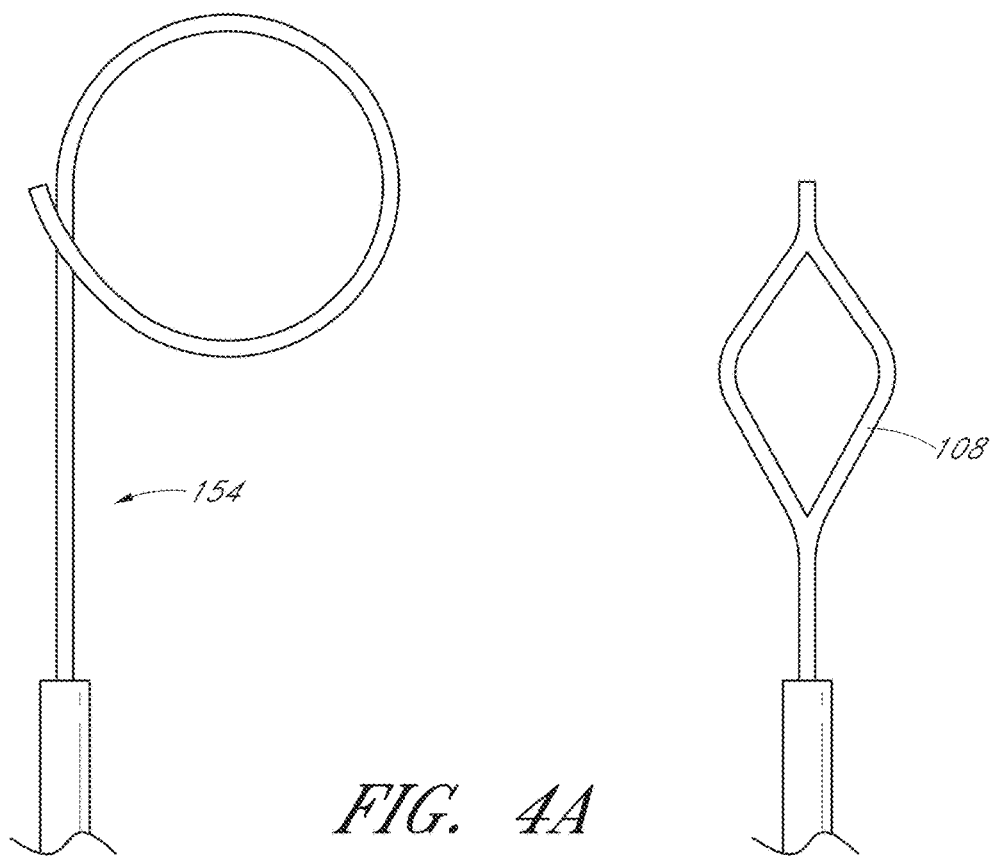
FIGS. 4A-4B illustrate another embodiment of a suture passer system with a suture-passing needle having a 270-360 degree arc.
Figure 4B:
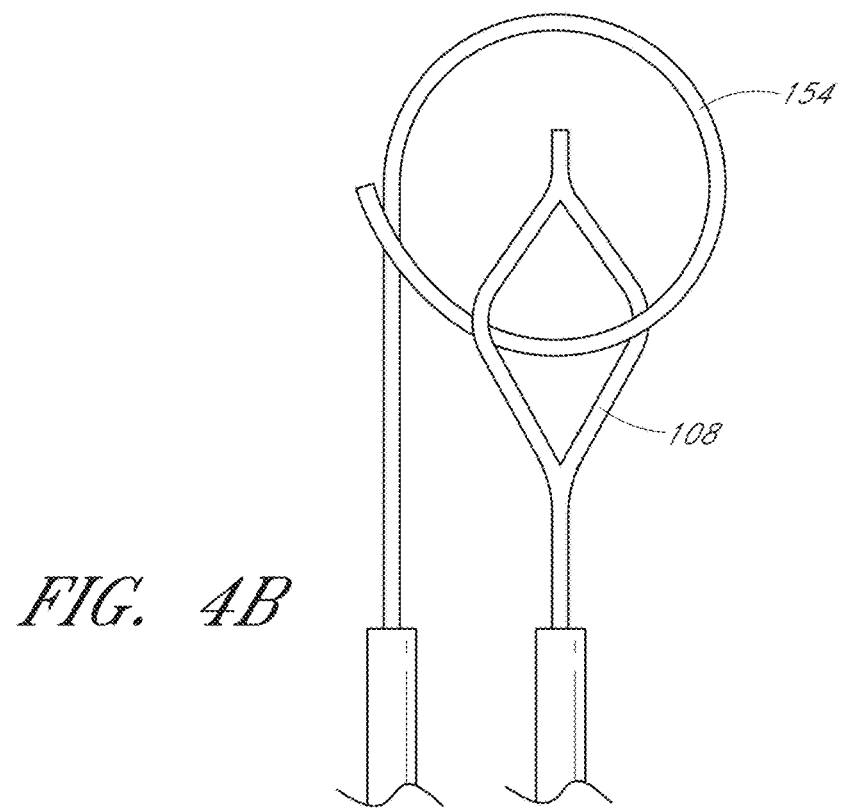

FIG. 4A illustrates an alternative embodiment of a flexible needle 154 with a distal end having an arc of between about 270 and 360 degrees while in its unstressed state. Upon being advanced distally from the exit aperture 118 of the elongate shaft, the needle 154 will pass through the aforementioned arc and through the snare while carrying the suture 105, allowing the snare 108 to better capture the suture 105, as illustrated in FIG. 4B. In some embodiments, the flexible needle 154 has an arc having a diameter of between about 0.5 cm and 5 cm, such as between about 0.5 cm and 2.5 cm. For increased support of the needle making a 270 to 360 degree tissue pass, an additional needle guide may be deflected/directed from the elongated needle shaft that supports the needle up through 90 degrees of the intended suture pass Methods of using the suture passer system will now be described. The suture passer advantageously allows for a loop of suture to be passed deep through the tissue without requiring passage through both surfaces of the tissue, where the depth of suture penetration is greater than the lateral distance of suture penetration.

Figure 5A:
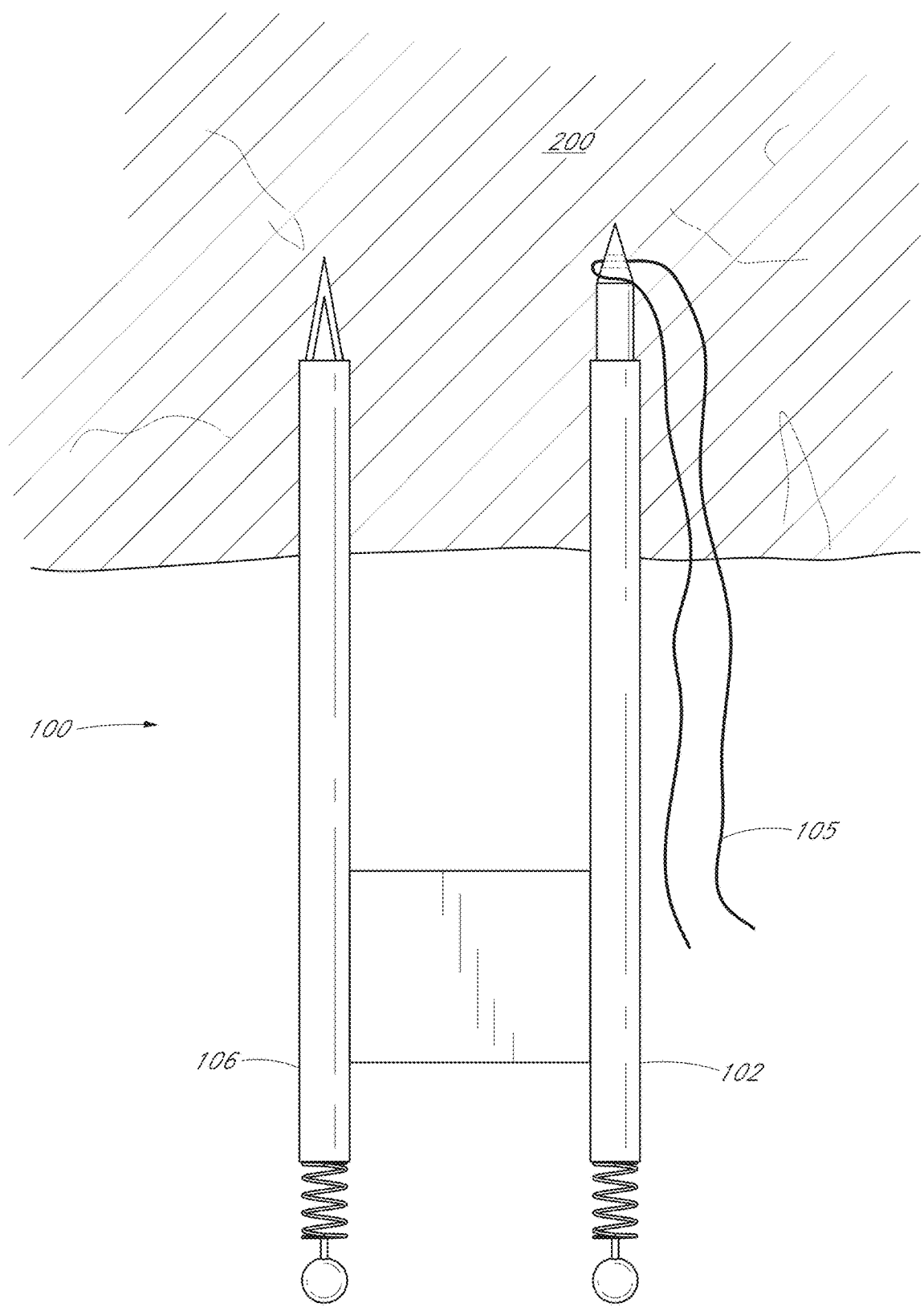
FIGS. 5A-5E illustrate a method of using one embodiment of a suture passer system.

In one embodiment, as illustrated in FIGS. 5A-5E below, the method involves advancing the suture passer system 100, including the first elongate shaft 102 housing the flexible needle 104 and the suture 105 and the second elongate shaft 106 housing the snare 108 (or alternatively a single elongate shaft 152 as described above) through the tissue 200 to be treated, e.g., the genioglossus muscle of the tongue as illustrated in FIG. 5A.

Figure 5B:
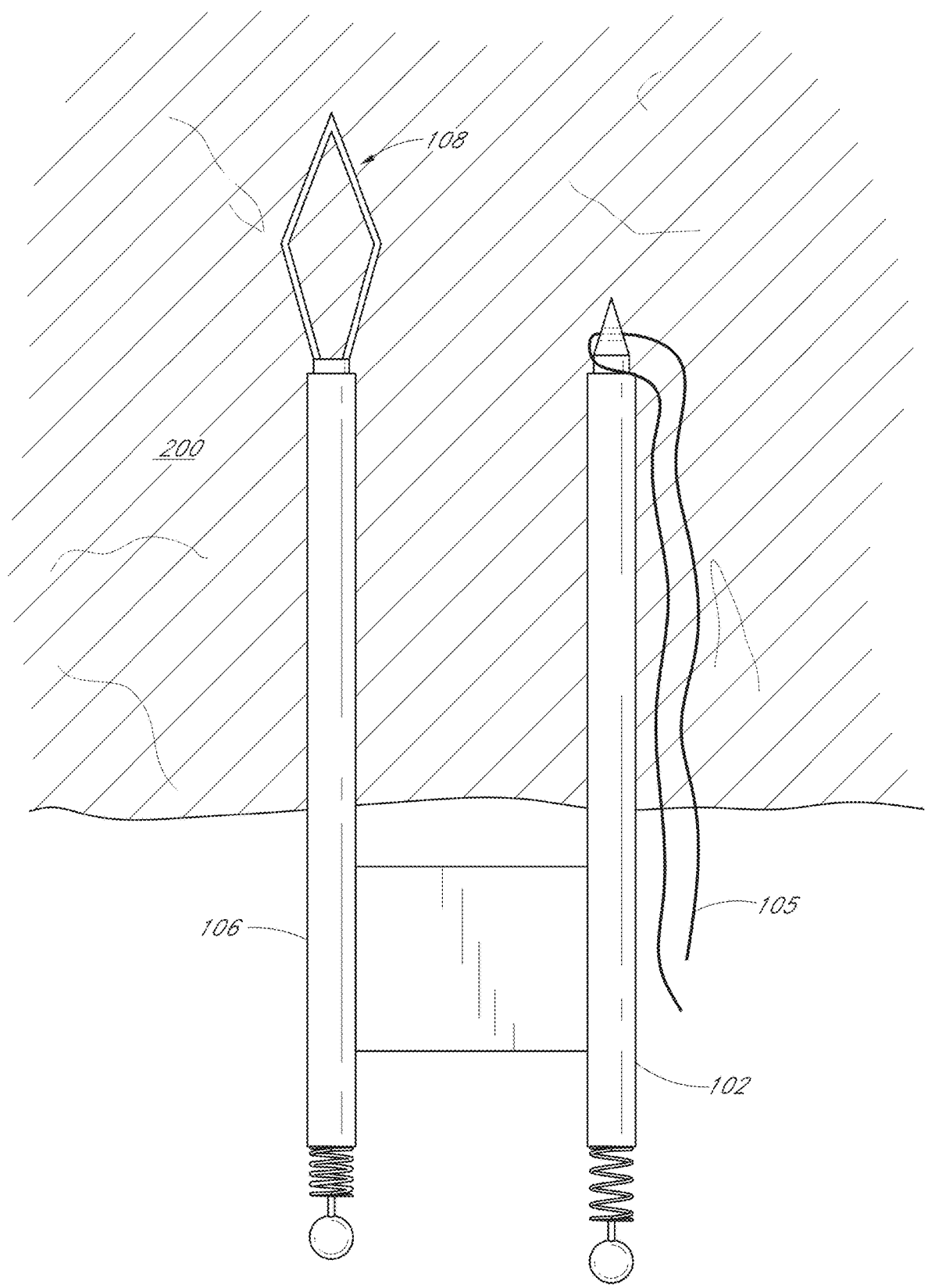

The snare 108 is then advanced out of the second elongate shaft 106 and transformed into a radially expanded configuration, as illustrated in FIG. 5B. In some embodiments, the snare 108 may advance distally from the second elongate shaft 106 along an axis parallel to the long axis of the shaft 106, or extend at an angle as previously described.

Figure 5C:
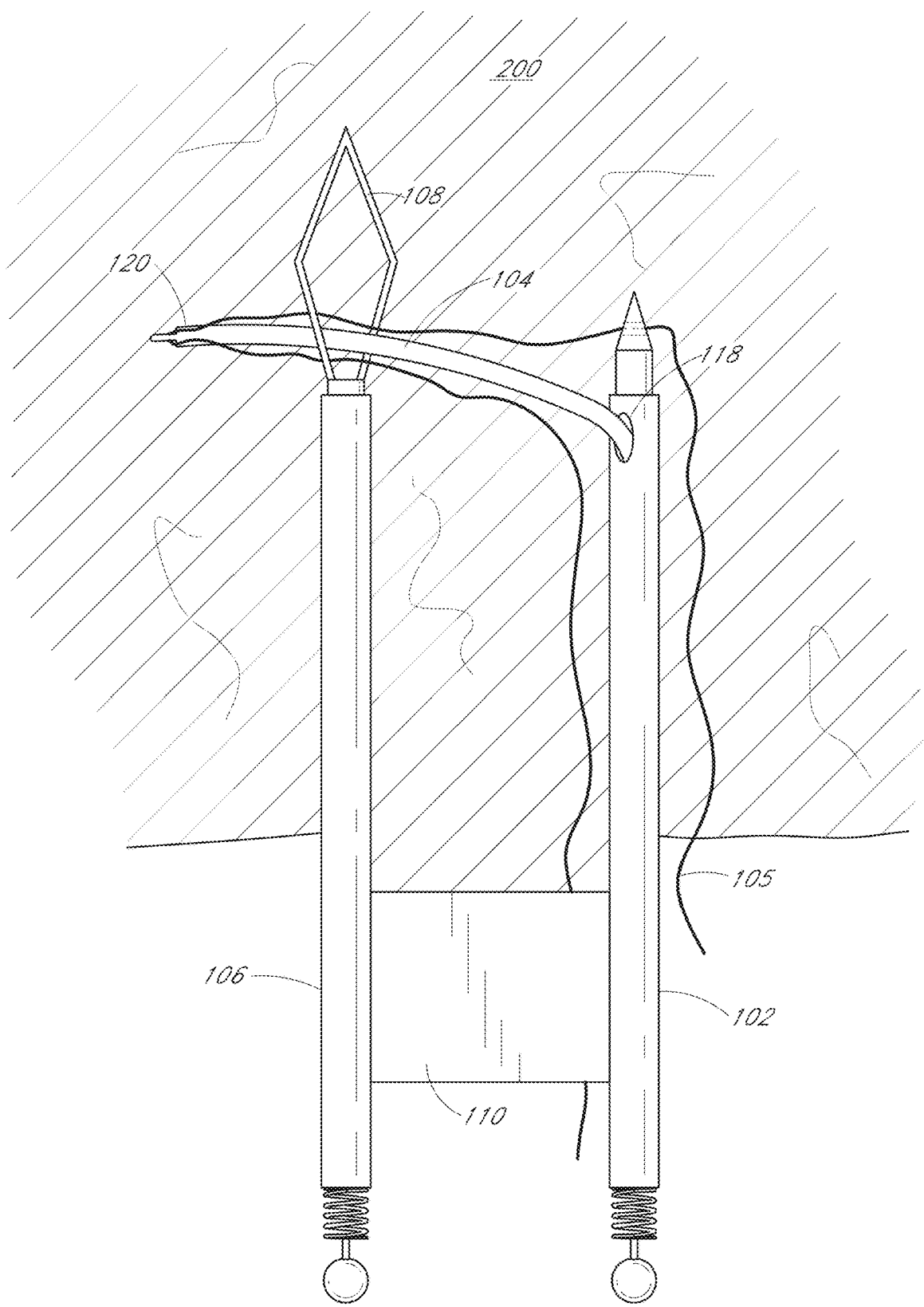

In FIG. 5C, the needle 104 then moves from a retracted position within the first elongate shaft 102 to an extended position. The distal end 120 of the flexible needle 104 holding the suture 105 is advanced through the exit aperture 118 of the first elongate shaft 102 such that it can be secured by the snare 108, as illustrated in FIG. 5C. Adjusting the angle and distance between the snare 108 and the needle 104 can impact how much tissue can be captured (as demonstrated by FIG. 2 and FIG. 3 above).

Figure 5D:
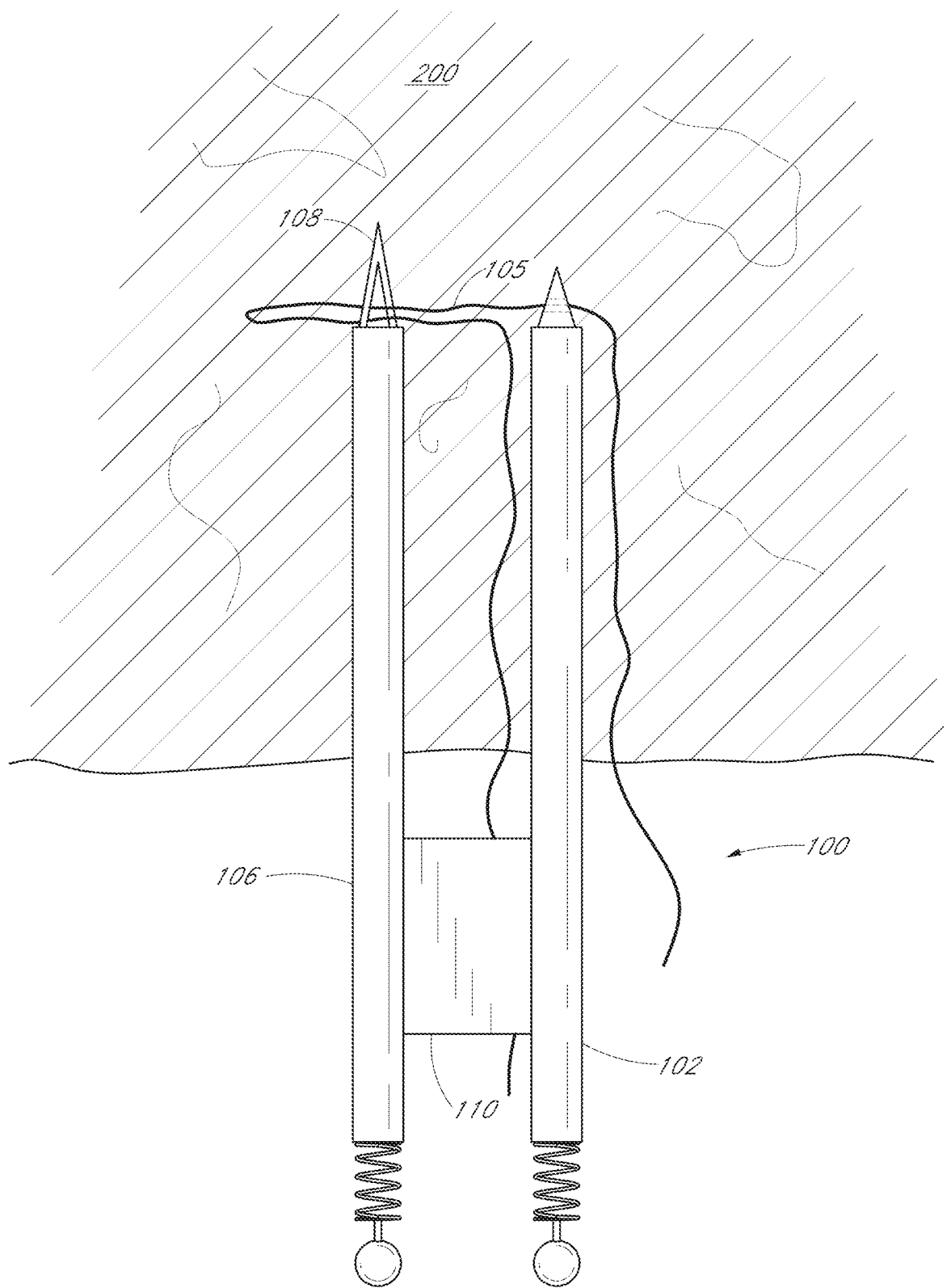
Figure 5E:
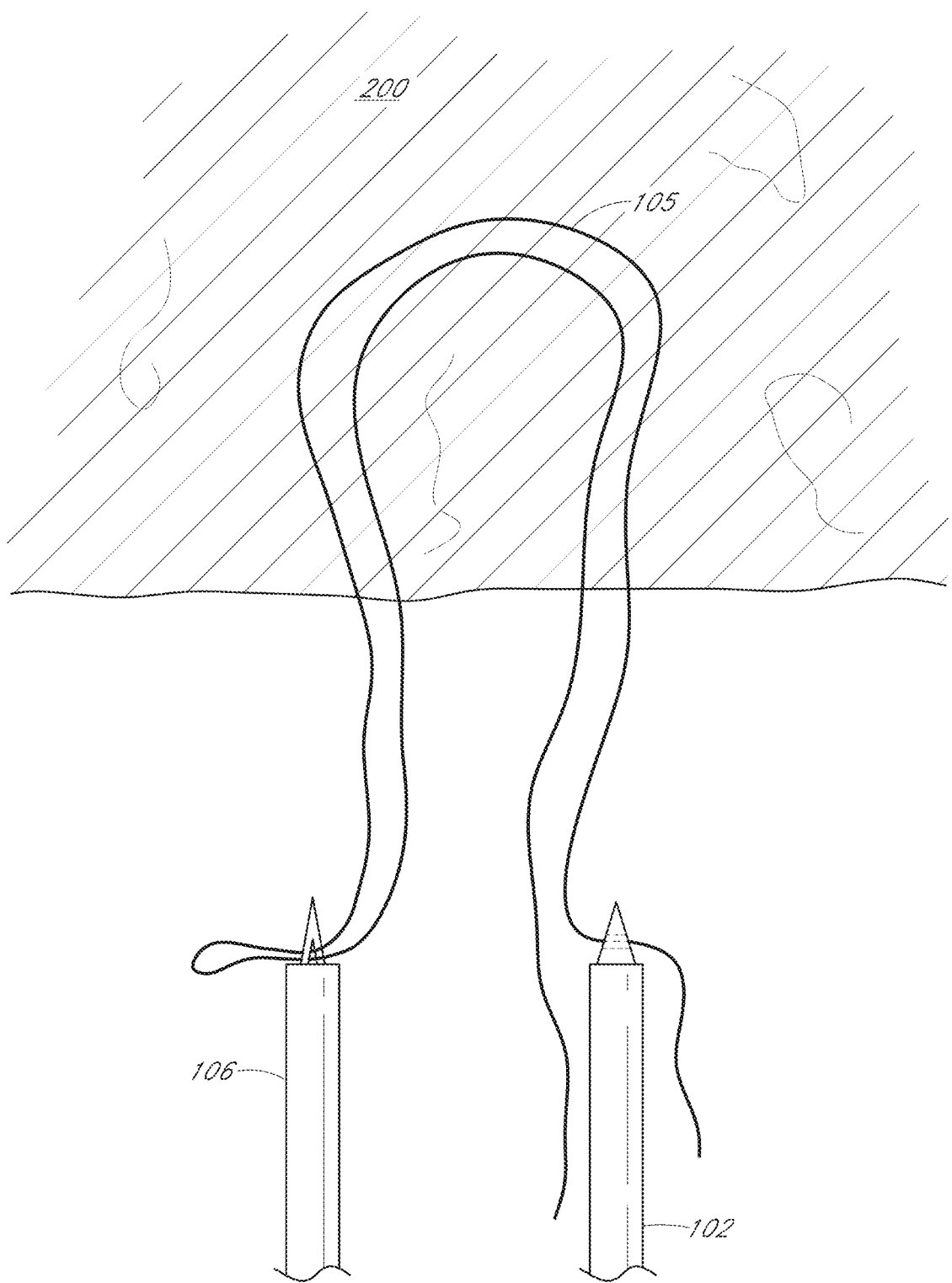

The needle 104 is retracted back into the first elongate shaft 102, leaving the suture 105 in operative placement with the snare 108 within the tissue 200. The snare 108 captures the suture 105 within the tissue 200 and then retracts back into the second elongate shaft 106. And then the suture passer 100 is withdrawn from the tissue 200, leaving the suture loop 105 behind in the tissue 200 as illustrated in FIG. 5D-5E. As the suture passer 100 is withdrawn, the suture passer 100 exits the same puncture site as it entered. The methods, and suture passers as described herein can advantageously pass suture while partially or completely within the tissue, and as such direct visualization is not required to accomplish the procedure in some embodiments. Furthermore, it is not required that any knots be tied within the tissue itself to form the suture loop. The free ends of the suture loop 105 can then be tied or otherwise secured outside the tissue 200 and tensioned, e.g., secured to a bone anchor or other body structure, in order to suspend the tissue 200. Various examples of adjustment mechanisms that can be utilized to adjust the tension of the one or more sutures are described and illustrated in connection with FIGS. 61A-K and 73-108 of U.S. Pat. Pub. No. 2008/0023012 to Dineen et al., which is hereby incorporated by reference in its entirety.

Alternatively, as illustrated in FIG. 5F, the suture-receiving element 108 may comprise an elongate shaft, such as a hypotube, having a capture window 122. In contrast to having a snare deploy from the shaft 106 as previously described, the illustrated embodiment provides a hypotube that can be flattened, with a window 122 defined by an aperture in the sidewall of the second elongate shaft 106 at or near the distal end of the shaft 106 and configured to receive the suture 105. In some embodiments, the size of the window 122 remains fixed. For example, the size of the window 122 may have a length of 0.2 cm to 1 cm and a width of about 0.2 cm to 0.7 cm in some embodiments. FIG. 5F also shows a movable panel 124 (e.g., a ribbon) within a lumen of the second elongate shaft 106 which may be configured to slide axially along pathways 126 in an appropriate direction, e.g., from a proximal end to a distal end of the hypotube and vice versa to close the window 122 and capture the suture 105, such as near location 122b. The panel 124 can be controlled by the physician via a control or handle at the proximal end of the second elongate shaft 106.

Figure 5G:
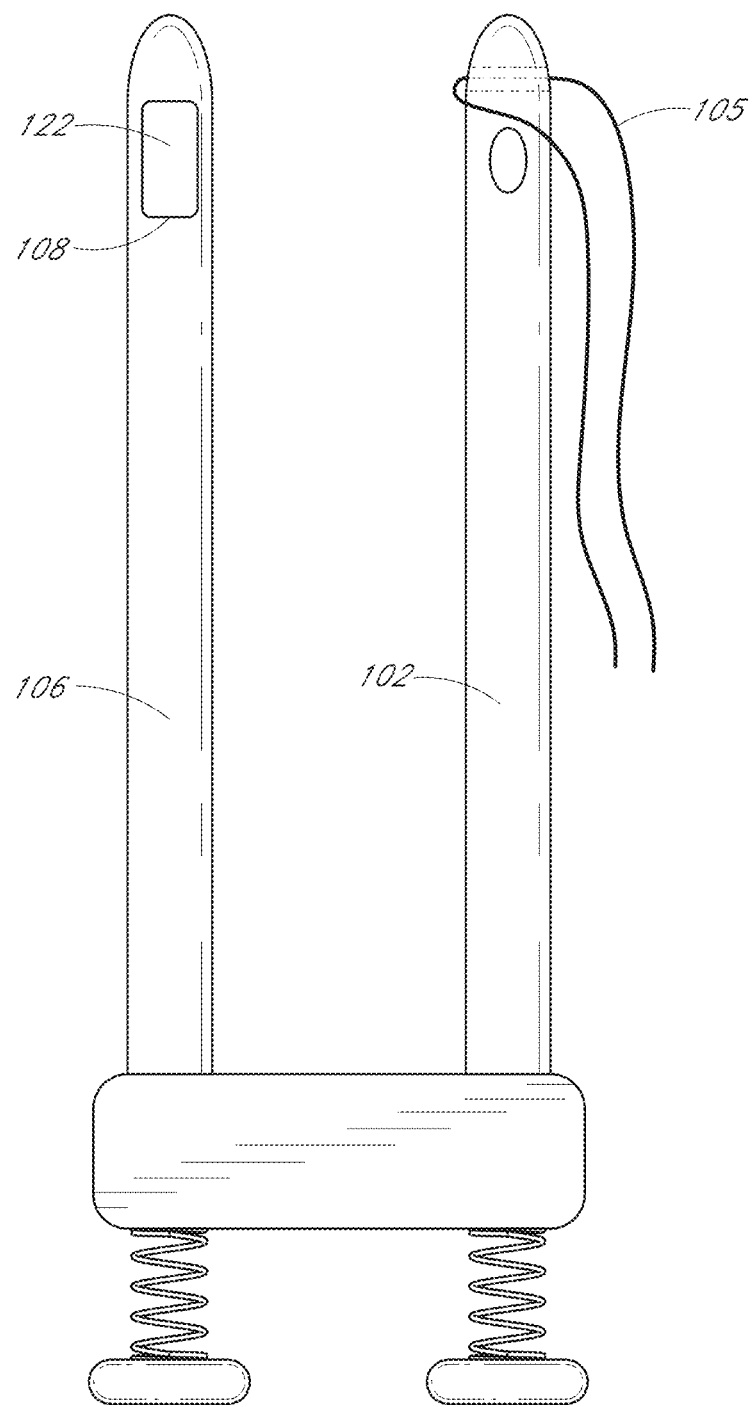
FIG. 5G-5I illustrates another method of using another embodiment of a suture passer system.
Figure 5H:
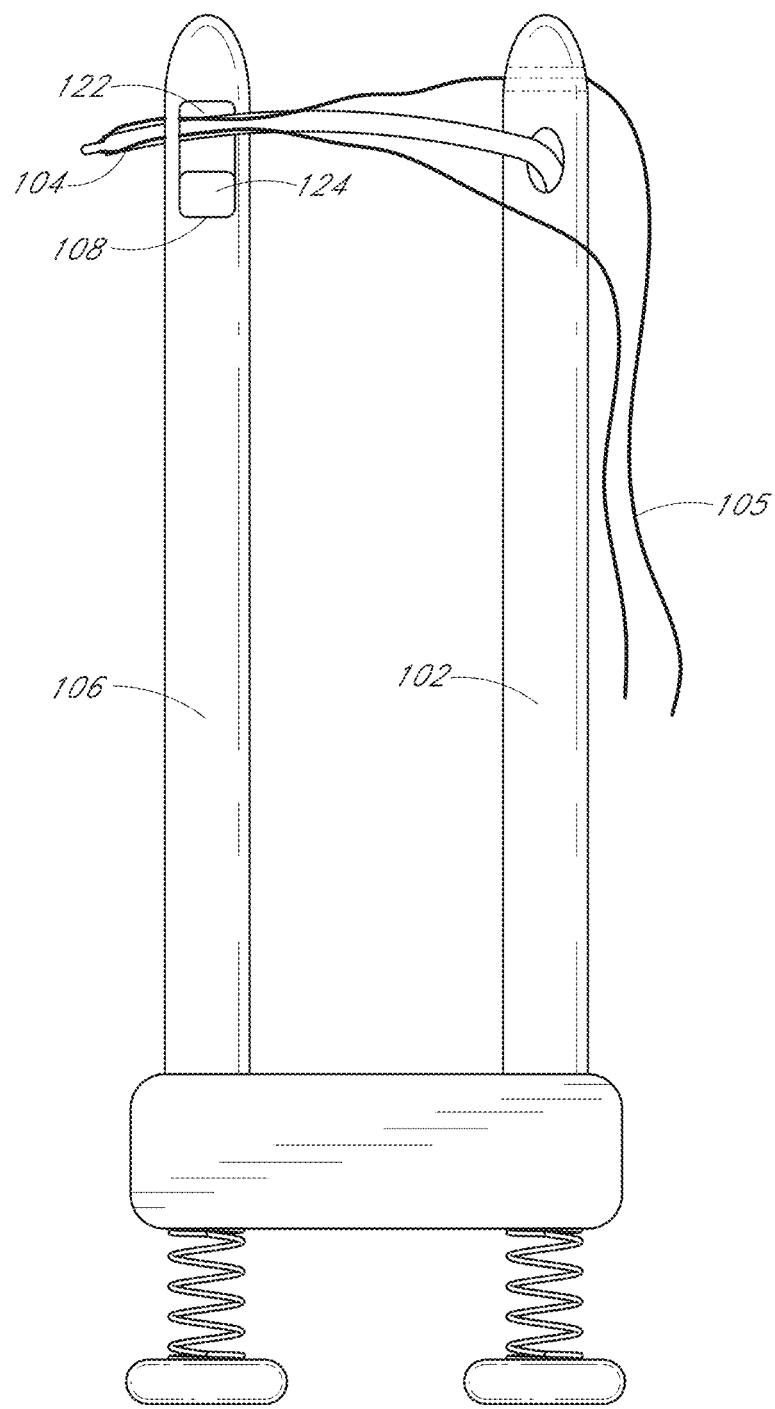
Figure 5I:
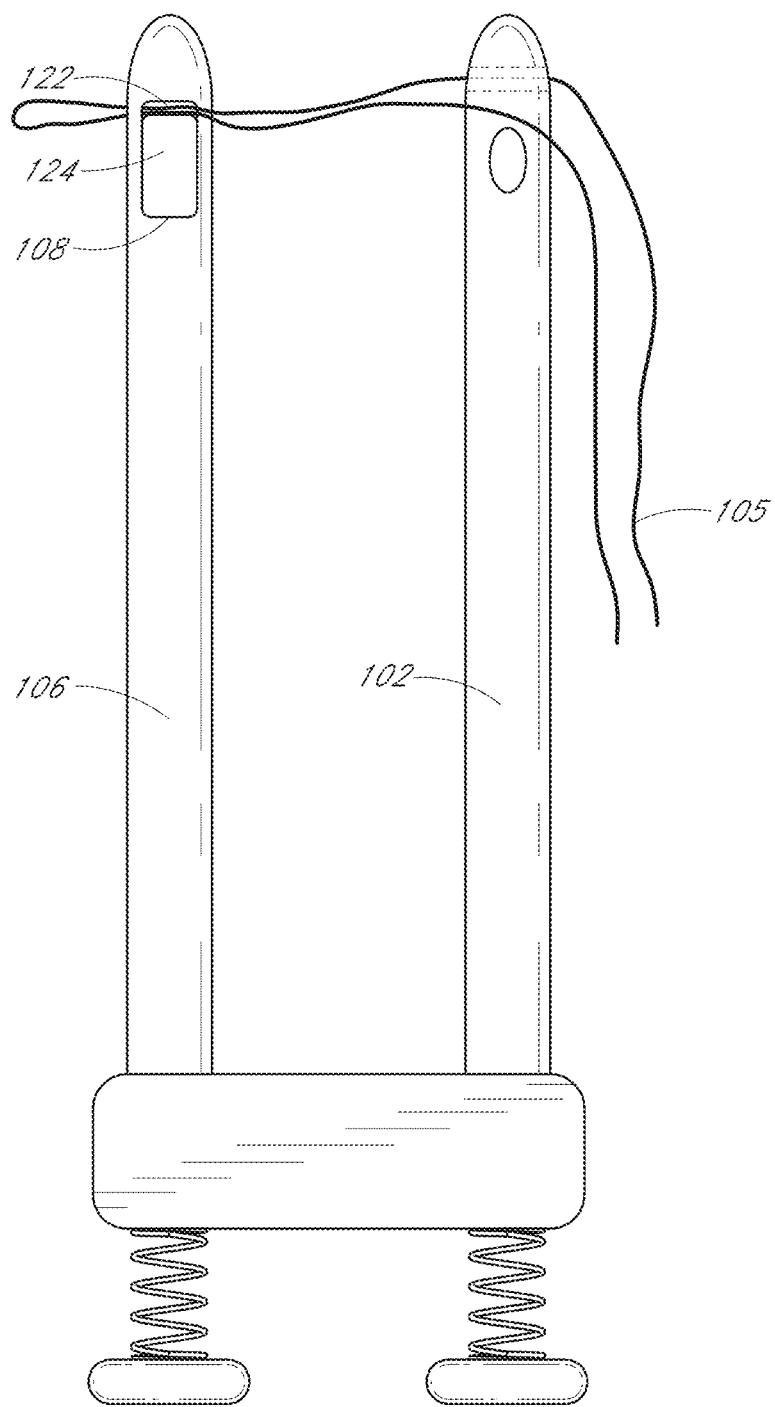

In FIGS. 5G-5I, a method of operating an embodiment of the suture passer 100 having a suture-receiving element 108 having a capture window 122 is shown. As illustrated in FIG. 5G, the suture passer 100 is advanced through the tissue 200 to the site to be treated. Next, shown in FIG. 5H, the flexible needle 104 carrying the suture 105 is advanced through the window 122 of the snare 108. Then, the flexible needle 104 is retracted back into the first elongate shaft 102, leaving the sutures 105 in the window 122. As illustrated in FIG. 5I, the sutures 105 are captured when the movable panel 124 slides against an end 122b of the window 122, closing the window 122. Then, the suture passer 100 is withdrawn to leave behind the suture loop 105 in the tissue 200. The method of operating the embodiment of the suture passer 100 described in FIGS. 5G-5I advantageously reduces the number of steps of passing the suture loop 105 because the snare 108 need not be separately deployed and retracted. Furthermore, because the flexible needle 104 can be repeatably advanced to the same position in the window 122, the first elongate shaft 102 and the second elongate shaft 106 can be the same length. Therefore, the method also advantageously provides passing a suture to a controlled tissue penetration depth and defines the offset from the tissue mucosa. The offset from the mucosa can be up to about 2.0 cm in some embodiments, such as up to 0.5 cm.

In some embodiments, a tissue could be suspended by replacing a first suture passed through the tongue with a second suture or other structure that substantially follows the path of the first suture by using the first suture to place the second suture or structure (such as an implant), such as, for example, operably connecting an end of the first suture to an end of the second suture/structure such that the second suture/structure is deployed within the tissue as the first suture is removed from the tissue. The first suture could be a "guide" suture with a width or diameter that is less than about 90%, 80%, 70%, 60%, 50%, 25%, or less of the second suture or structure, and thus serve as a dilator to avoid excessive trauma created by the tissue tract that could potentially be created if the second suture or structure was inserted without the guide suture. After the second suture or structure is deployed within the tissue, the connection with the first suture could be severed via, for example, untying a knot or cutting the link between the first suture and the second suture or structure.

Figure 6A:
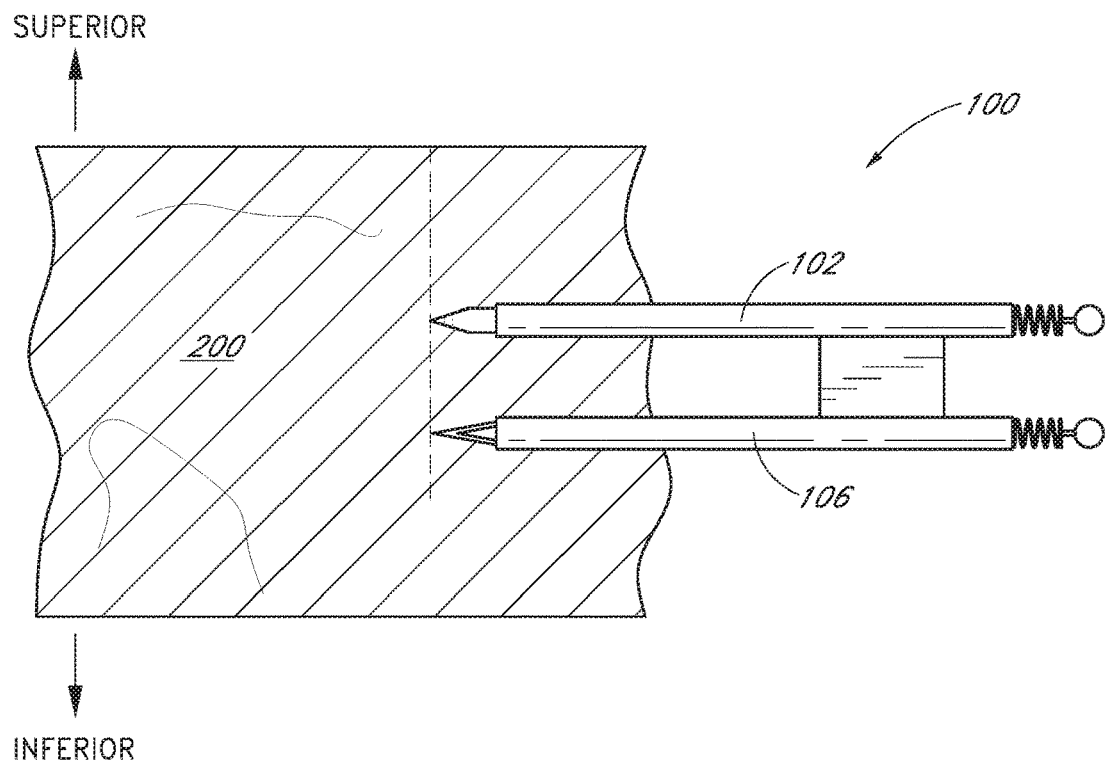
FIG. 6A illustrates a method of using one embodiment of a suture passer system to create a suture loop having a vertical orientation.

In some embodiments, as illustrated in FIG. 6A, the suture passer 100 can be inserted into the tissue 200 in a generally vertical orientation, that is, the straight-line distance between the distal tip of the first elongate shaft 102 and the distal tip of the second elongate shaft 106 falls along a generally superior-inferior axis.

Figure 6B:
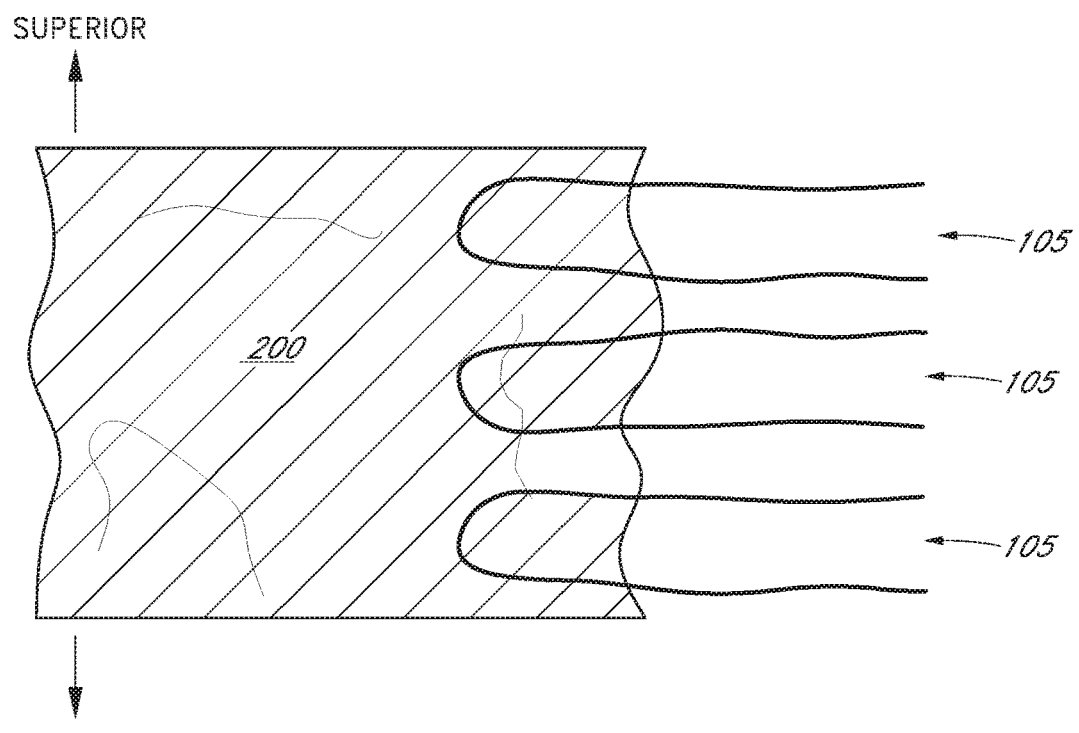
FIG. 6B illustrates a method of using one embodiment of a suture passer system to introduce serial spaced-apart or overlapping multiple suture loops into tissue.

In some embodiments, as illustrated in FIG. 6B, a plurality of vertically-oriented suture loops 105, such as at least 2, 3, 4, 5, 6, or more suture loops can be created in the tissue 200 by advancing the suture passer 100 in a generally vertical orientation as in FIG. 6A, and repeating the steps shown in FIGS. 5A-5E. In some embodiments, the suture loops 105 could be within about 10 degrees of the vertical axis. However, in other embodiments, the suture loops 105 could be within about 75, 60, 45, 40, 35, 30, 25, 20, or less degrees of the vertical axis. This provides more localized control of tissue suspension, depending on the desired clinical result. In some embodiments, a combination of horizontally-oriented and vertically-oriented suture loops can be used, or just horizontally-oriented suture loops. In some tongue embodiments, the distance between suture loops 105 could be irregular or regular. The distance between the midlines of the suture loops 105 could be, for example, between about 0.1 cm and about 3 cm. The multiple suture loops 105 may also have the same or differing orientations within the tissue 200. In some instances where additional suture strength is required at a single location within tissue, the multiple suture loops may share a midline axis, as illustrated in FIGS. 7A-7D, but have loops oriented differently (from −90 to +90 degrees) from the each other. FIG. 7A illustrates schematically a first suture pass 105a through tissue, while FIG. 7B illustrates both a first suture pass 105a and a second suture pass 105b sharing a common midline axis 105x. FIG. 7C illustrates an end view of FIG. 7B, while FIG. 7D illustrates a side view of FIG. 7B.

Substantially vertical suture loop(s) placed at the midline of the tongue base may have be additional advantageous as therapy for preventing an apnea event. First, by acting on the midline, the suture loop is less likely to affect the lateral walls of the pharynx. Second, if there is collapse of the tongue base against the posterior wall of the pharynx, the tissue may be "tented" at the midline, maintaining at least some pathway for air and avoiding complete obstruction of the pharynx. This is similar to the effect seen with a midline glossectomy.

Tissue 200 may be suspended by securing the free ends of suture loop(s) 105 to a structure such as a bone anchor (e.g., implanted in the mandible or hyoid bone) or other body structure outside the tissue 200. Other body structures in which the suture loop could be attached to include, for example, the hyoid bone or the soft palate. Alternatively, the free ends of suture may be tied in a knot or otherwise secured to suspend the tissue 200.

When tongue suspension is desired, the tongue could be accessed via the oral cavity. In some instances, embodiments of the tongue suspension system can be implanted through an antero-inferior access site of the mandible. Implantation of the system that avoids the transoral route may improve infection rates that occur with other tongue related devices and procedures.

Figure 7E:
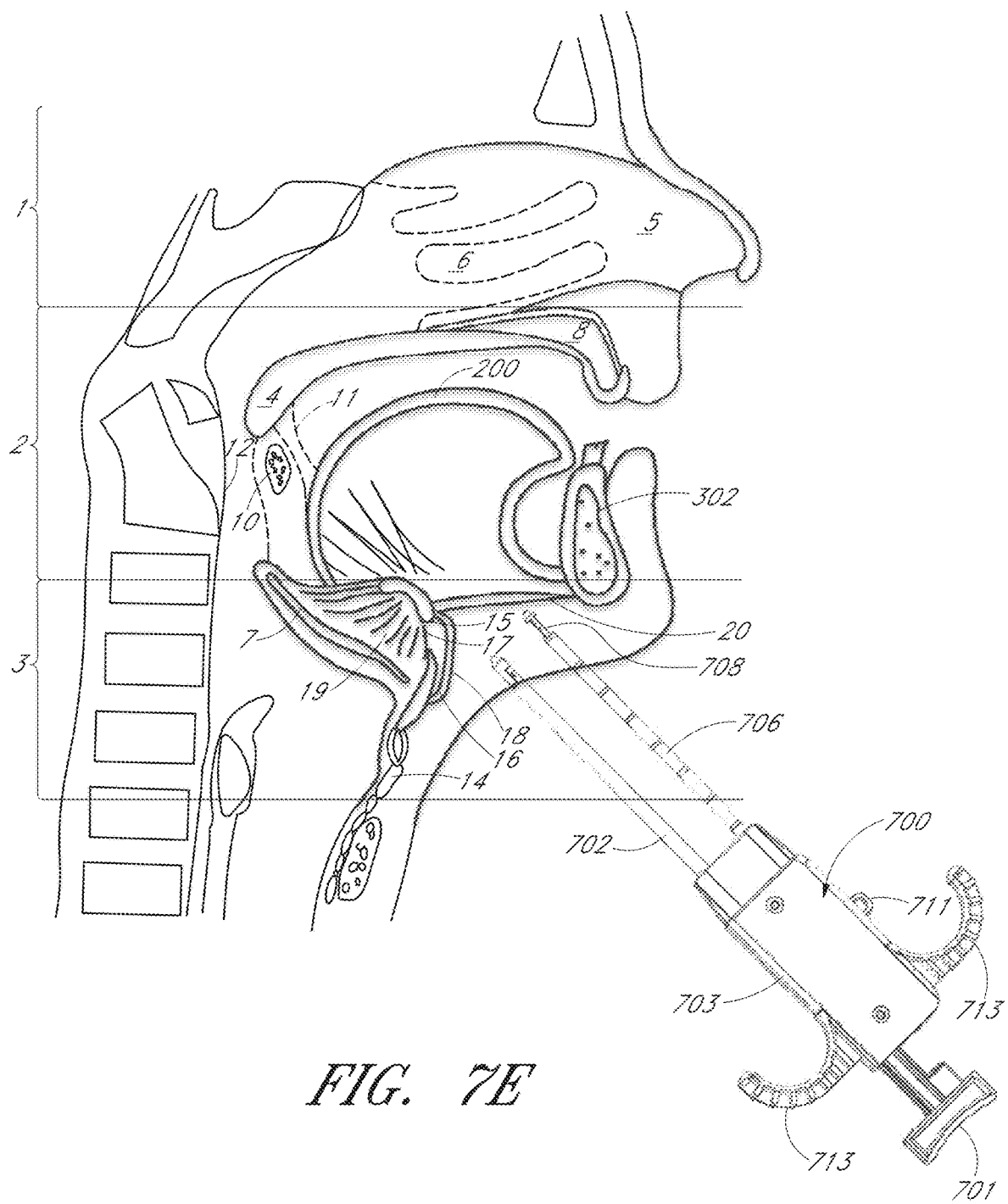
FIG. 7E illustrates a method of accessing the tongue with pharyngeal anatomy, according to one embodiment of the invention.

A description of pharyngeal anatomy and a method for suspending the tongue will now be described. FIG. 7E is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is a less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 200, tonsils 10, palatoglossal arch 11, the posterior pharyngeal wall 12 and the mandible 302. The mandible typically has a bone thickness of about 5 mm to about 10 mm anteriorly with similar thicknesses laterally. An obstruction in the oropharynx 2 may result when the tongue 200 is displaced posteriorly during sleep as a consequence of reduced muscle activity during REM sleep. The displaced tongue 200 may push the soft palate 4 posteriorly and may seal off the nasopharynx 1 from the oropharynx 2. The tongue 200 may also contact the posterior pharyngeal wall 12, which causes further airway obstruction.

The hypopharynx 3 comprises the region from the upper border of the epiglottis 7 to the inferior border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 200 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the infero-posterior aspect of the mandible 302 by the geniohyoid muscle 20.

Methods of treating a condition of an airway will now be described. For example, the method can comprise creating a first pathway within the tongue 200 without passing through the mucosa, and creating a second pathway within the tongue 200. For example, FIG. 7E depicts one embodiment of the invention where the suture passer 700 is inserted into the tongue 200 through an insertion site inferior to the mandible 302, which could be but is not necessarily about the anterior portion of the mandible 302. In other embodiments, the implantation pathway may originate from a location anterior or lateral to the mandible 302, and in still other embodiments, may also pass through the mandible 302. The suture passer 700 may be inserted percutaneously to create the first pathway and the second pathway. Prior to insertion of the suture passer 700, optionally a guide catheter, needle, or other piercing delivery tool known in the art could be initially placed, and followed by a guidewire. The method can further comprise passing a flexible elongate member (e.g., suture loop) extending through the first pathway through the tongue tissue from the first pathway to the second pathway. In some instances, the distal portion of the suture loop is positioned about the base of the tongue, which is the portion of the tongue posterior to the circumvallate papillae (not shown), but other locations within the tongue 200, such as the anterior portion 39, may also be used. For example, the loop portion of the suture loop may also be positioned in the dorsal region 38 of the tongue 200. When the suture loop is withdrawn from the second pathway, the suture loop forms a looped path through the tongue 200.

In FIG. 7E, the embodiment of the suture passer 700 can have a dual-shaft configuration with a single actuator control 701 at a proximal end. The suture passer 700 also has a body 703 housing different mechanical components, including secondary control 711 along a sidewall of the body 703. Suture passer 700 may also include finger grips 713 extending from opposite sidewalls of the body 703. A first elongate shaft 702 and a second elongate shaft 706 extend distally from the body 703. Additional details of the embodiment of the suture passer 700 may be described with reference to FIGS. 25A-25E discussed later herein.

Figure 7F:
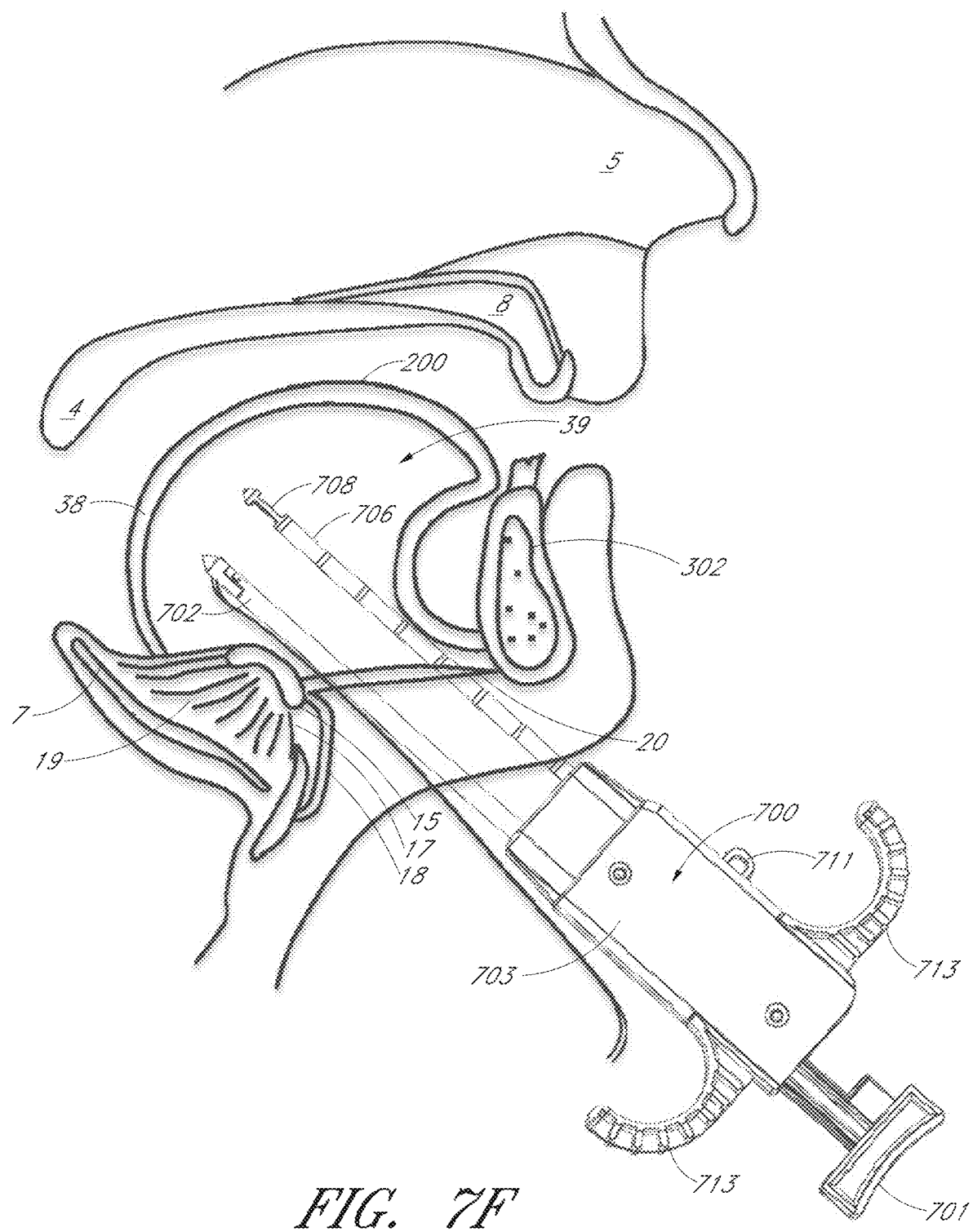
Figure 7G:
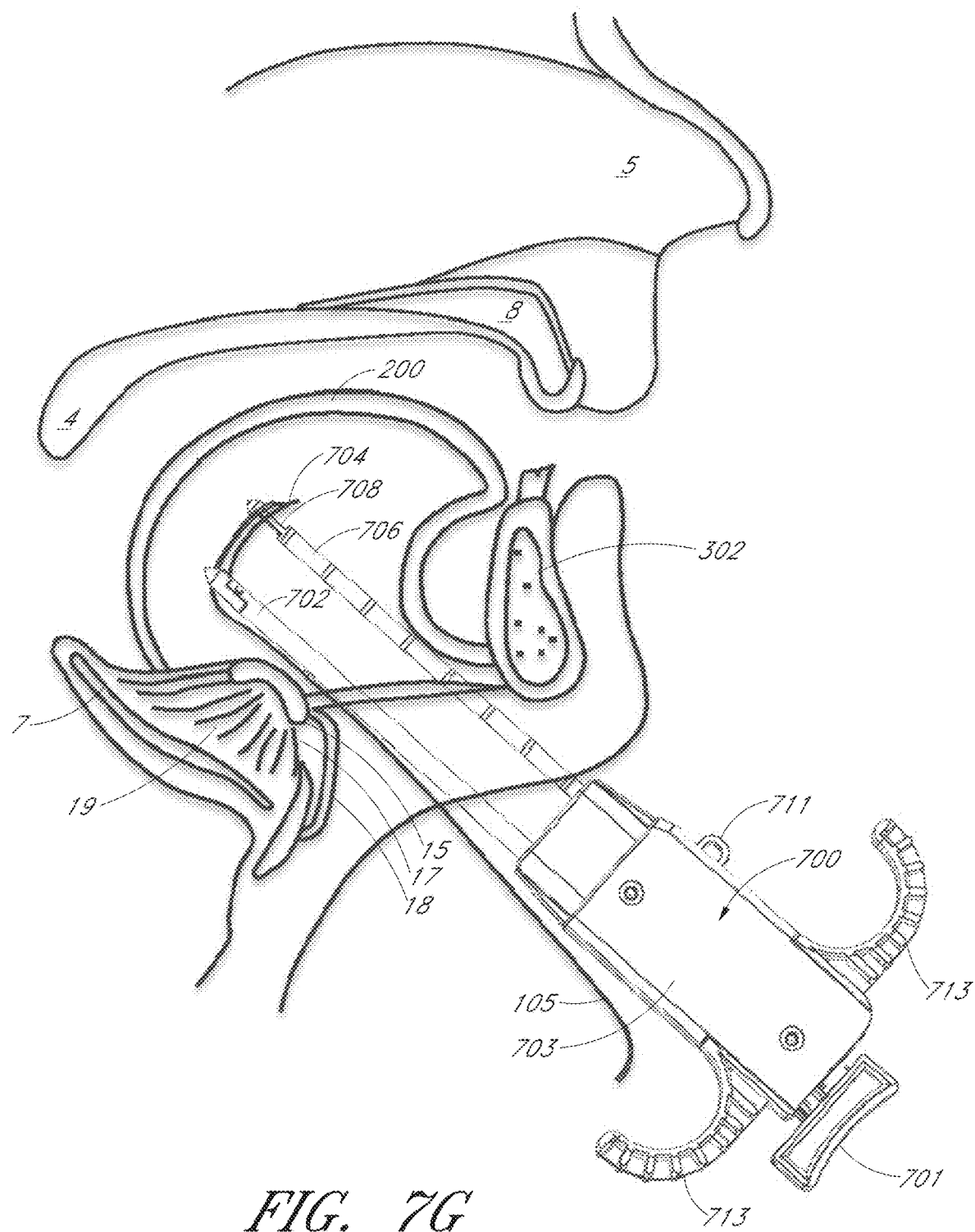
Figure 7H:
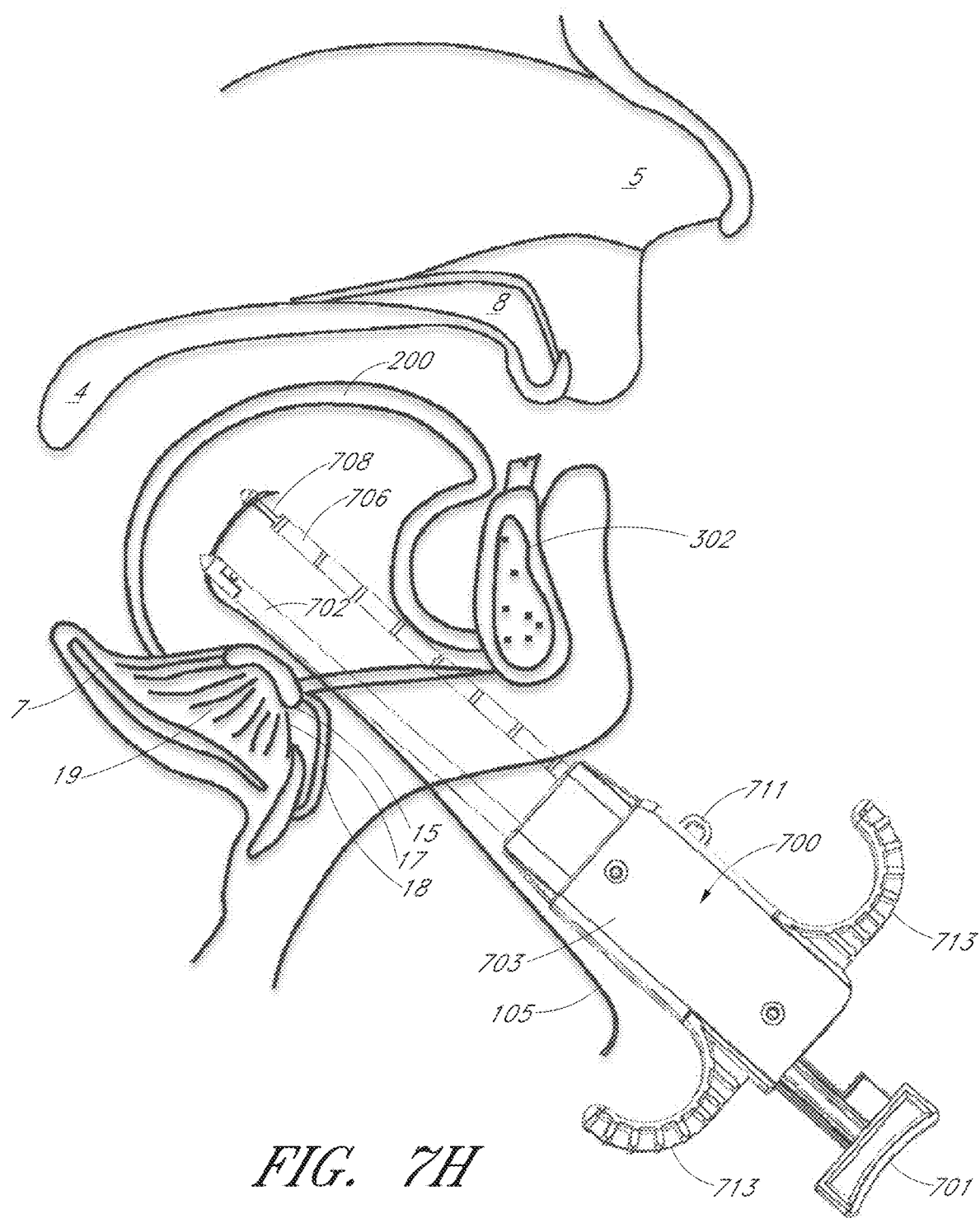
Figure 71:
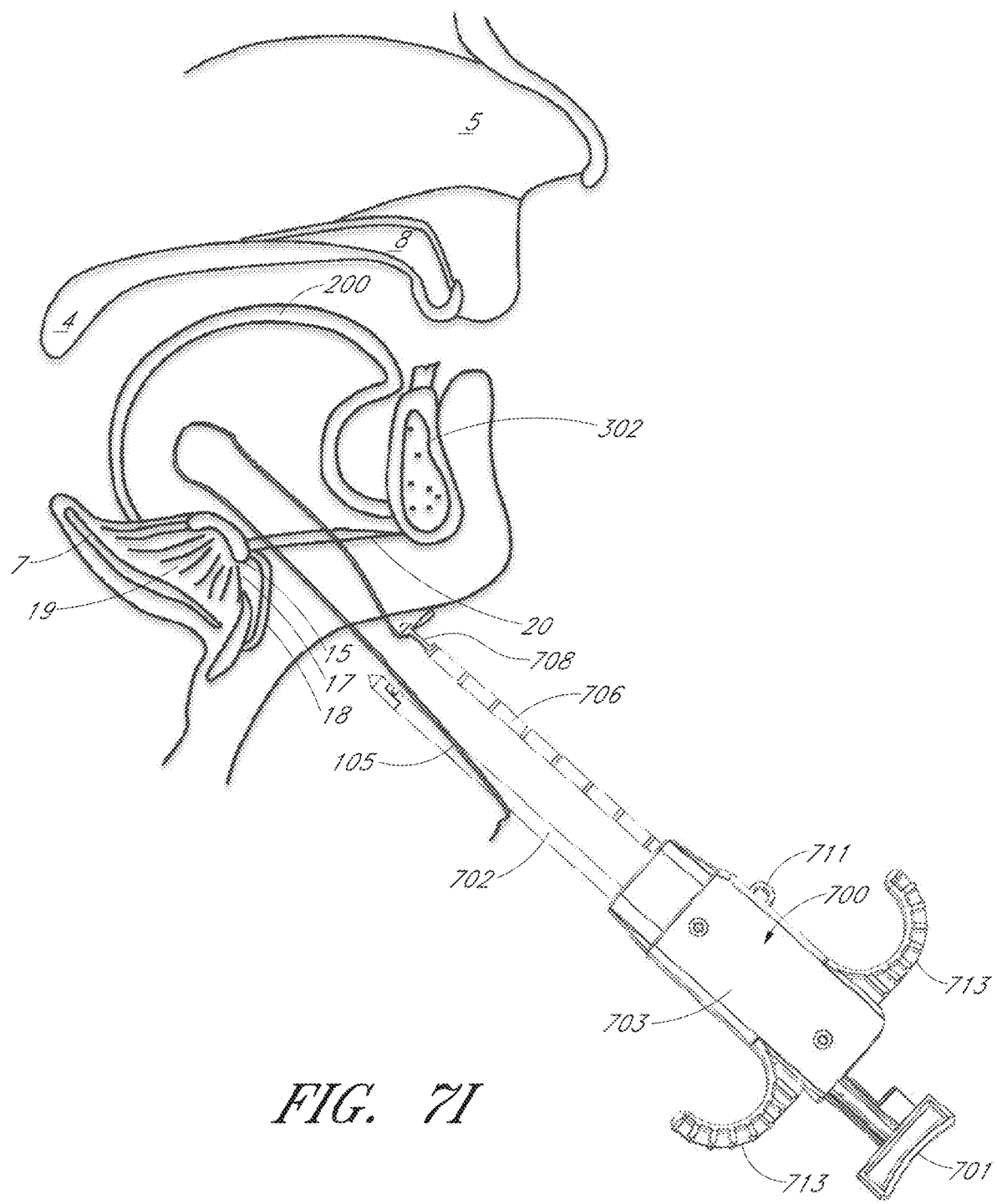
Figure 7J:
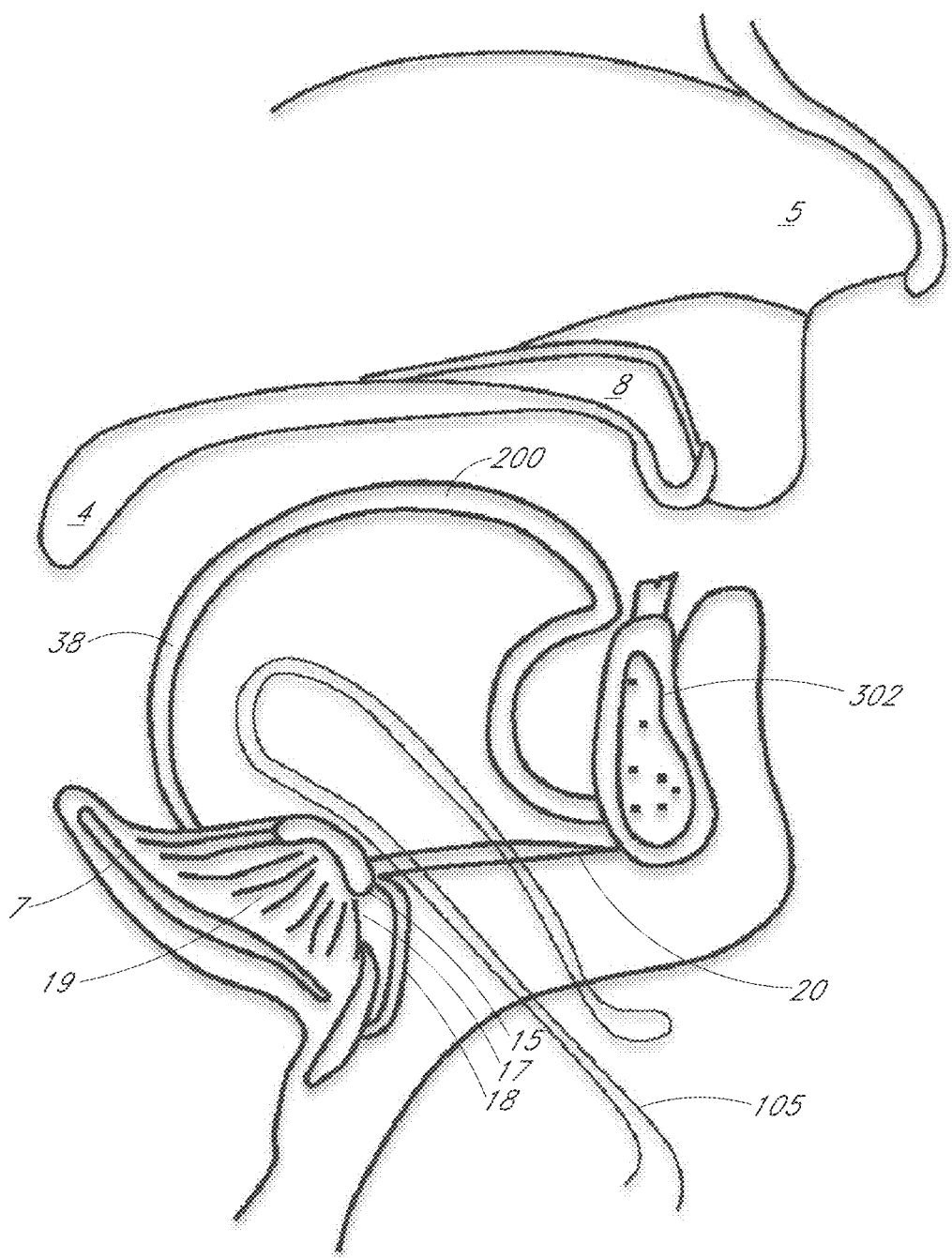
Figure 7K:
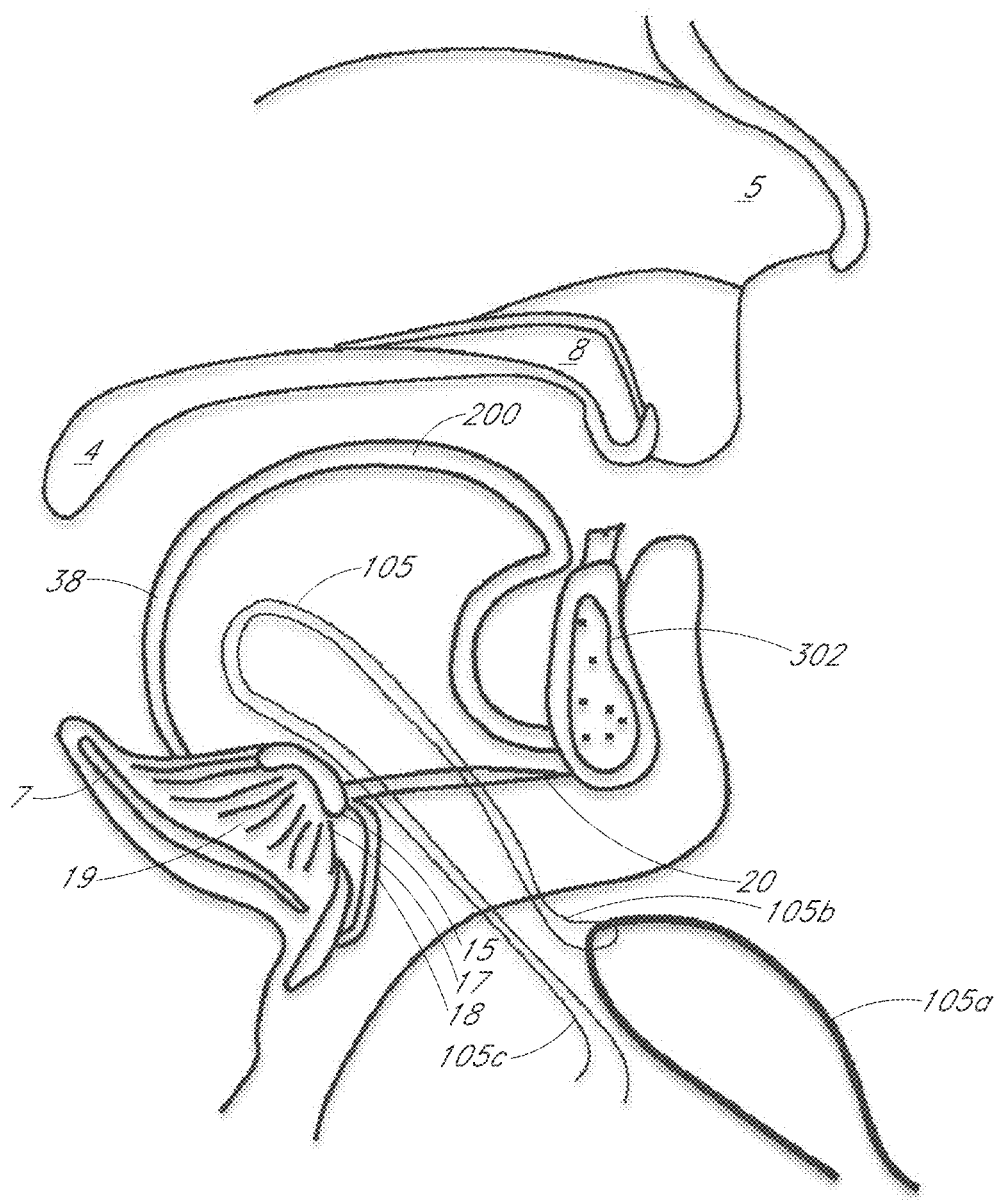
Figure 7L:
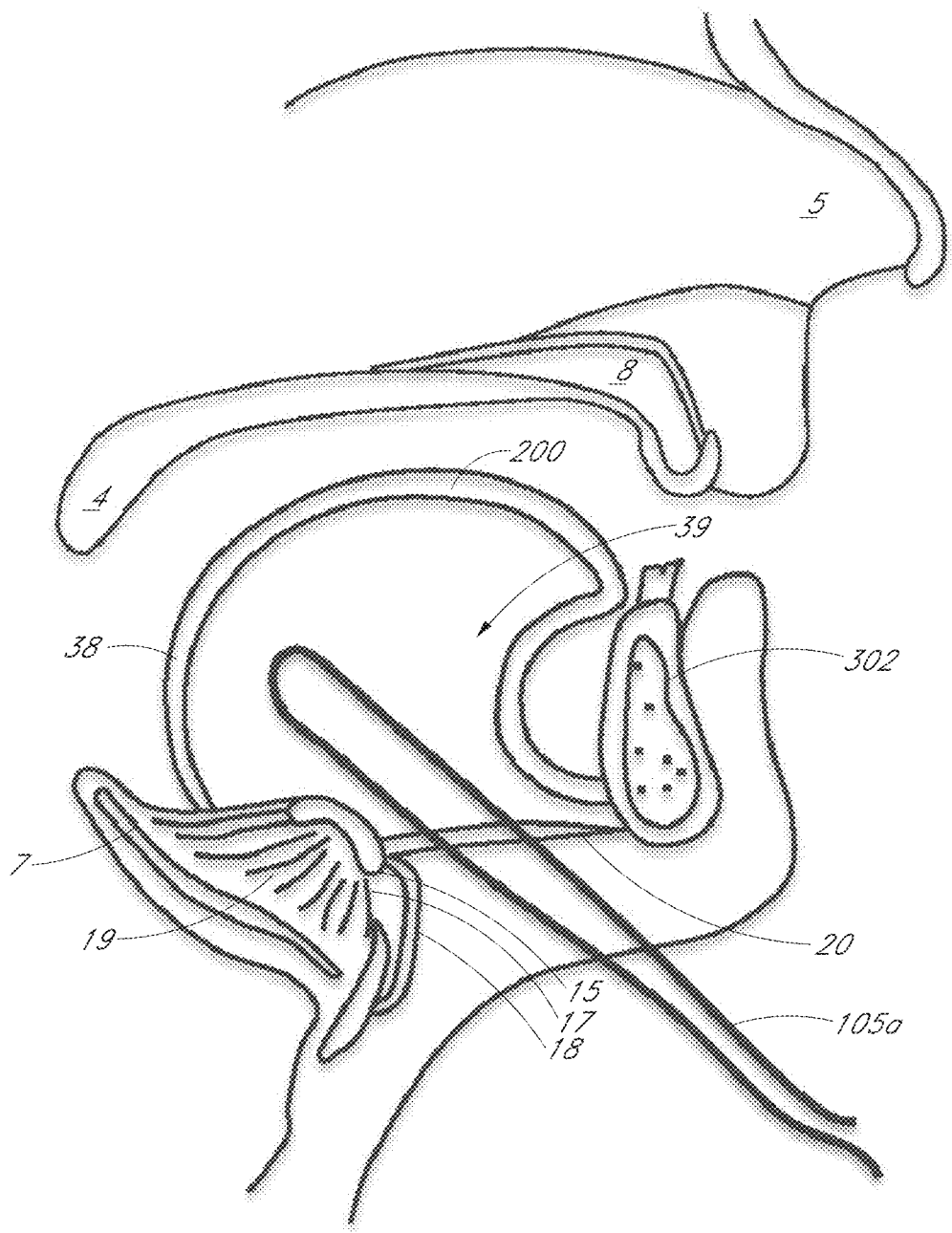
Figure 7M:
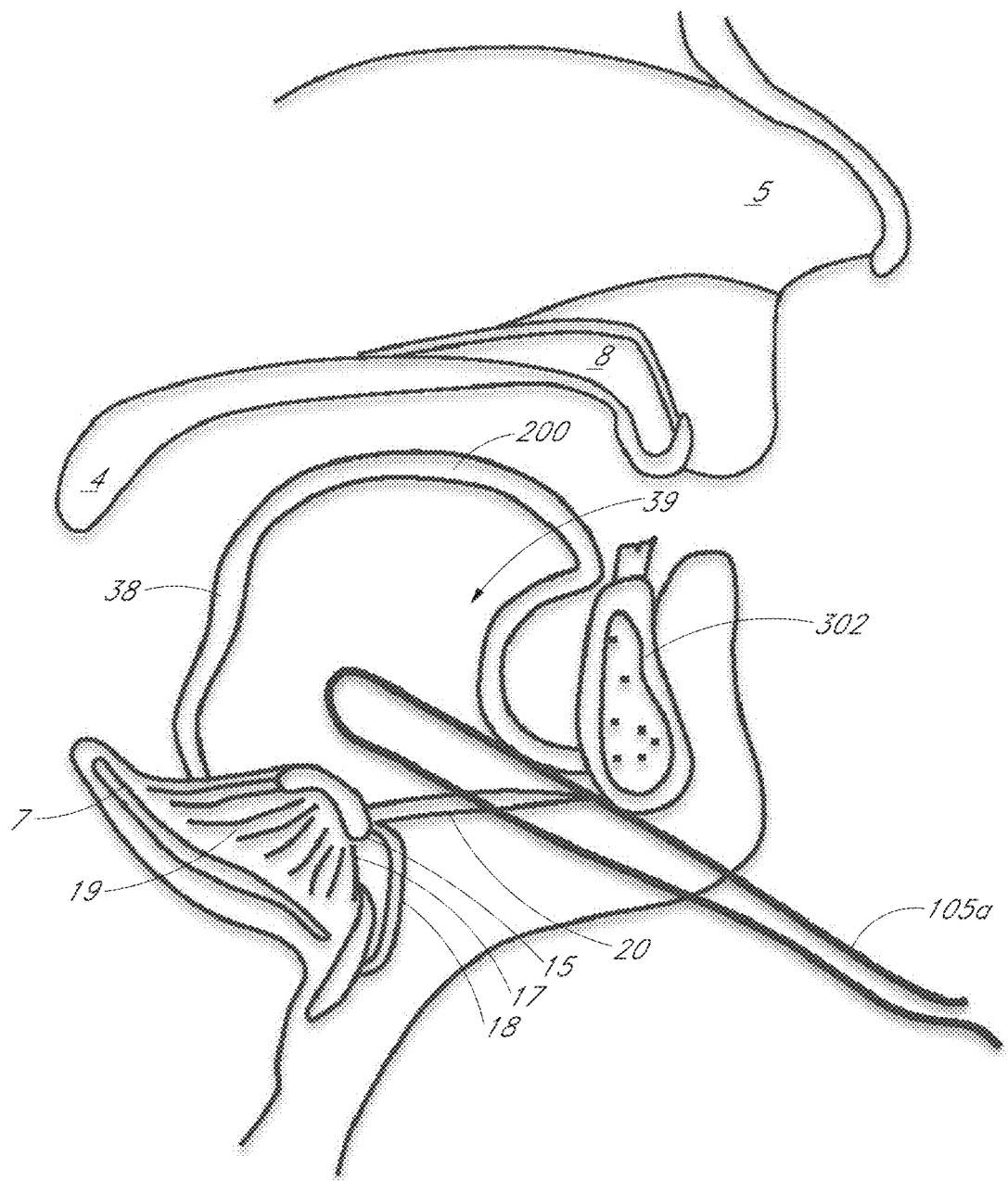

Steps as illustrated in FIGS. 7F-7J can be described in connection with FIGS. 5A-5E, which generically illustrate formation of a suture loop via use of a suture passer completely within the tissue 200. A suture 105 is passed through the base of the tongue 200 using, for example, a suture passer 700 or any other embodiment of a suture passer as described elsewhere herein. FIGS. 7F-7N show a procedure and sequential steps for anterior suspension of the tongue 200. As illustrated in FIG. 7F, the suture passer 700 is advanced distally into tissue of the base of the tongue 200 without passing through the tongue mucosa. The suture passer 700 can be inserted into the tongue 200 at an angle to the superior-inferior axis. The first elongate shaft 702 may be positioned inferiorly relative to the second elongate shaft 706 as the suture passer 700 is delivered distally into the base of the tongue 200. Next, shown in FIG. 7G, a flexible needle 704 carrying the suture 105 is advanced through a window of a suture-capturing element 708. As illustrated in FIG. 7H, the flexible needle 704 is retracted back into the first elongate shaft 702, leaving the suture 105 in the capture window, such as when a movable panel of the second elongate shaft 706 slides against an end of the window, closing the window. As shown in FIGS. 7I-7J, the suture passer 700 is withdrawn to leave behind the suture loop 105 in the tissue 200.

When suspending the tongue and advancing the genioglossus anteriorly, the precise placement and tensioning of an implant can avoid potentially increasing potential lateral collapse of the pharynx. Furthermore, tongue suspension using the methods and devices as disclosed herein can be advantageous as the procedure, in at least some embodiments, can be fully reversible by simply removing the suture(s).

In FIGS. 7K-7N, a method of inserting another structure or tension element, such as a suture within the tongue 200 is provided. Upon release of the suture 105 from the suture passer 100, the suture 105 may include a closed end 105b and free ends 105c. The suture 105a may pass through and be secured to the closed end 105b of the suture 105. When the suture 105 is pulled from the free ends 105c, the suture 105a is drawn into the tongue 200 and toward the dorsal region 38. The suture 105a positioned in the tongue 200 can add strength and greater tension, based at least in part on its size and/or material properties, so as to provide additional tissue control. In some embodiments, the suture 105a is a tension element that is thicker than the suture 105. Moreover, the first suture 105 can be a guide suture or a suture loop having a width that is less than 90%, 80%, 70%, 60%, 50%, or less of the tension element 105a. The tension element 105a can be advanced toward the anterior portion 39 to further suspend the tongue 200 and advance the genioglossus anteriorly. The tension element 105a can be secured via a bone anchor 300.

Figure 7N:
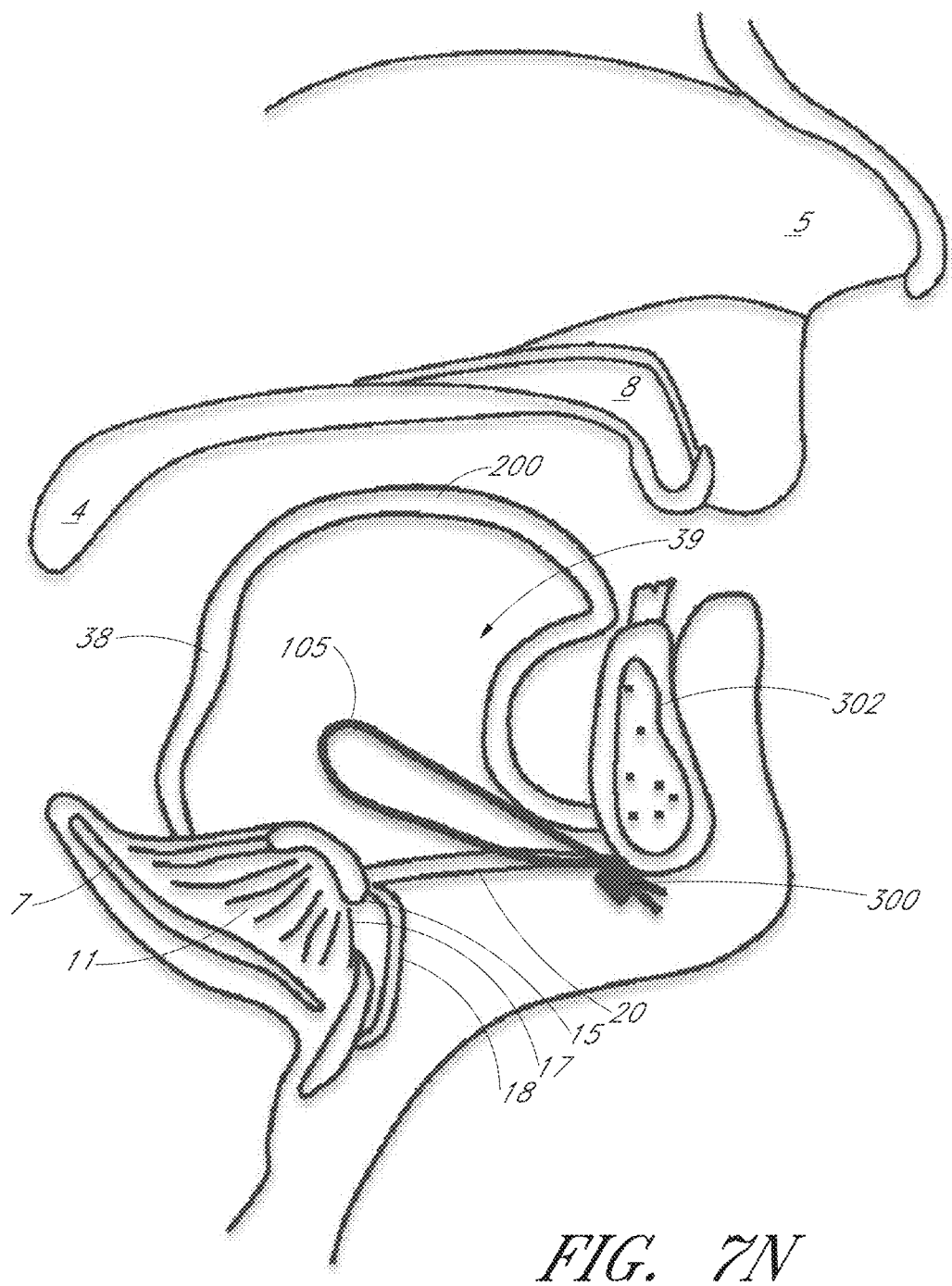
Figure 7P:
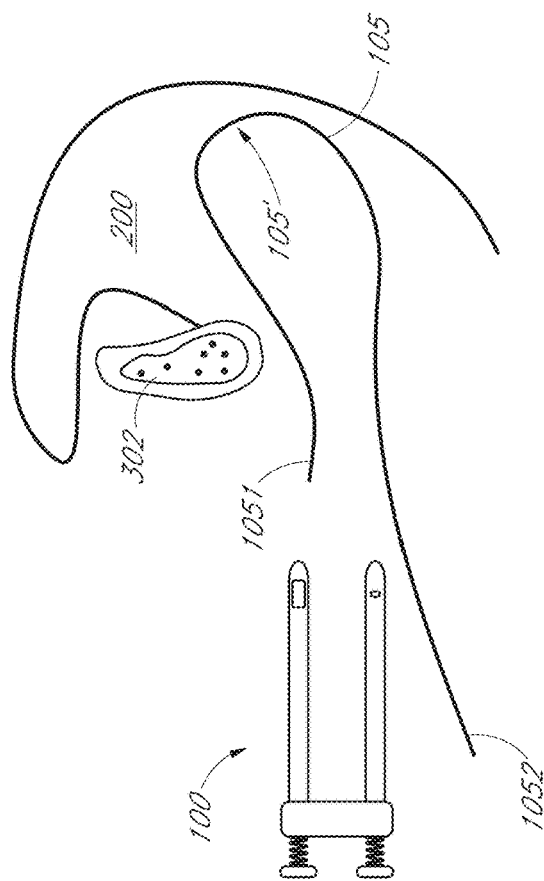
FIGS. 7O-7R illustrate one embodiment of a method to create a plurality of suture loops in tissue.

As illustrated in FIG. 7N, a bone anchor 300 could be implanted near the midline of the mandible 302 as shown, and the free ends of the tether 105a then attached thereto. Embodiments of the bone anchor 300 may be described with reference to FIGS. 8A-8E, 26A-26B, 28A-28B, 29A-29C, and 32A-32H discussed later herein. In the method shown in FIGS. 7F-7N, the free ends of the 105a do not need to be pre-attached to the bone anchor 300, allowing for additional convenience and ease in creating the appropriate tension in the suture loop. The bone anchor 300, when inserted into the mandible 302 is typically located about an anterior portion of the mandible 302 and may involve the external, internal or inferior surface of the mandible 302 or a combination of these surfaces. In some embodiments, a lateral or anterolateral location about the mandible 302 may be used.

Figure 7O:
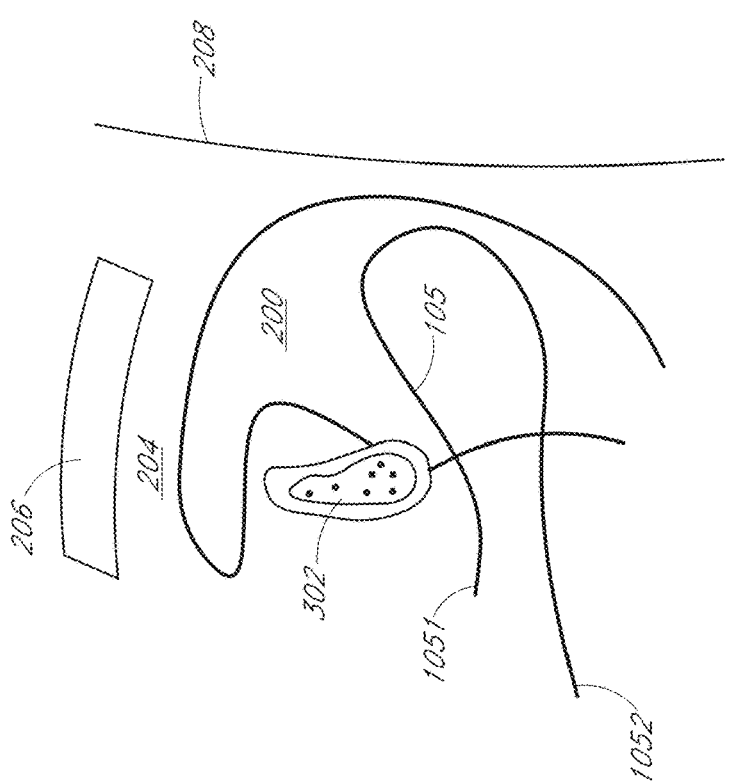

With reference to FIGS. 7O-7R, a method of passing multiple suture loops through the tongue, such as the posterior portion of the tongue, is provided. FIG. 7O illustrates a schematic sagittal cross-sectional view of a tongue 200. Above the oral cavity 204 is the palate 206, and posterior to the tongue 200 is a pharyngeal wall 208. The tongue 200 abuts the mandible 302 anteriorly.

Still referring to FIG. 7O, using a suture passer 100, which can be, for example, as previously described, a first suture loop 105' having a first end 1051 and a second end 1052 is passed through the tongue 200 in a generally anterior-to-posterior direction. However, the first end 1052 of the suture loop 105' is reintroduced onto the suture passer as illustrated in FIG. 7P and is again passed into the tongue 200. In other embodiments, a second discrete suture could be passed instead of the first end of the first suture simply reintroduced onto the suture passer. In some embodiments, one or more of suture loops 105', 105" may be vertically oriented as described in FIG. 7, or oriented in a horizontal plane, or at other various angles as previously described.

Figure 7R:
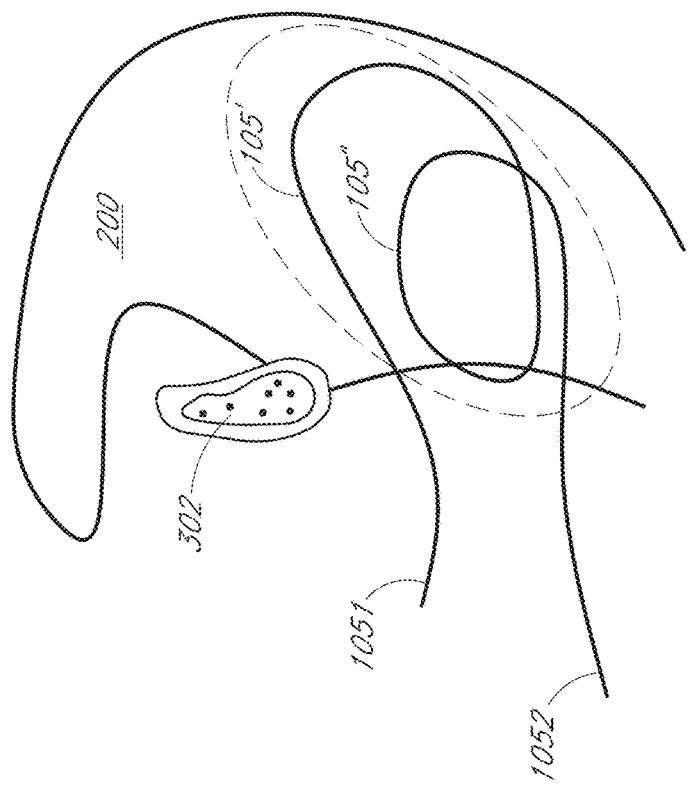
Figure 7Q:
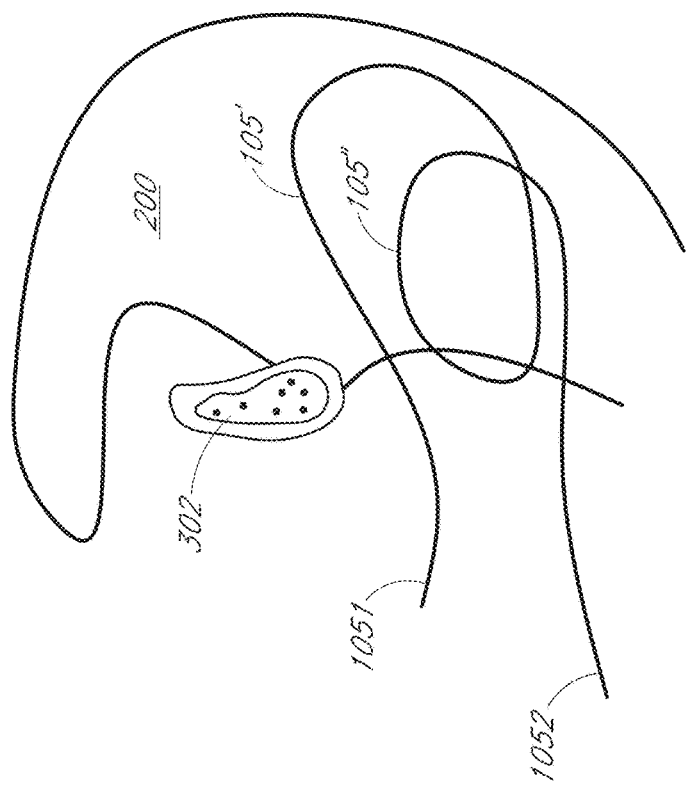

In FIG. 7Q, a second suture loop 105" is passed through the tongue 200 to provide additional tissue control. As with the first suture loop 105', the second suture loop 105" does not pass all the way through the tongue posteriorly. In some embodiments, the second suture loop 105" passes along substantially the same path as or near the same path as the first suture loop 105', or through different paths, such as described, for example, in connection with FIGS. 7A-7D above. Additionally, at least 3, 4, 5, 6, 7, 8, or more suture loops can be created in the tongue 200 by repeating the suture passing procedure to provide even more anchoring control.

In FIG. 7R, a tension force (T) is applied to the free ends 1051, 1052 of the suture loops 105', 105" to effectively compress and/or shorten the anterior-posterior dimensions of the tongue 200. The free ends 1051, 1052 could then be tied within the tongue 200, obviating the need for a bone anchor, or alternatively secured to a surrounding structure such as the mandible 302 and/or hyoid bone. In some embodiments, the tongue 200 may be compressed in the anterior-posterior direction by at least about 2%, 3%, 5%, 10%, 20%, 30%, or more. In the embodiment where the suture 105 is secured to the mandible 302 or to a bone anchor in the mandible, this single surgical technique provides two types of therapy to the tongue 200. The outer suture loop 105' (whose loop segments are closest to the end of the suture) acts to suspend the tongue 200 as described previously. The inner suture loop 105" (whose loop segment is nearest the midline of the suture) acts to compress the tissue within the tongue 200. This combined therapy from a single suture 105 may be particularly advantageous in patients with overly large tongues or with obese patients whose tongues have additional fatty deposits within the genioglossus. As a result, the procedure can increase the size of the oral cavity 204 by advancing the tongue 200 forward, which could relieve airway obstruction.

Figure 7T:
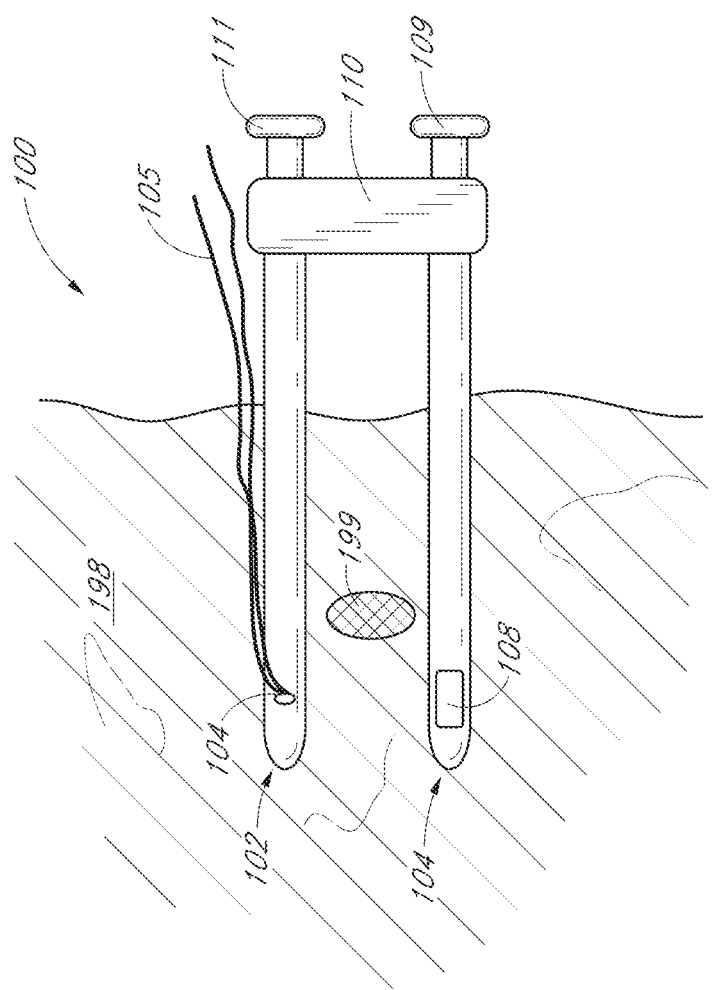
Figure 7S:
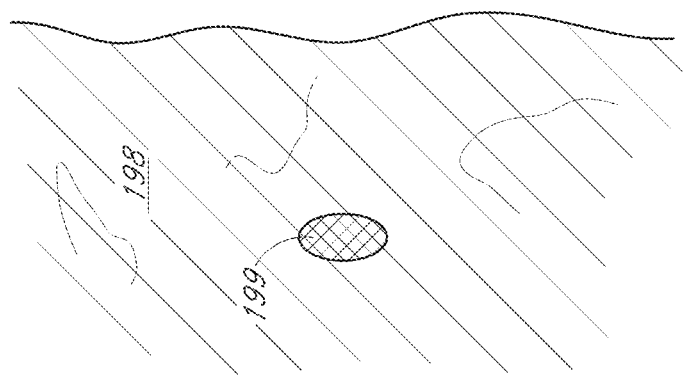
Figure 7W:
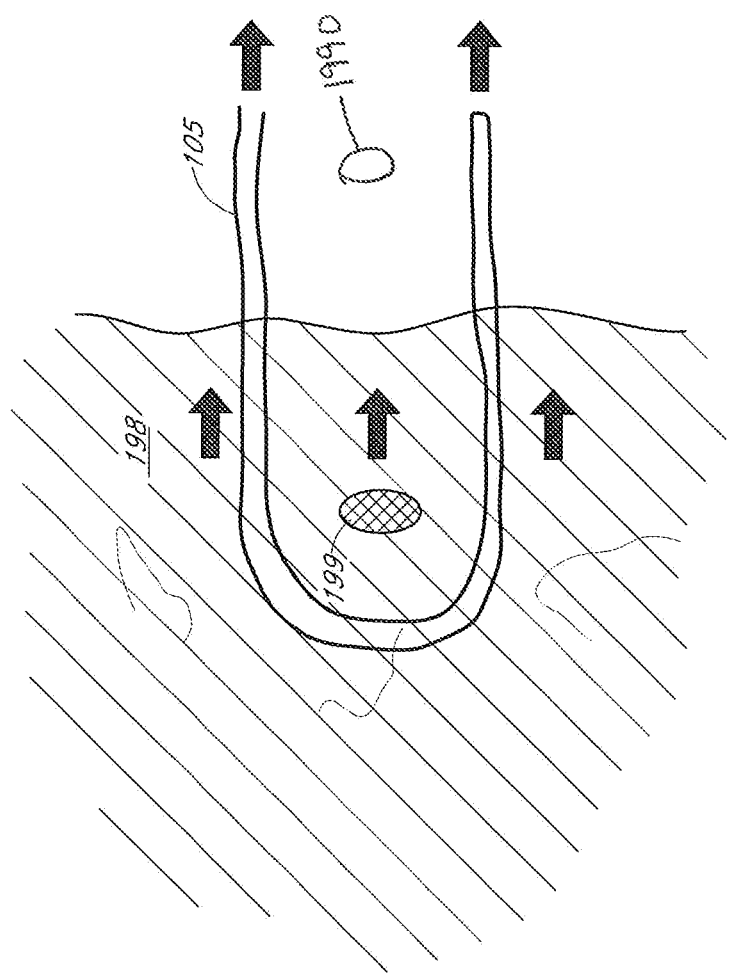

As noted, systems and methods described herein can be used to suspend any biological structure such as tissue. FIGS. 7S-7W schematically illustrate a method of using a suture passer to suspend an anatomical structure that may not be tissue. As previously, mentioned, the anatomical structure could be, for example, a tubular structure such as a blood vessel, or various other structures disclosed elsewhere herein, such as the hyoid bone for example. FIG. 7S schematically illustrates a cross-section of a structure 199 (e.g., a hyoid bone) spaced apart from a tissue surface 198. As shown in FIG. 7T, the suture passer 100 is deployed, such as into tissue 198, and positioned to pass the suture 105 around the structure 199. The suture 105 is then passed around structure 199 from suture-passing element (e.g., needle 104) to suture-receiving element 108 (such as a snare or capture window), as illustrated in FIG. 7U. The suture-passing element 104 is then retracted, and the suture-receiving element 108 transformed to capture the suture 105, as illustrated in FIG. 7V. The suture passer 100 is then retracted and removed as shown in FIG. 7W, and tension formed on the suture loop 105. The structure 199 can then be suspended to an anchoring structure 1990 such as, for example, a bone anchor, tissue anchor, or tied in a loop within the tissue 198.

Figure 8A:
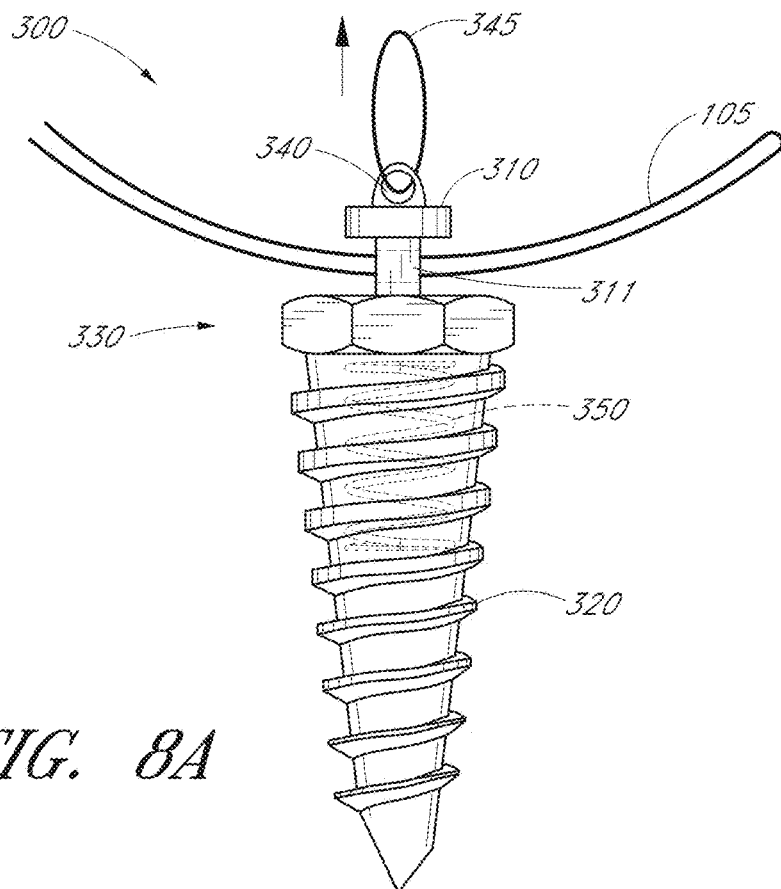
FIG. 8A illustrates an embodiment of a bone anchor to secure and guide a suture.

As described elsewhere in the application, the one or more suture loops 105 could be secured to an appropriate anatomical structure. A bone anchor can be used to facilitate securement in some embodiments. Some embodiments of bone anchors will now be described. As illustrated in FIG. 8A, one embodiment of a bone anchor 300 comprises a movable cap 310 and a screw 320. The screw 320 is generally conical and comprises threads to engage the bone or mandible of a subject. In one embodiment, the screw 320 includes a drive torque interface 330 that is configured to engage with an inserter tool with a hex-shaped interface.

The movable cap 310 is configured to axially move between an open and a closed configuration. In the closed configuration, the movable cap 310 holds and compresses the suture 105 against the screw 320. In the open configuration, the movable cap 310 releases the suture 105 so that it is free to slide in and out of the bone anchor 300 such that the cap 310 is normally biased in the closed configuration relative to the screw 320. To facilitate axial movement, one embodiment of the movable cap 310 comprises a shaft 311 configured to engage the screw 320. Movable cap 310 also comprises an aperture 340 configured to receive a suture loop 345. The suture loop 345 can tie around aperture 340 to pull the movable cap 310 and release the suture 105 from the bone anchor 300. Alternatively, a handle or other grasping structure, or a lever-arm type actuator could also be used to move the actuate the movable cap 310 with respect to the screw 320. Furthermore, a spring 350 may be coupled to the shaft of the movable cap 310 to provide a spring force to hold and to compress the movable cap 310 against the suture 105.

Figure 8B:
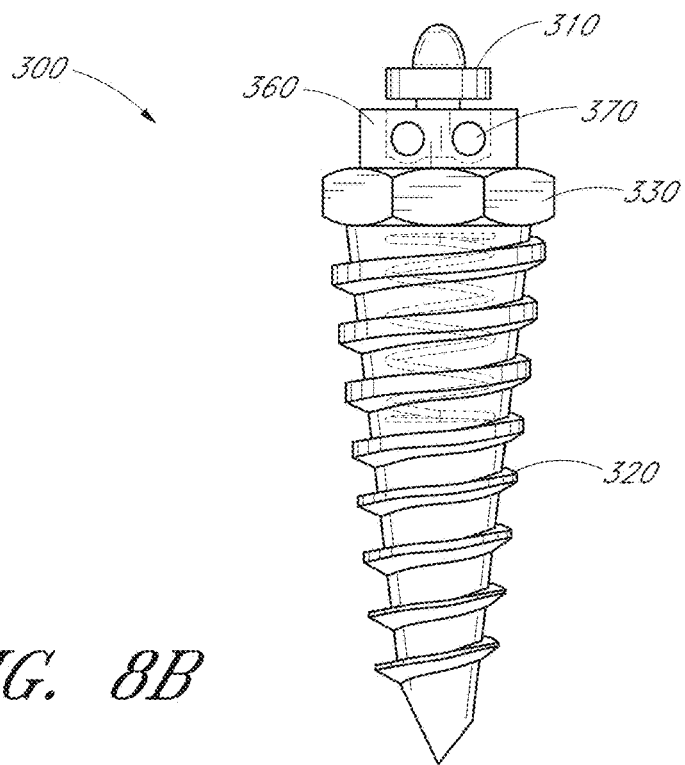
FIG. 8B illustrates another embodiment of a bone anchor using pathways, slots, or holes to guide and secure a suture.

In one embodiment as illustrated in FIG. 8B, the bone anchor may comprise an intermediate structure 360 between movable cap 310 and screw 320 that is either integrally formed or separate from movable cap 310 or screw 320. Intermediate structure 360 can include features to better engage and/or guide the suture 105, such as pathways, slots, or apertures 370 configured to house the suture 105 therethrough. Intermediate structure 360 or cap 310 could also include a plurality of holding portions on the bone anchor.

Figure 8C:
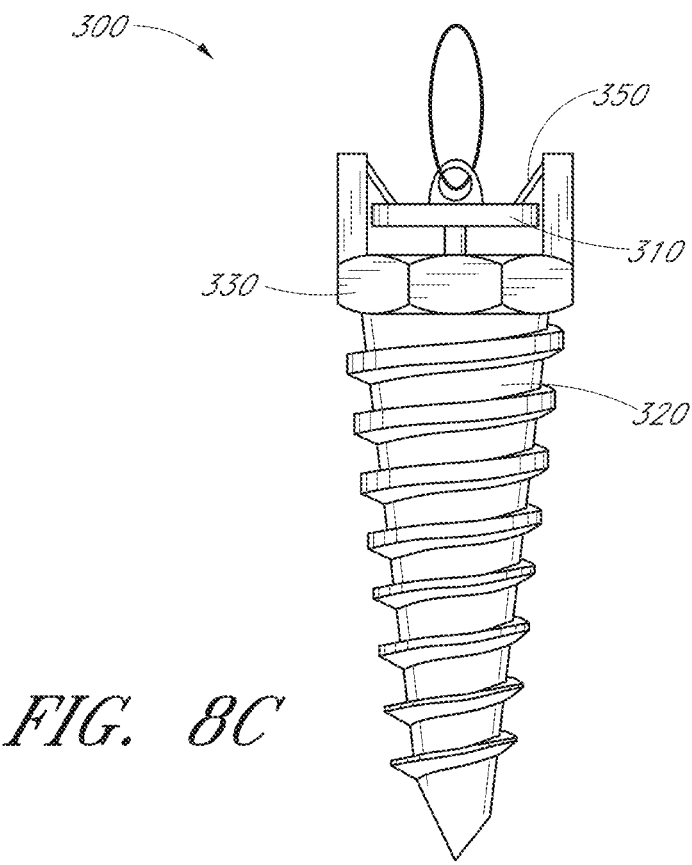
FIG. 8C illustrates another embodiment of a bone anchor using leaf springs.

In another embodiment as illustrated in FIG. 8C, movable cap 310 can alternatively or additionally include one or more spring elements 350 mechanically coupled to movable cap 310 and proximal (away from) the screw 320 such that the spring force originates proximal to the cap 310. Specifically, springs 350 can be attached to vertically extending flanges adjacent to the movable cap 310. One of ordinary skill in the art will recognize that other springs may be used to facilitate axial translation and provide spring force to hold and compress against the suture 105.

Figure 8D:
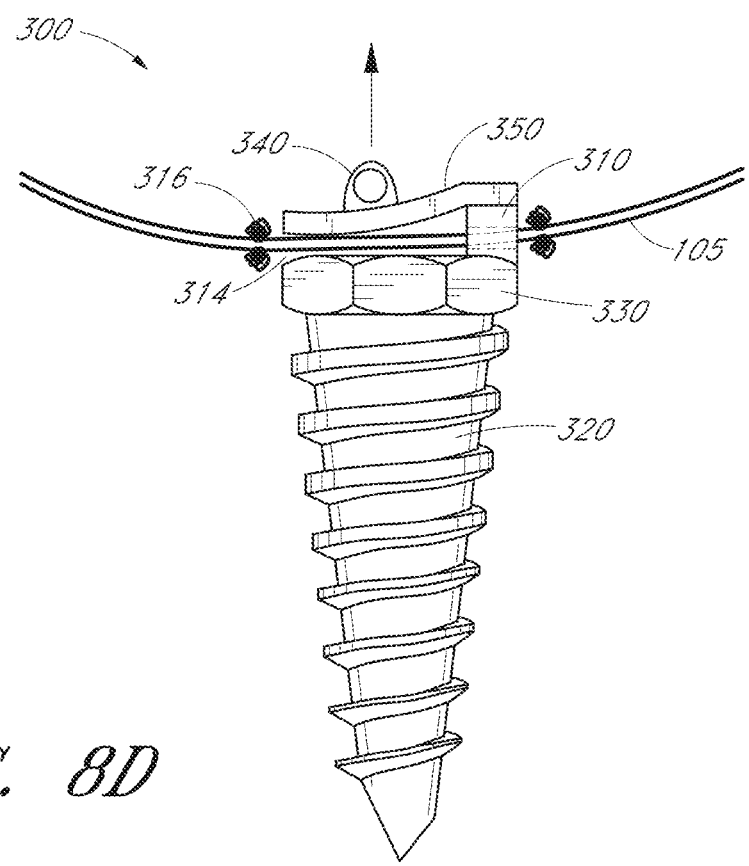
FIG. 8D illustrates yet another embodiment of a bone anchor using a nitinol spring.

In yet another embodiment, FIG. 8D illustrates an alternative spring system integrated with the movable cap 310. In particular, movable cap 310 can include a nitinol spring 350 configured to hold and compress the movable cap 310 having a knotted suture 105. Suture 105 includes one, two, or more knots 316 or other enlarged portions spaced apart from each other having a width or diameter greater than the width or diameter of a pathway 314 formed between a surface of the compressed cap 310 and the screw 320. Pulling up on the cap 310 or actuation of a release mechanism to increase the width or diameter of the pathway 314 to greater than that of the knot 316 within pathway 314 will allow for release of the suture 105 and tension adjustment.

Figure 8E:
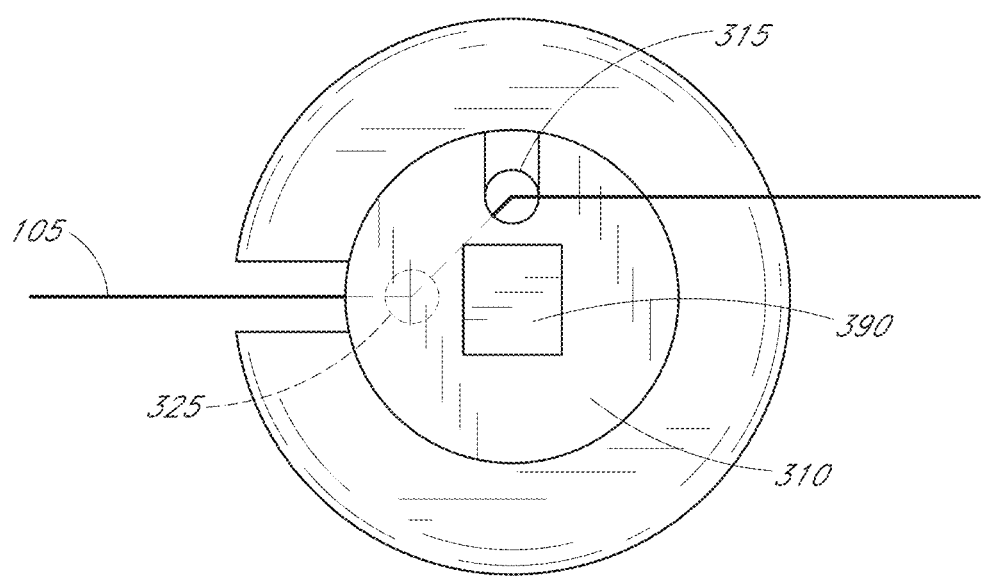
FIG. 8E illustrates still another embodiment of a bone anchor to releasably lock a suture to the bone anchor via cams or mismatched holes.

In still another embodiment, FIG. 8E shows movable cap 310 and screw 320 configured to advantageously lock suture 105 via cams or mismatched holes, rather than having movable cap 310 or screw 320 axially translate to hold and compress against suture 105. Movable cap 310 comprises a cap hole 315 and screw 320 comprises a screw hole 325, each hole configured to allow suture 105 to pass through. Movable cap 310 can further include a shaped bore 390 configured to mate with a shaped driver, e.g., hex- or square-shaped driver. The driver mates with the shaped bore 390 and rotates the movable cap 310 clockwise or counter-clockwise relative to the screw 320. Upon rotating the movable cap 310, the cap hole 315 rotates while the screw hole 325 remains fixed. When the cap hole 315 is directly aligned with screw hole 325, the suture 105 slides freely through the bone anchor 300. When the cap hole 315 is mismatched with screw hole 325, the suture 105 is locked to the bone anchor 300. As noted, previously, various other non-limiting examples of adjustment mechanisms that can be utilized to adjust the tension of the one or more sutures are described and illustrated in connection with FIGS. 61A-K and 73-108 of U.S. Pat. Pub. No. 2008/0023012 to Dineen et al., which is hereby incorporated by reference in its entirety. Other bone anchors that can be used in the tissue suspension system as described herein can be found, for example, in U.S. Pat. No. 5,443,482 to Stone et al., such as those described and illustrated in connection with FIGS. 1-10B, U.S. Pat. No. 5,411,523 to Goble, such as those described and illustrated in connection with FIGS. 1-8, both of which are hereby incorporated by reference in their entireties.

In FIGS. 9A and 9B, an embodiment of a suture passer system 900 is disclosed. The suture passer system 900 is a dual-shaft configuration for a suture passer described earlier (e.g., FIGS. 1A-1B, 1E-1F, 2, 5A-5E, 5G-5I, 6, 7E-7N) or elsewhere herein. For the purposes of simplicity, the suture passer system 900 is only illustrated with a first elongate or needle shaft 902, and a second elongate or retrieval shaft 906. The rest of the structure of the suture passer system 900 is omitted. Bite width (the width of the suture pass) may be adjusted before insertion of the suture passer 900. Bite width may be adjusted to best match the physician's desired tissue suspension result. The bite width or distance between the first elongate shaft 902 and the second elongate shaft 906 adjust the amount of tongue tissue to be captured. The bite width can also be adjusted after the suture passer 900 is initially inserted into tissue. For the genioglossus, this would allow a compact shaft configuration for initial insertion and for getting beyond the neurovascular bundles within the tongue. Once the suture passer tips were safely beyond these structures, the distance between the shafts can be increased, resulting in a larger tissue bite during the suture pass. Thus, the suture passer system can be transformable such that there is a first distance between the distal ends of the first and second shafts when the system is in a first configuration, and there is a second distance between the distal ends of the first and second shafts when the system is in a second configuration, wherein the second distance is at least about 10%, 20%, 30%, 40%, 50%, 75%, 100%, or more of the first distance.

In FIGS. 9A and 9B, the bite adjustment is achieved by rotation of the retrieval shaft 906. After insertion of the suture passer 900 into the tissue, the retrieval shaft 906 may be rotated to a wider position away from the needle shaft 902, as illustrated in FIG. 9A. Before insertion of the suture passer 900 into the tissue, the retrieval shaft 906 may be rotated to a narrower position toward a needle shaft 902, as illustrated in FIG. 9B.

Figure 10:
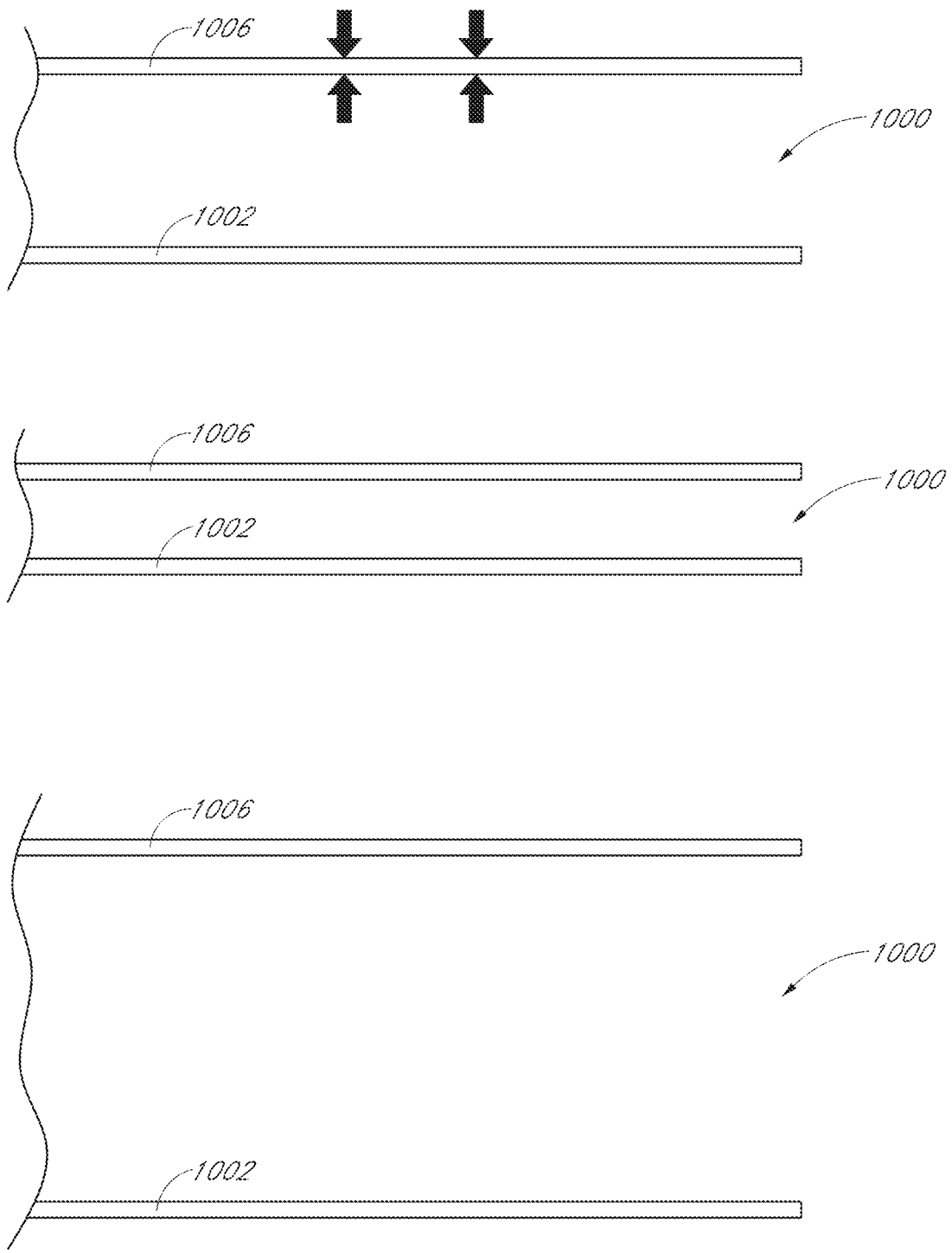
FIG. 10 depicts a suture passer system in another embodiment showing bite adjustment by slide control.
Figure 12A:
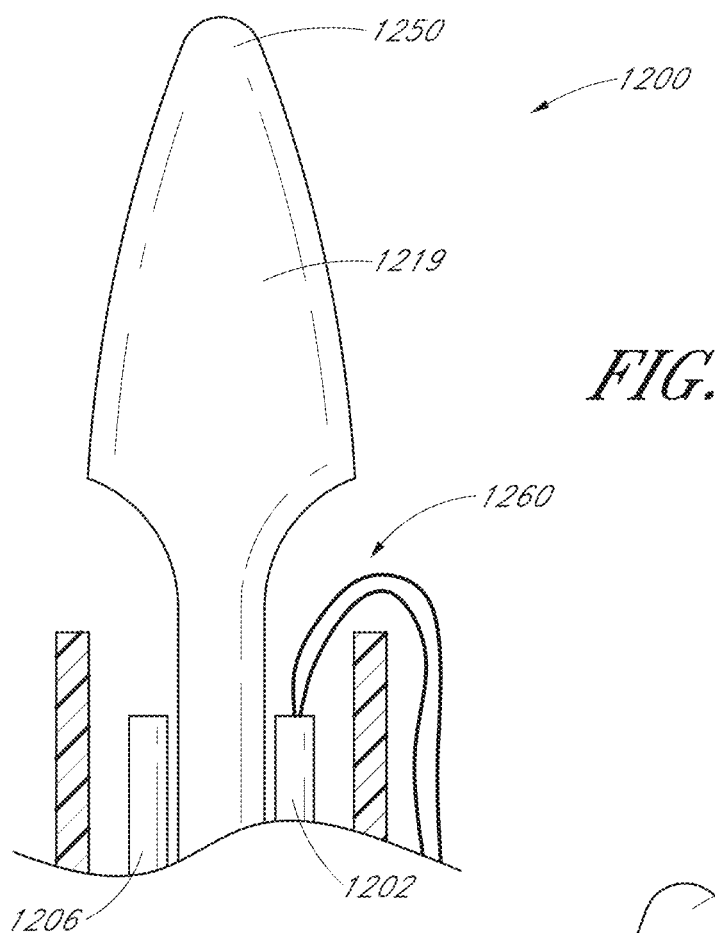
FIG. 12A-12D illustrates another embodiment of a suture passer system with a deflecting element and a depth determining tip.
Figure 12B:
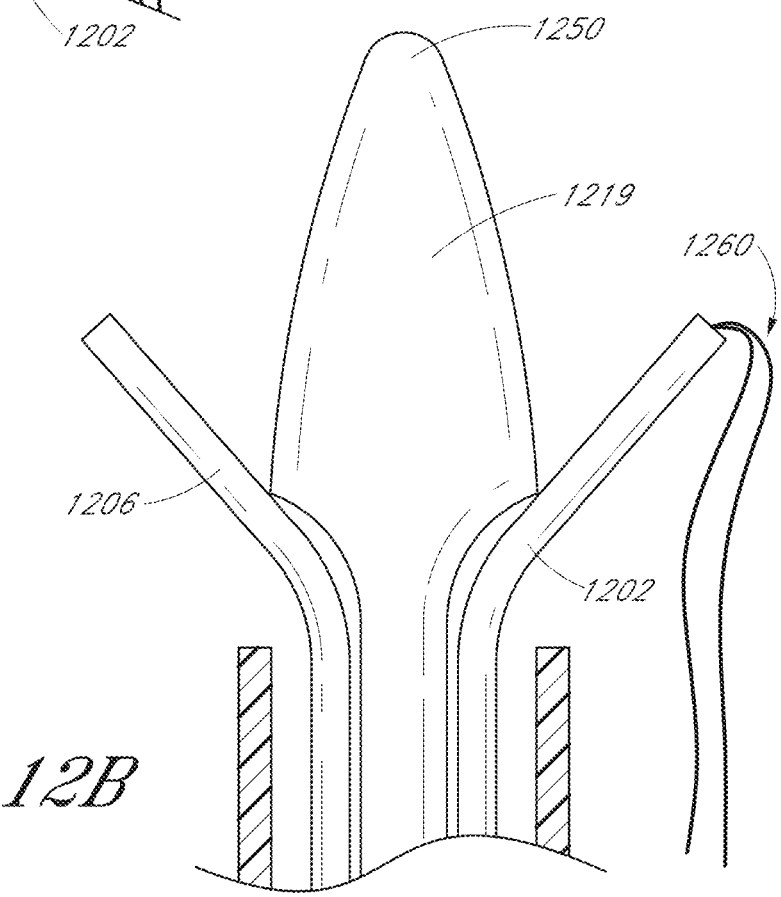
Figure 12C:
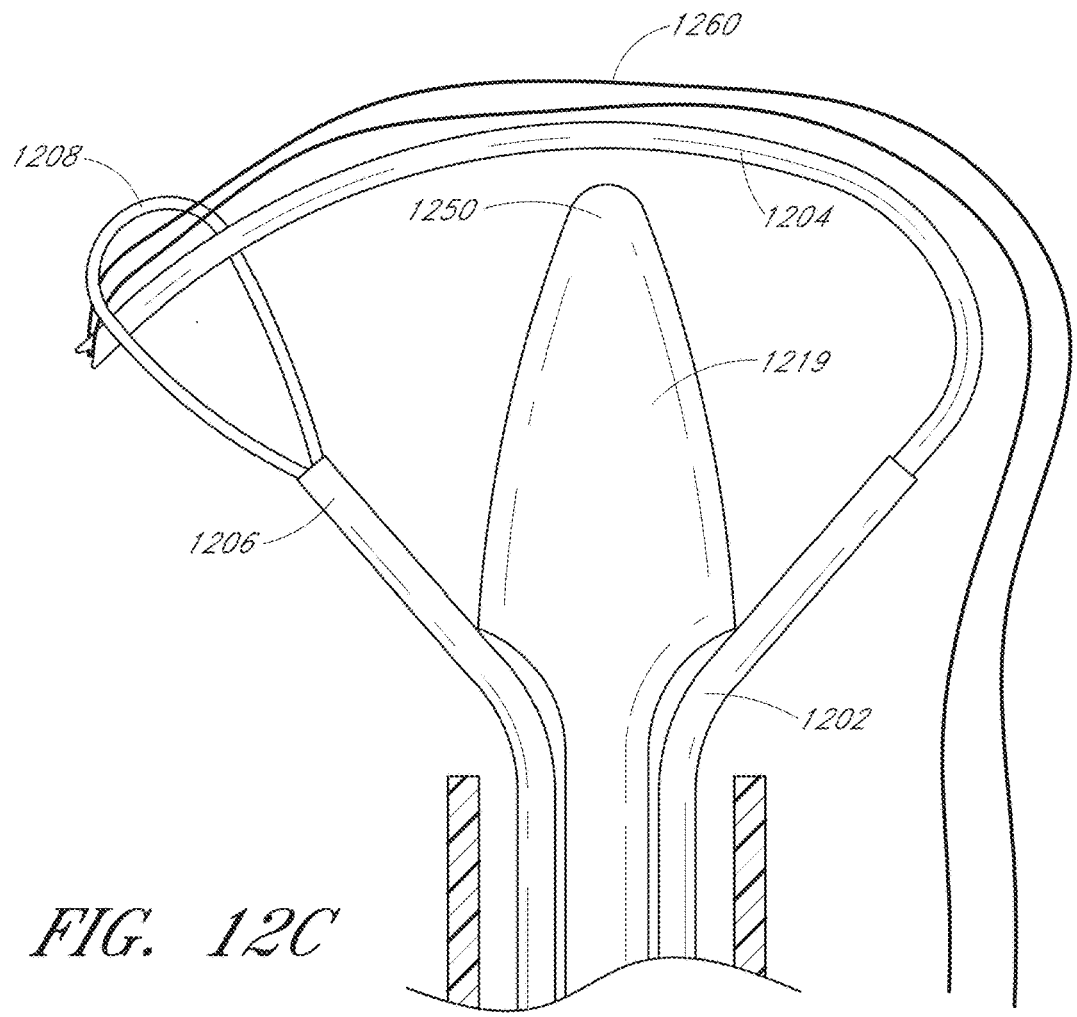
Figure 12D:
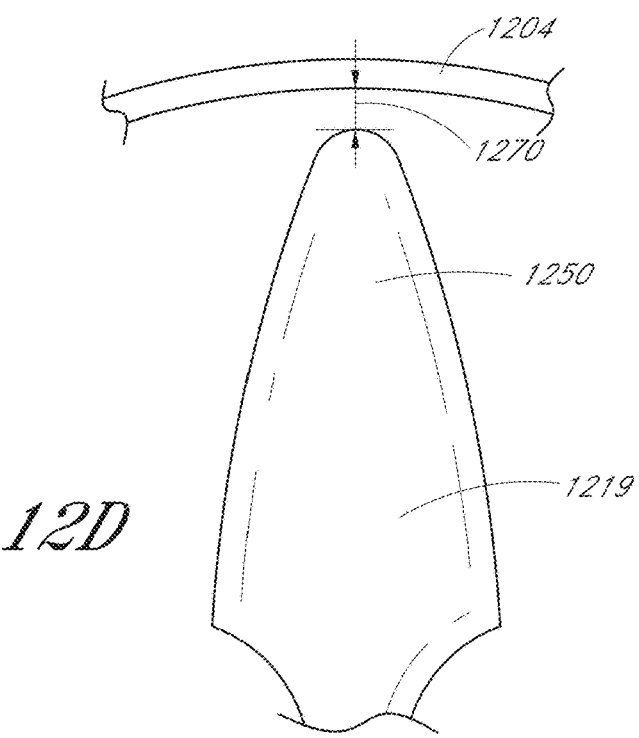

In FIG. 10, another embodiment of a suture passer system 1000 is disclosed. the suture passer system 1000 may be a dual-shaft suture passer described earlier or elsewhere herein. For the purposes of simplicity, the suture passer system 1000 is only illustrated with a first elongate or needle shaft 1002, and a second elongate or retrieval shaft 1006. The rest of the structure of the suture passer system 1000 is omitted. In this case, the bite width may be achieved by sliding the retrieval shaft 1006 closer to the needle shaft 1002.

FIGS. 11A and 11B illustrate non-parallel shafts 1102, 1106 of a suture passer system 1100. In FIG. 11A, a user may adjust the angle of either shaft 1102 or 1106 by, for example, pushing shafts 1102 and 1106 closer together. In FIG. 11B, a user may use an angle control mechanism 1140 to control the rotation of one or both shafts 1102, 1106. The angle may be changed by the user before or after insertion of the suture passer system 1100 into tissue. To accommodate the widest possible angle setting, the suture passer system 1100 may need to have sufficient tissue penetration. In some embodiments, the angle can be adjusted by between about 10-170 degrees, such as between about 10-90 degrees, or between about 10-45 degrees in some embodiments.

In yet another embodiment of a suture passer system 1200, FIGS. 12A-12D illustrate a depth determining tip 1250 that advantageously allows a suture pass 1260 to happen at a determined depth before, at, or beyond a tissue boundary, membrane, change in tissue density, or solid structure located within tissue where these may be at an unknown depth with the tissue where the suture passer system 1200 is inserted. As illustrated in FIGS. 12A-12D, one embodiment of the suture passer system 1200 comprises a deflecting element 1219 having a depth determining tip 1250 at a distal end of deflecting element 1219. As discussed earlier herein, the first elongate shaft 1202 and the second elongate shaft 1206 may be deflected by the deflecting element 1219 when advanced. As a suture-passing element 1204 or needle extends through a suture-receiving element 1208 or snare, the suture-passing element 1204 or needle extends distally past the depth determining tip 1250 at a distance 1270. This provides a suture pass 1260 to be performed at a determined depth. The depth of the suture pass 1260 may equal the distance 1270. In some embodiments, the distance 1270 is less than about 5 cm, 4 cm, 3 cm, or 2 cm. In other embodiments, the distance 1270 is less than about 1 cm. This embodiment of the suture passer system 1200 advantageously can provide a suture pass 1260 at an interface of two tissue types, e.g., genioglossus muscle and mucosa of the tongue, a first tissue type having a different density, ease of insertion, or other property than a second tissue type. Additionally, the suture passer system 1200 allows a suture pass 1260 at an interface layer or at a known depth into the most distal tissue layer. For example, when the suture passer system 1200 is inserted into a softer tissue region, a suture pass 1260 may be formed where there is a second denser tissue region, boundary, or membrane. The depth determining tip 1250 is blunt in some embodiments. Increased penetration resistance observed by the surgeon, which can occur at the boundary between a first tissue layer and a second tissue layer, could serve as an indicator that the suture passer was at the desired depth to perform the suture pass.

Figure 13:
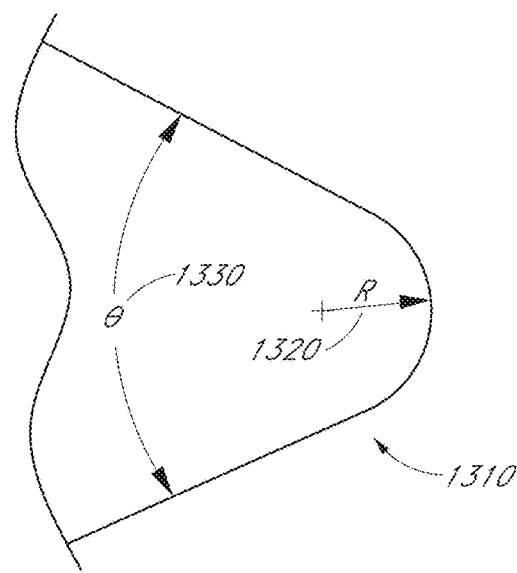
FIG. 13 illustrates a distal tip for an elongate shaft of a suture passer system for blunt dissection of tissue.

FIG. 13 schematically illustrates a distal tip 1310 of an elongate shaft of a suture passer system (not shown). In this embodiment, the distal tip 1310 has a blunted edge to provide for blunt dissection of tissue. The distal tip 1310 has a pre-determined radius of curvature 1320 and a pre-determined angle of curvature 1330. Table 1 below illustrates, in one embodiment, one non-limiting example of an operating range for blunt dissection of muscle without piercing the mucosa. In some embodiments, the radius of curvature 1320 is from about 0.01 inches to about 1.00 inches, and the angle of curvature 1330 is from about 40° to about 180°. With blunt dissection in this operating range, this advantageously allows for tissue penetration into the genioglossus without piercing the mucosa, thereby providing for a depth control mechanism. Also, blunt dissection greatly reduces the chance of blood vessel perforation and bleeding if the suture passer system ends up striking the larger blood vessels within tissue.

TABLE 1

|  | Minimum | Maximum |
|---|---|---|
| Radius of Curvature (R) | 0.01 inches | 1.00 inches |
| Angle of Curvature (θ) | 40° | 180° |

Figure 14:
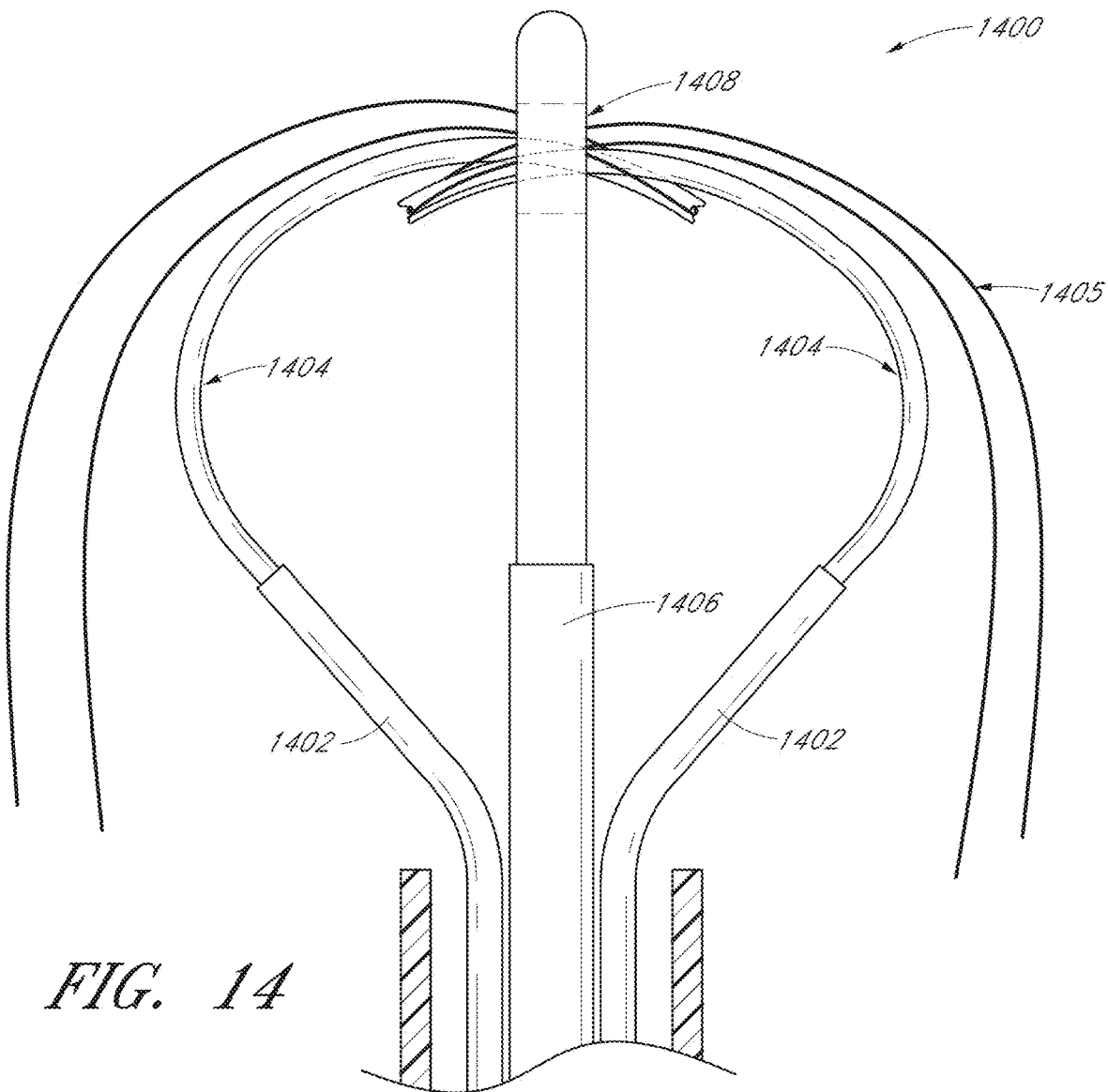
FIG. 14 illustrates one embodiment of a suture passer system configured to pass multiple sutures at one time.

FIG. 14 illustrates an embodiment of a suture passer system 1400 that allows for a plurality of sutures 1405 be passed simultaneously. The suture passer system 1400 comprises two or more elongate shafts 1402. Each elongate shaft 1402 is configured to deploy a suture needle 1404 carrying a suture 1405. As illustrated in FIG. 14, a suture receiving element 1408 or snare/window extends from an elongate shaft 1406 in between each of the elongate shafts 1402. Two or more sutures 1405 may advantageously be passed in the same tissue plane through a single capture window 1408, via suture needles 1404 which may oppose each other as shown. In other embodiments, each suture can be received through separate retrieval elements, such as snares or capture windows 1408.

Figure 15A:
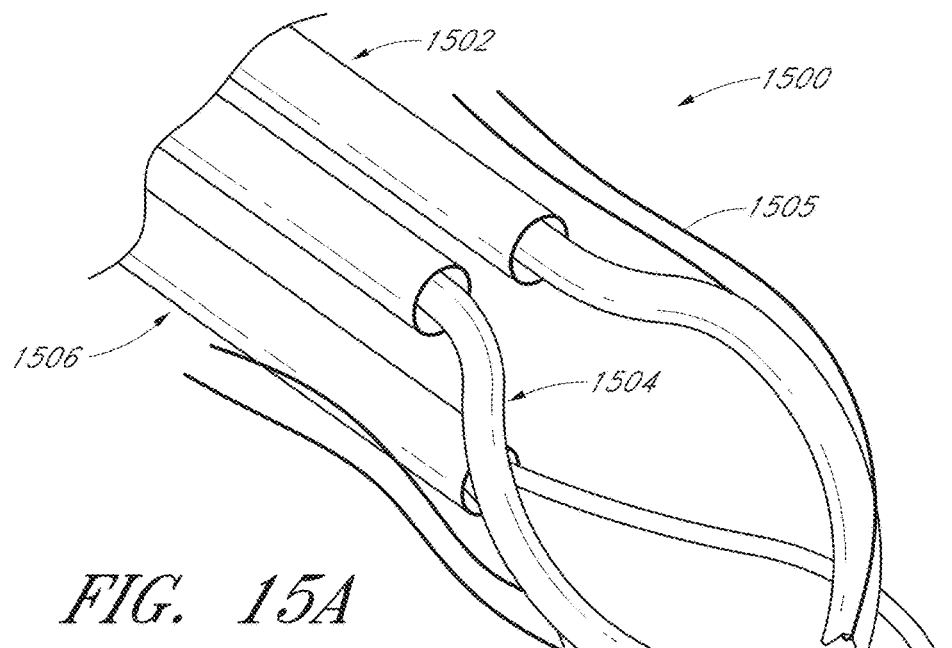
FIGS. 15A-15C illustrate another embodiment of a suture passer system configured to pass multiple sutures at one time.
Figure 15B:
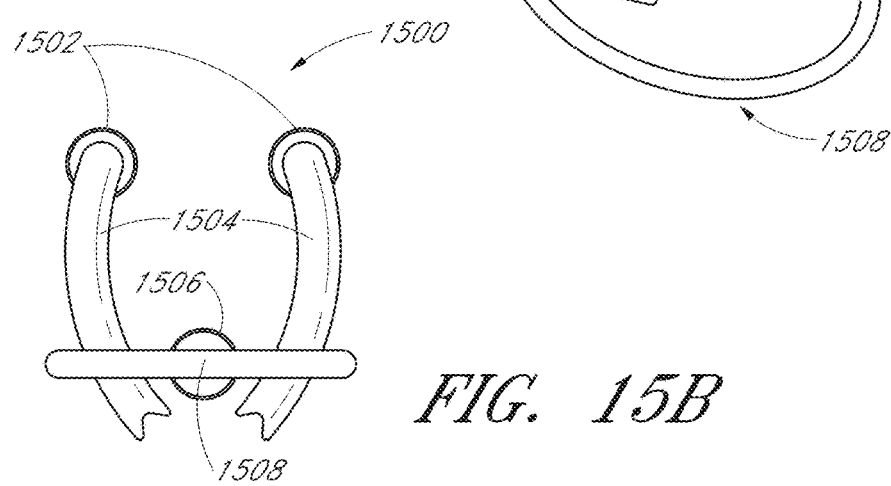
Figure 15C:
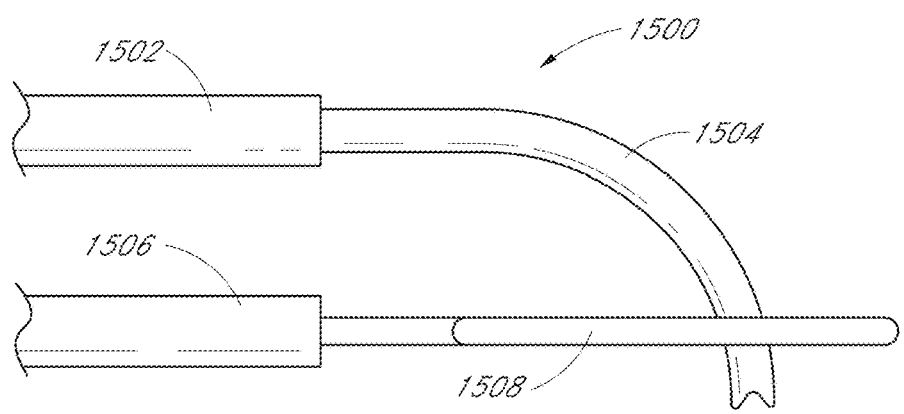

In still another embodiment, FIGS. 15A-15C illustrate one, two, or more suture-passing shafts 1502 (which can be, for example, a single shaft having a barrier in between the suture-passing elements 1504, and one, two, or more suture-receiving or snare shafts 1506. FIG. 15B is an end view of the system of FIG. 15A, while FIG. 15C is a side view. As illustrated, first and second suture needles 1504 can each pass first and second sutures 1505 to be retrieved by one, two, or more snares 1508 or capture windows.

Figure 16A:
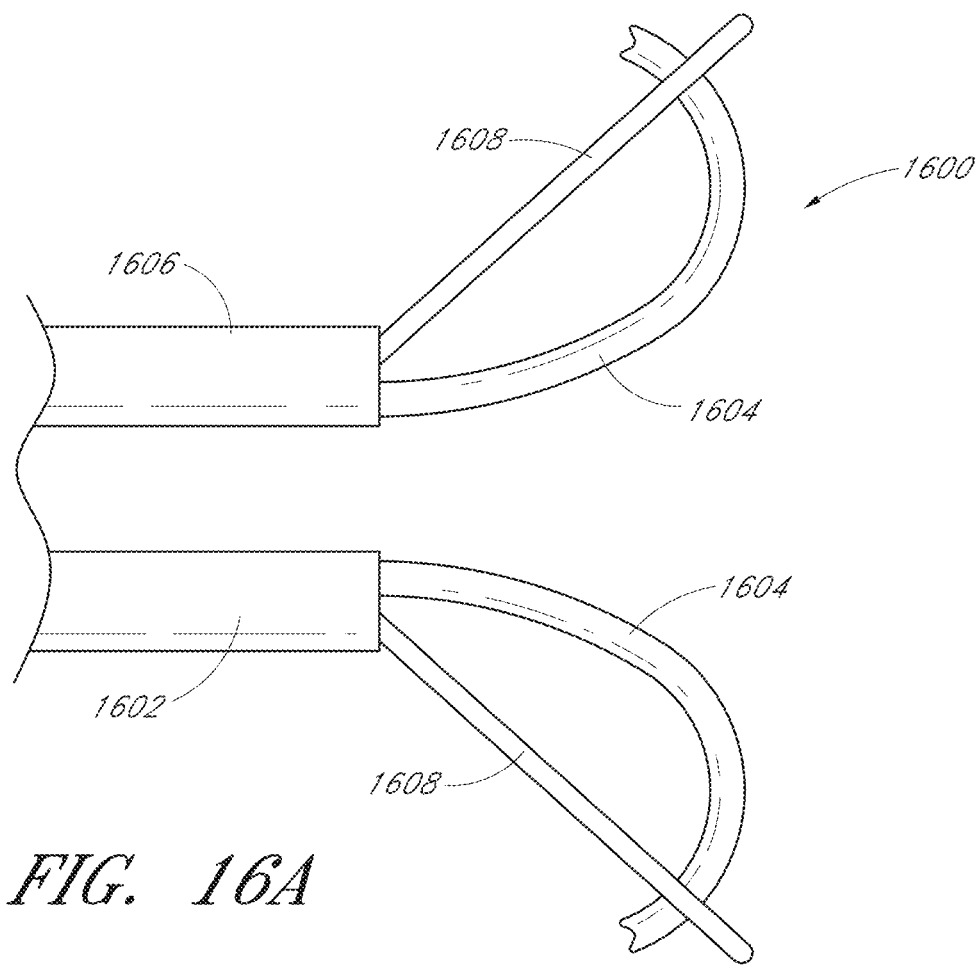
FIGS. 16A-16B illustrate another embodiment of a suture passer system configured to pass multiple sutures at one time.
Figure 16B:
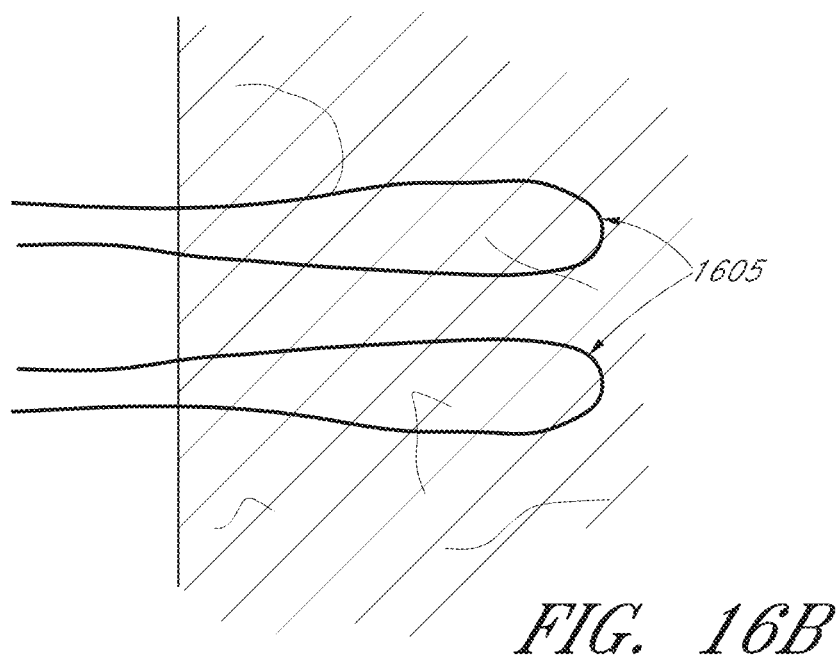

In yet another embodiment, FIGS. 16A-16B show another suture passing system 1600 configured to pass multiple sutures at one time. The "double-loop" suture passing system 1600 illustrates two elongate shafts 1602 and 1606, wherein each shaft 1602 and 1606 houses a suture-passing element 1604 or needle as well as a suture-receiving element 1608 or snare. When the suture-passing elements 1604 and the suture-receiving elements 1608 are deployed, two or more suture loops 1605 may be formed. The plurality of independent suture loops 1605 formed after suture passes formed by the system illustrated in FIG. 16A are illustrated in FIG. 16B.

Figure 17A:
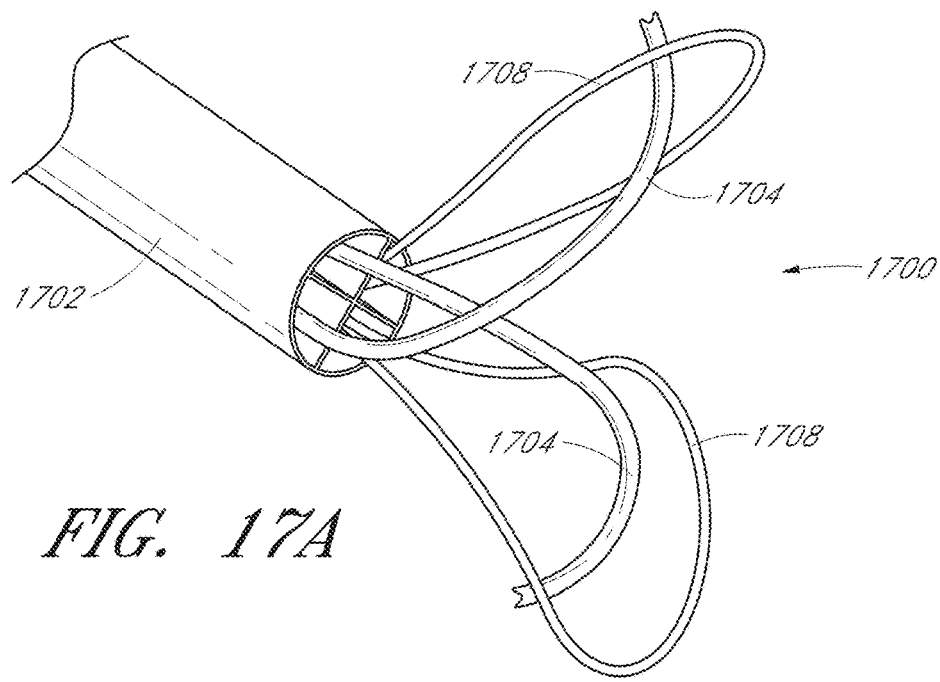
FIGS. 17A-17C illustrate another embodiment of a suture passer system configured to pass multiple sutures at one time.
Figure 17B:
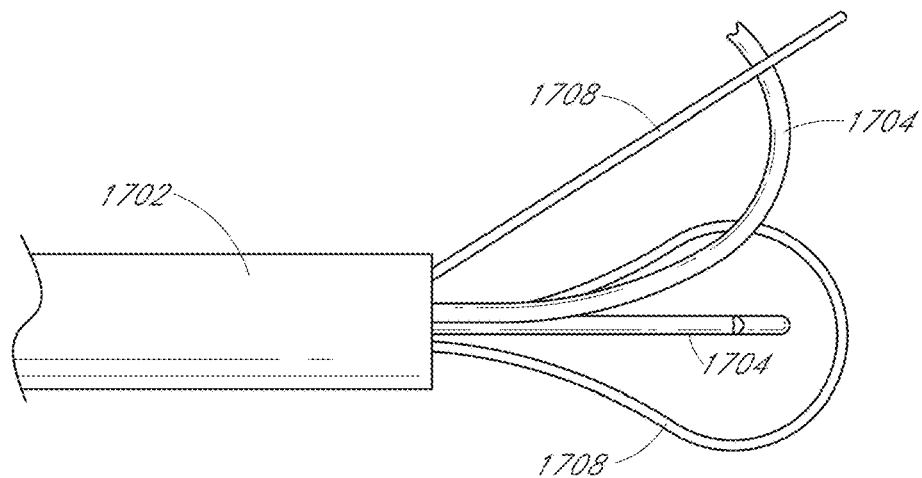
Figure 17C:
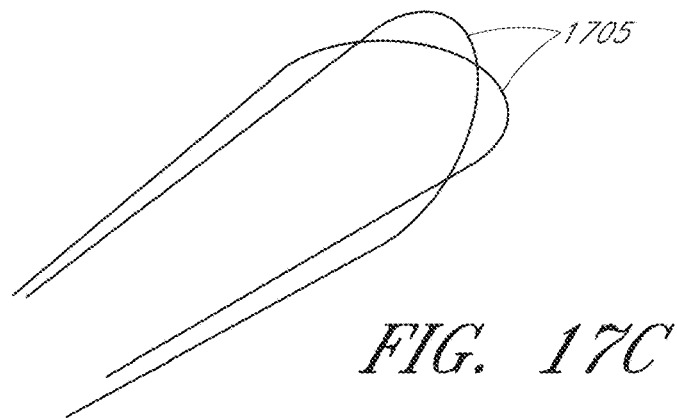

In another embodiment of a suture passing system 1700 for creating multiple suture passes, FIGS. 17A-17C illustrate a single shaft 1702 configured to deploy two suture-passing elements 1704 or needles and two suture-receiving elements 1708 or snares. Specifically, a first suture-passing element 1704 extends through a first suture-receiving element 1708 spaced 180 degrees apart along the circumference of the opening of the shaft 1702, and a second suture-passing element 1704 extends through a second suture-receiving element 1708 spaced 180 degrees apart along the circumference of the opening of the shaft 1702 as illustrated. Therefore, two or more suture loops 1705 are created having a "parachute" tissue passes and geometry, as illustrated in FIG. 17C. This embodiment advantageously allows for single shaft insertion into the tissue, thus potentially allowing for a smaller device profile.

Figure 18A:
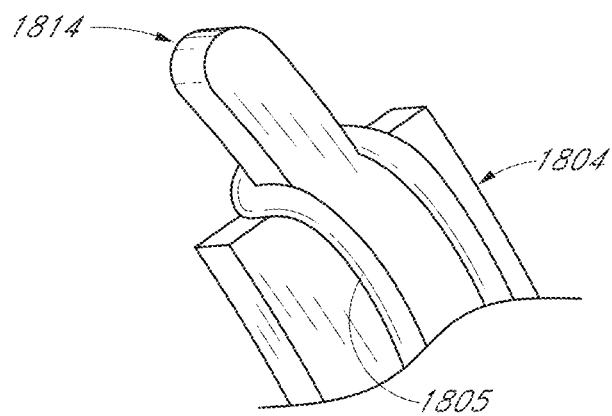
FIG. 18A illustrates an embodiment of a suture-passing element or needle having a shouldered distal tip.
Figure 18B:
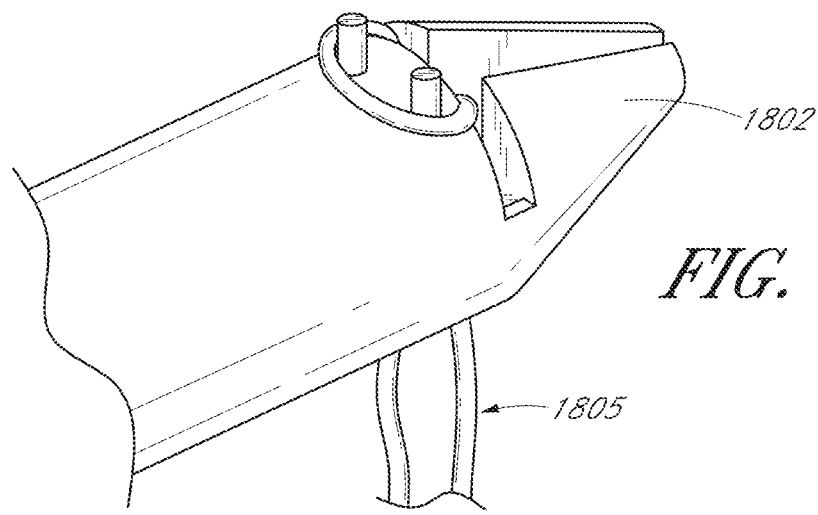
FIGS. 18B-18C illustrate a method of engaging a suture retained on an elongate shaft with the needle of FIG. 18A.
Figure 18C:
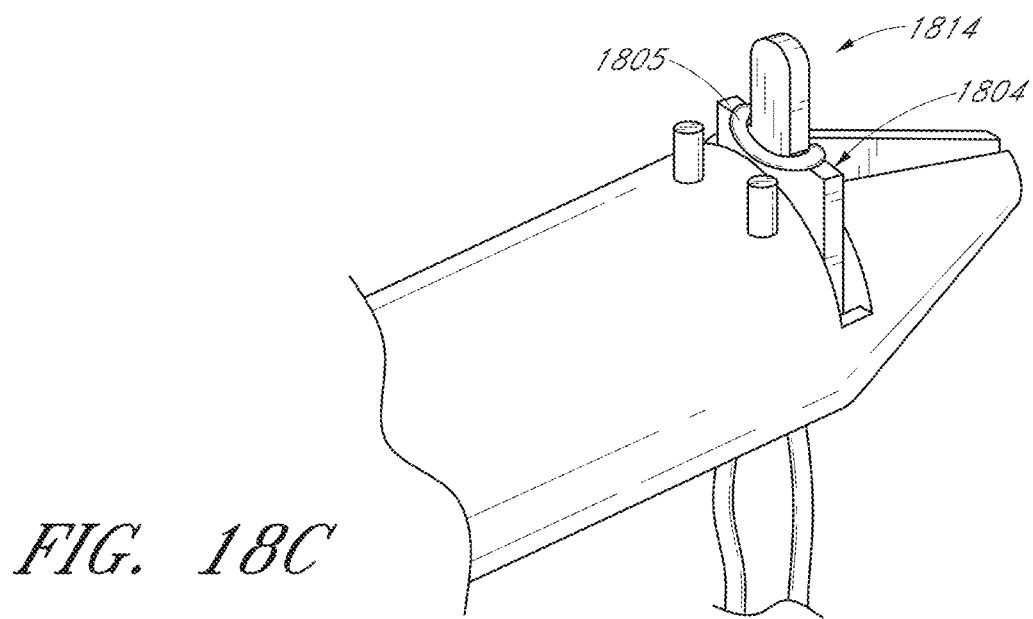

FIGS. 18A-18C illustrate a "shouldered" needle 1804 having a distal tip projection 1814 that is configured to carry a suture loop 1805 rather than a strand of suture. As illustrated in FIG. 18A, the distal tip 1814 allows the needle 1804 to keep the suture loop 1805 on the backside of the needle 1804, which may be advantageous, for example, if the needle has a flat or ribbon-type surface. Therefore, as shown in FIGS. 18B-18C, the suture 1805 may be retained on an elongate shaft 1802, and the suture 1805 can be passively engaged during advancement of the needle 1804. In this embodiment, the suture 1805 advantageously need not be preloaded on needle 1804, as illustrated in FIG. 18B. When the needle 1804 advances through the elongate shaft 1802 as illustrated in FIG. 18C, the needle 1804 engages the suture 1805. This embodiment may advantageously reduce the effect of trauma or laceration to the tissue caused by the suture, e.g., "cheese-cutting" tissue during a suture pass.

Figure 19A:
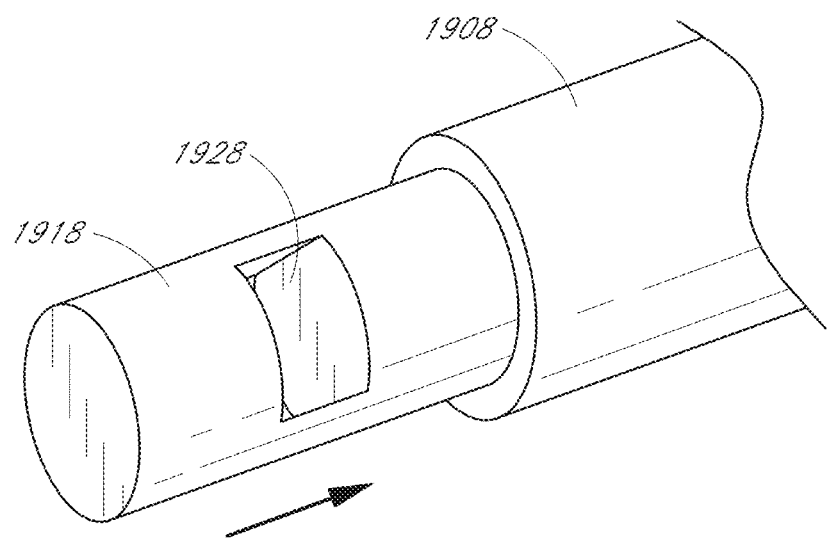
FIGS. 19A-19B illustrate one embodiment of a suture-receiving element having a retractable rod.
Figure 19B:
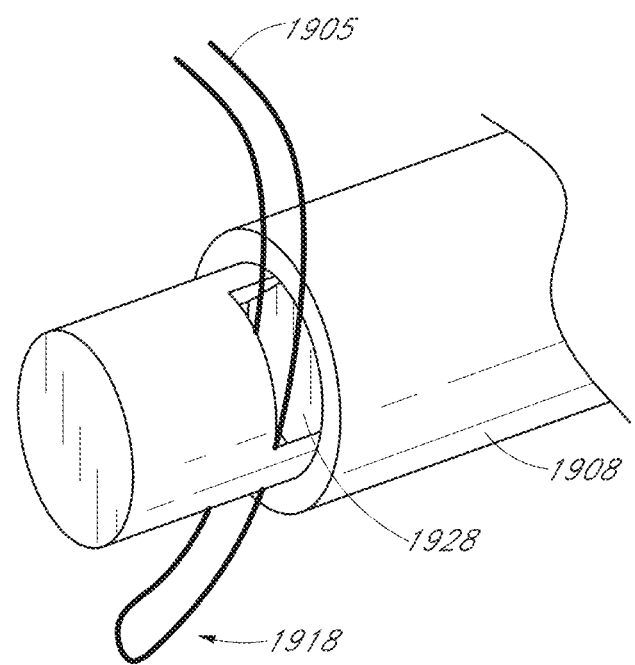

FIGS. 19A-19B illustrate one embodiment of a suture-receiving element 1908 or hypotube housing a retractable rod 1918 at a distal end of suture-receiving element 1908. The retractable rod 1918 comprises an aperture 1928 dimensioned to receive a suture-passing element (not shown). When a suture 1905 is passed through the aperture 1928, the rod 1918 is retracted or the hypotube 1908 is advanced to capture the suture 1905, as illustrated in FIG. 19B.

Figure 20A:
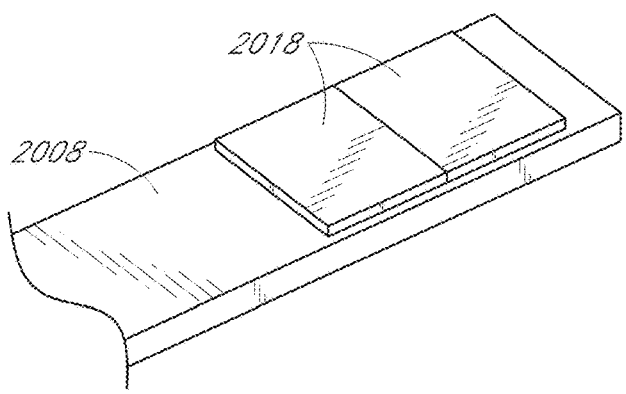
FIGS. 20A-20D illustrate another embodiment of a suture-receiving element having leaf springs.
Figure 20B:
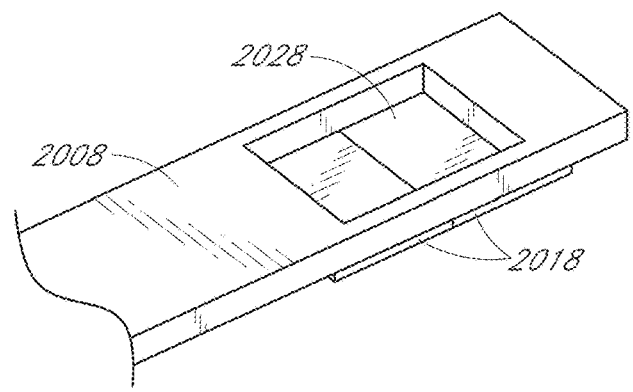
Figure 20C:
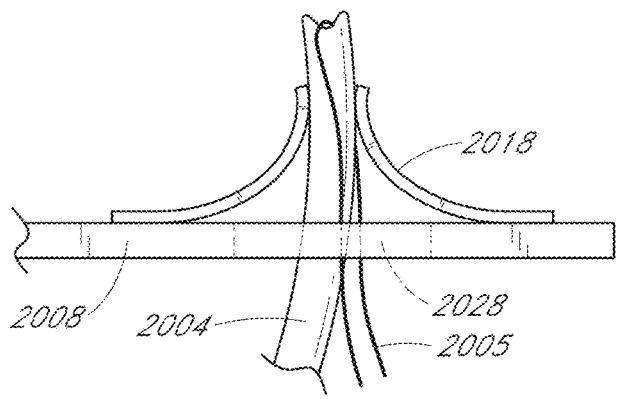
Figure 20D:
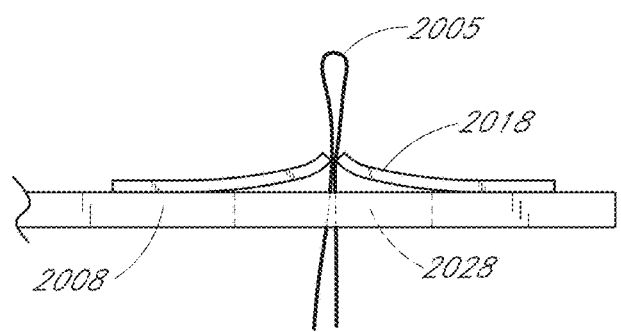

In FIGS. 20A-20D, still another embodiment of a suture-receiving element 2008 is illustrated comprising movable panels such as thin leaf springs 2018, and window 2028. FIG. 20A is a top view, while FIG. 20B is a bottom view. The leaf springs 2018 are positioned on one side of the window 2028 and adjacent to each other, and biased radially inwardly. When a suture-passing element 2004 or needle is advanced with suture 2005 through the window 2028, the leaf springs 2018 are deflected, such as in a radially outward direction, so that the needle 2004 may advance past the leaf springs 2018, as illustrated in FIG. 20C. When the needle 2004 is retracted, the leaf springs 2018 close and capture the suture 2005 as illustrated in FIG. 20D. This embodiment advantageously does not require activation of the retrieval element by the surgeon to secure the suture 2005.

Figure 21A:
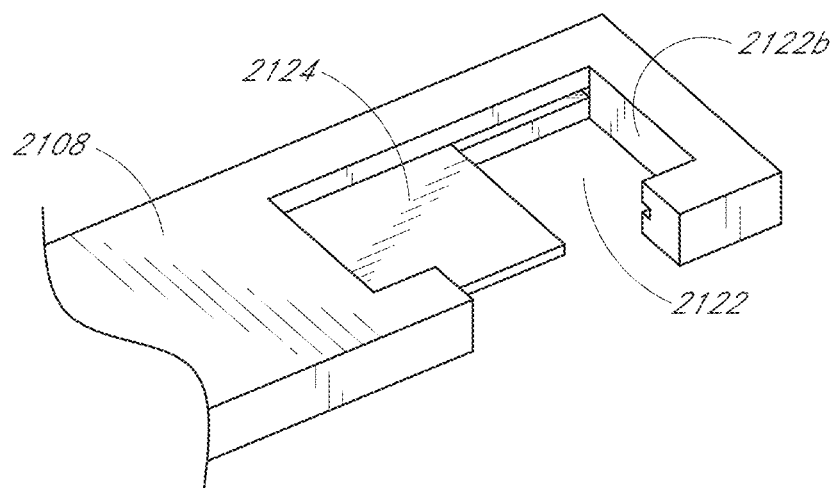
FIGS. 21A-21B illustrate another embodiment of a suture-receiving element having a C-shaped frame for a capture window.
Figure 21B:
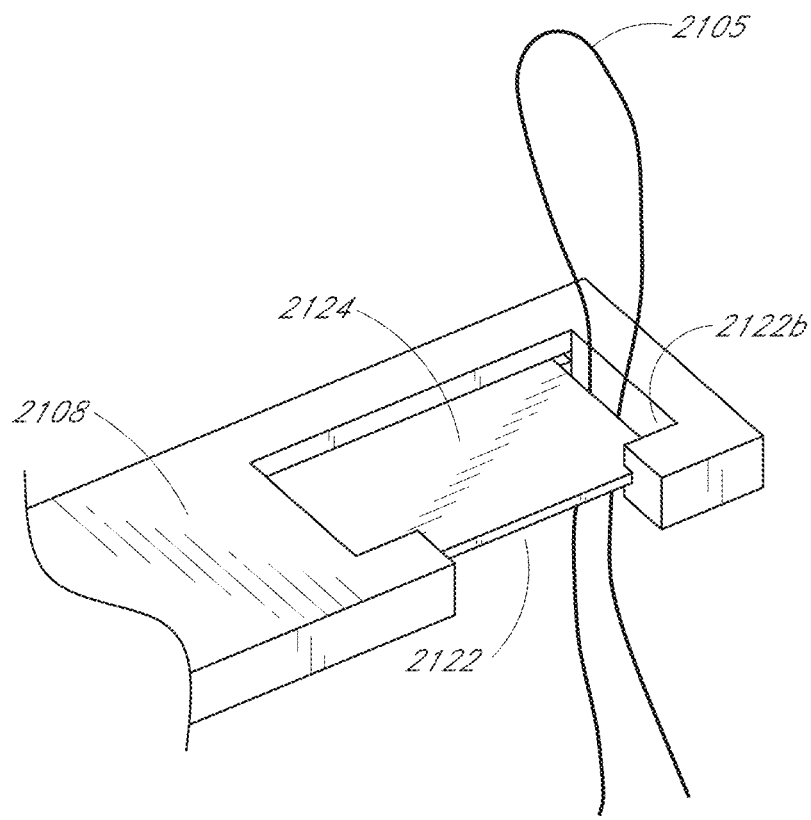

In another embodiment of a suture-receiving element 2108, FIGS. 21A-21B illustrate a suture-receiving element 2108 or snare with a C-shaped frame. In this embodiment, the suture-receiving element 2108 comprises a capture area 2122, though this configuration of a C-shaped frame reduces the need for a complete circumscribed window 2122. A movable panel 2124 or ribbon slides back and forth against an end 2122b of the window 2122. When a suture 2105 passes through the window 2122, the ribbon 2124 may slide against the end 2122 of the window 2122 to capture the suture 2105, as illustrated in FIG. 21B.

The methods of capturing the suture are not limited to the above-mentioned embodiments, as the suture-passing element may even be retracted from the suture-receiving element before the suture-receiving element is closed.

Figure 22A:
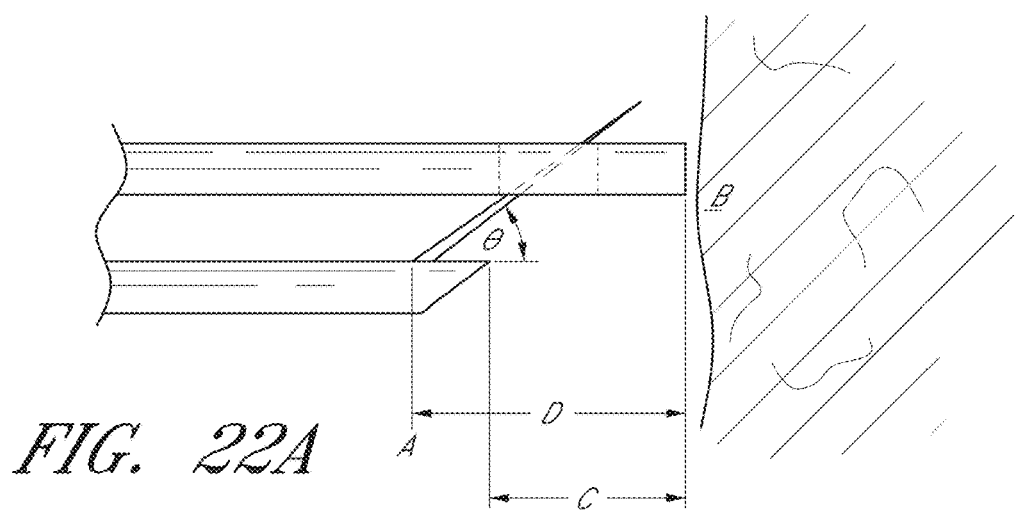
FIG. 22A illustrates a suture passer system for treating meniscal tissue.

In FIG. 22A, a design of a two-shaft embodiment of a suture passer system, that has been used, e.g., for meniscal repair, is shown. In general, conventional two-shafted suture passer systems comprise a needle shaft and a capture shaft. A distal tip of the capture shaft penetrates further into tissues than a distal tip of the needle shaft. The difference in depth between the distal tip of the needle shaft to the distal tip of the capture shaft is defined as distance (C). When a needle is deployed from the needle shaft, the needle crosses an intended bite at an acute angle, defined as angle θ. This relatively small angle θ results in the capture shaft penetrating further into tissues than the needle shaft. Moreover, the suture passer system defines a proximal point (A) of the suture, where the suture needle emerges from the shaft, and also a depth of penetration into the tissue (B). The distance between the proximal point (A) of the suture and the depth of penetration (B) is defined as a distance (D). The small angle θ also results in a large distance (D).

Figure 22B:
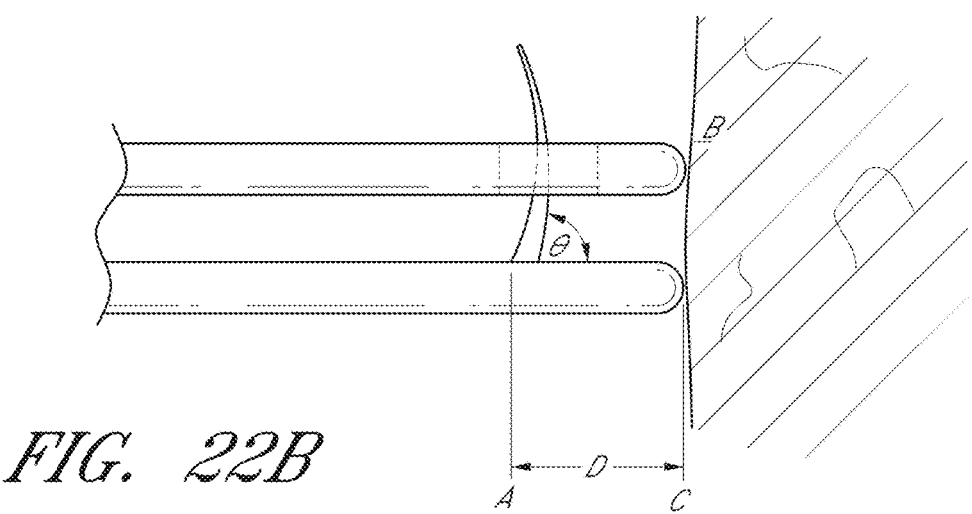
FIGS. 22B-22C illustrate an embodiment of a suture passer system for tongue suspension.
Figure 22C:
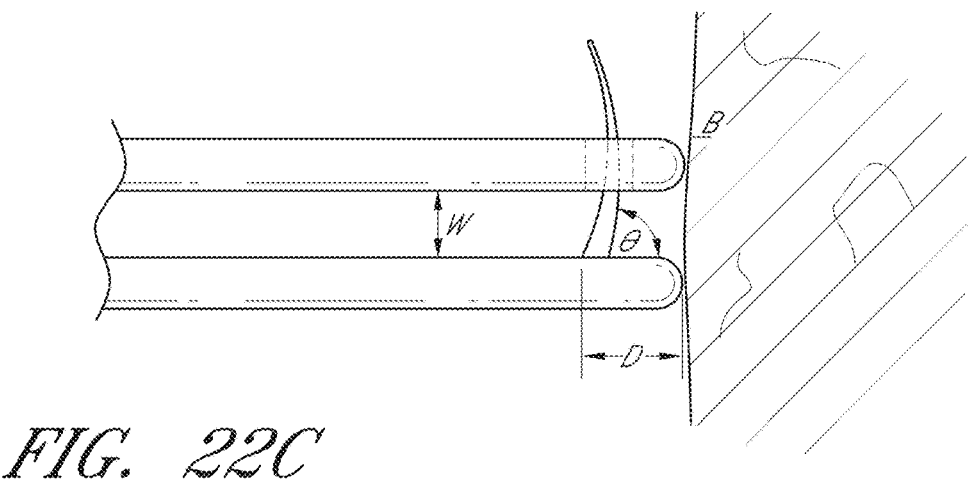

FIGS. 22B-22C illustrate a two-shaft embodiment of a suture passer system where θ approaches 90°, for example within about 20°, 15°, 10°, 5°, or less of 90°. In this embodiment, the differential distance (C) between the distal tip of the needle shaft and the distal tip of the capture shaft approaches zero, and can be less than about 10%, 7%, 5%, 3%, 2%, 1%, or even less of the length of either the suture passing shaft or the suture receiving shaft. Furthermore, the distance (D) is minimized as the proximal point (A) of the suture is minimized. The final suture loop settles in at a depth defined by proximal point (A) of the suture. For the purpose of tongue suspension, this embodiment is advantageous when it is highly desirable to place the suture as close as possible or even within the mucosal layer. However, certain meniscal devices, such as that illustrated in FIG. 22A, may not be well suited for such an application because they are configured to pass the suture to within a much larger distance (D). This distance (D) becomes very substantial and thus potentially impractical when scaled up to the bite widths required for tongue suspension (e.g, as wide as from about 3 cm to about 5 cm for tongue applications).

FIG. 22C also shows the two-shaft embodiment of the suture passer system having a width (W) between the two shafts. The width (W) defines the bite width. This embodiment advantageously allows for the suture to remain close or within the mucosal layer even for a large bite width (W). Even as the bite width increases, (D) is basically unchanged. Design optimization of this embodiment may be defined as a ratio between (D)/(W). In some embodiments, the ratio (D)/(W) is less than or equal to 0.5. In other embodiments, the ratio (D)/(W) is less than or equal to 0.35. Finally, other embodiments have a ratio (D)/(W) that is less than or equal to 0.20.

Figure 23C:
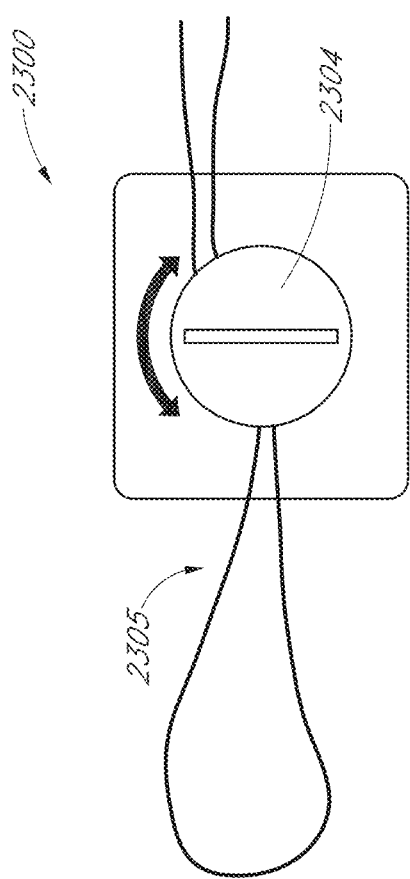
FIG. 23C illustrates another embodiment of a method of locking or tensioning a suture loop.

FIG. 23A illustrates an overall embodiment of a suture locking and tensioning mechanism 2300. The suture locking and tensioning mechanism 2300 reduces the effect of the suture 2305 slipping through, for example, a bone anchor 2301, and also allows for titration of tension. The suture locking and tensioning mechanism 2300 may be secured along the free ends of the suture 2305. In addition, the suture locking and tensioning mechanism 2300 may take on any of the configurations described below in FIGS. 23B-23F. The embodiments described below provide adjustable tensioning to a pre-existing suture loop. Therefore, it is possible to control with specificity in some embodiments anterior advancement in tongue suspension.

In FIG. 23B, an embodiment of a suture locking and tensioning mechanism 2300 comprises a cam locking mechanism 2302. The cam locking mechanism 2302 further comprises a pivot 2303 which defines an open/free state and a closed/locked state. When the pivot 2303 opens the cam locking mechanism 2302 to the open/free state, the suture 2305 may pass through the cam locking mechanism 2302. When the pivot 2303 closes the cam locking mechanism 2302 to the closed/locked state, the cam locking mechanism 2302 creates sufficient friction to lock the suture 2305 in place.

In FIG. 23C, another embodiment of a suture locking and tensioning mechanism 2300 comprises a spooling mechanism 2304. As the suture 2305 passes through the spooling mechanism 2304, the spooling mechanism 2304 may be turned clockwise or counterclockwise to spool the suture 2305 in and out of the spooling mechanism 2304.

Figure 23D:
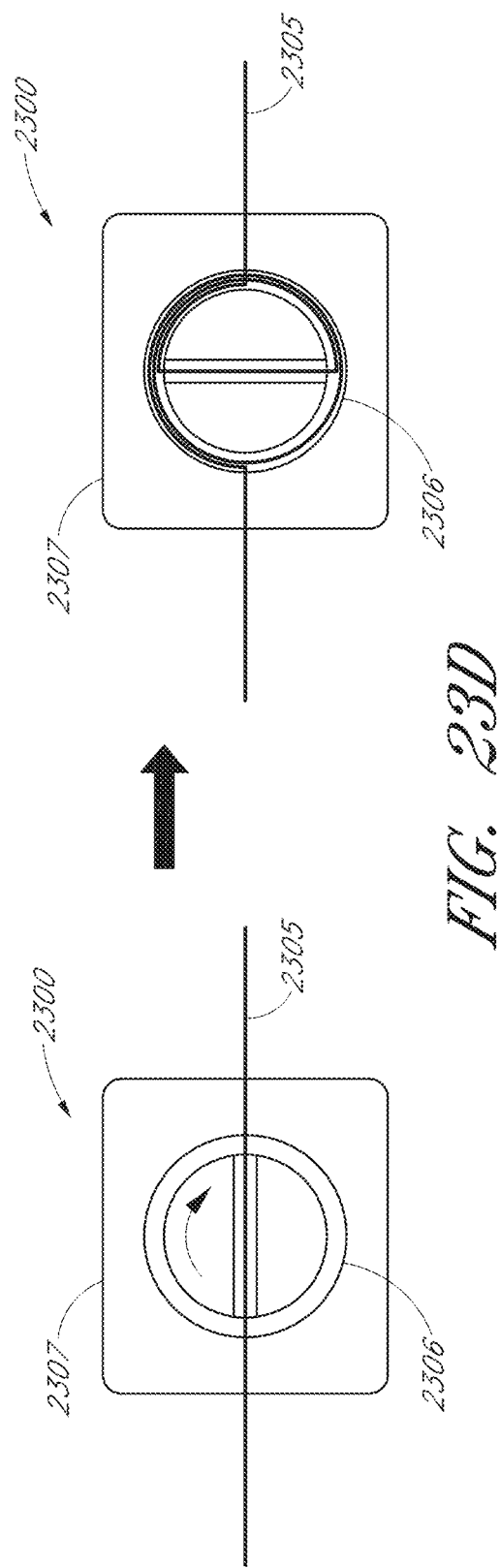
FIG. 23D illustrates another embodiment of a method of locking or tensioning a suture loop.

In FIG. 23D, another embodiment of a suture locking and tensioning mechanism 2300 comprises a rotating accessory 2306 or core configured to spool the suture 2305. The rotating core 2306 is positioned within a housing 2307 and is configured to snap in-line onto the suture 2305. As the core 2306 rotates in, for example, a clockwise direction, the suture 2305 is spooled around the core 2306. The amount of rotation may be manually controlled or automatically set with a spring.

Figure 23E:
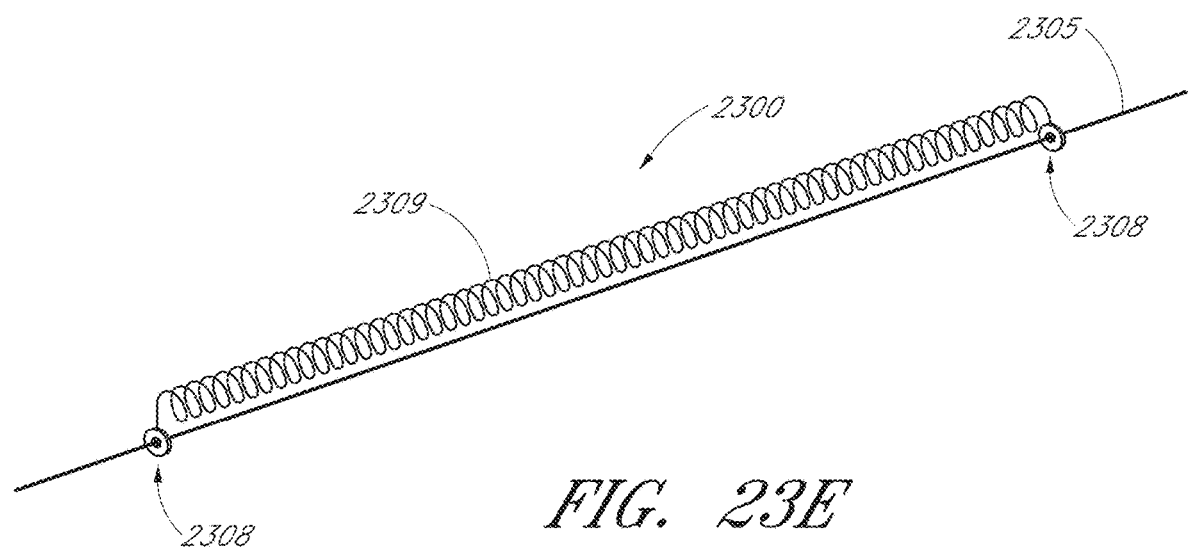
FIG. 23E illustrates another embodiment of a method of locking or tensioning a suture loop.

In FIG. 23E, another embodiment of a suture locking and tensioning mechanism 2300 comprises two or more anchors 2308 and a spring 2309. The suture 2305 passes through anchors 2308, and a spring 2309 connects between the anchors 2308. As the spring increases or decreases the distance between the anchors 2308, the anchors 2308 add or release more tension in the suture 2305 accordingly.

Figure 23F:
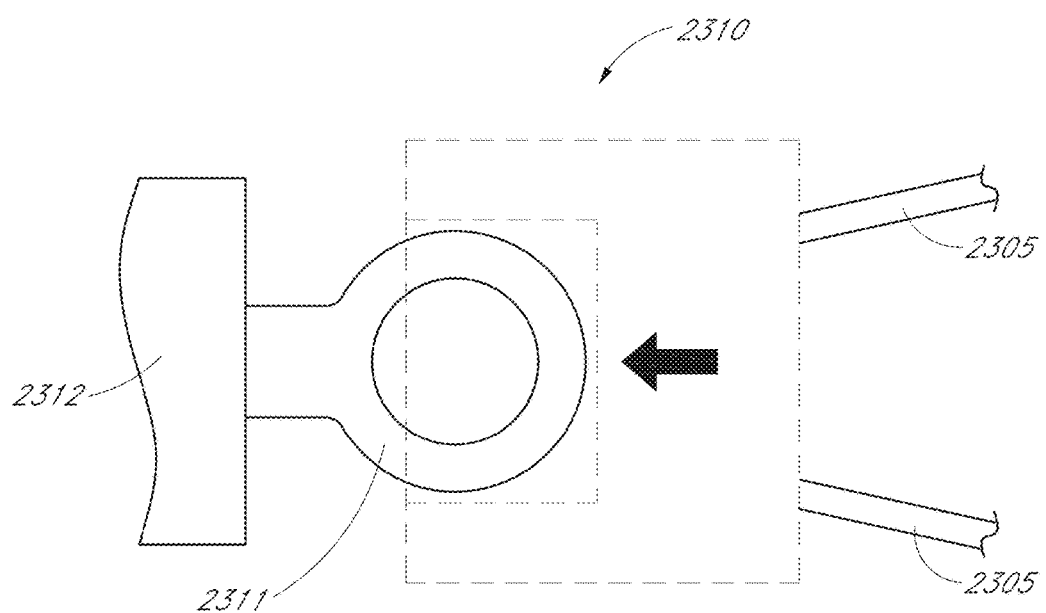
FIG. 23F illustrates another embodiment of a method of locking or tensioning a suture loop.

FIG. 23F illustrates another overall embodiment of a suture locking and tensioning mechanism 2310. As shown in FIG. 23F, the suture locking and tensioning mechanism 2310 may slide over an eyelet 2311 of a bone anchor 2312. During tension adjustment, it is important to ensure the suture locking and tensioning mechanism 2310 also provides fixation. Therefore, the suture locking and tensioning mechanism 2310 may be designed to interface with a bone anchor 2312 by sliding over the eyelet 2311.

Figure 24A:
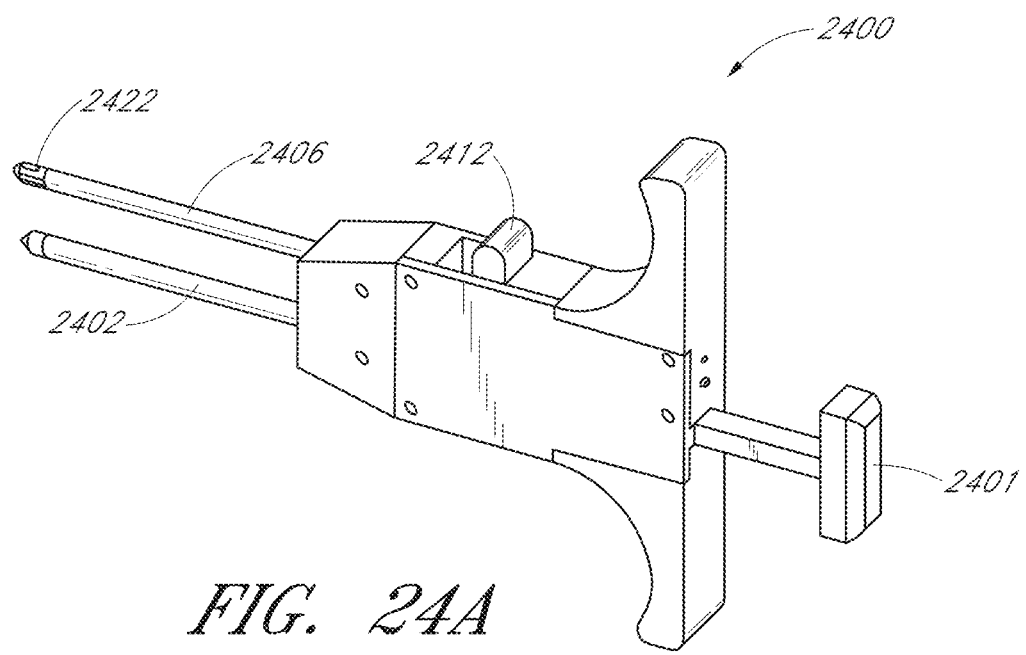
FIG. 24A illustrates a perspective view of one embodiment of a suture passer system.
Figure 24B:
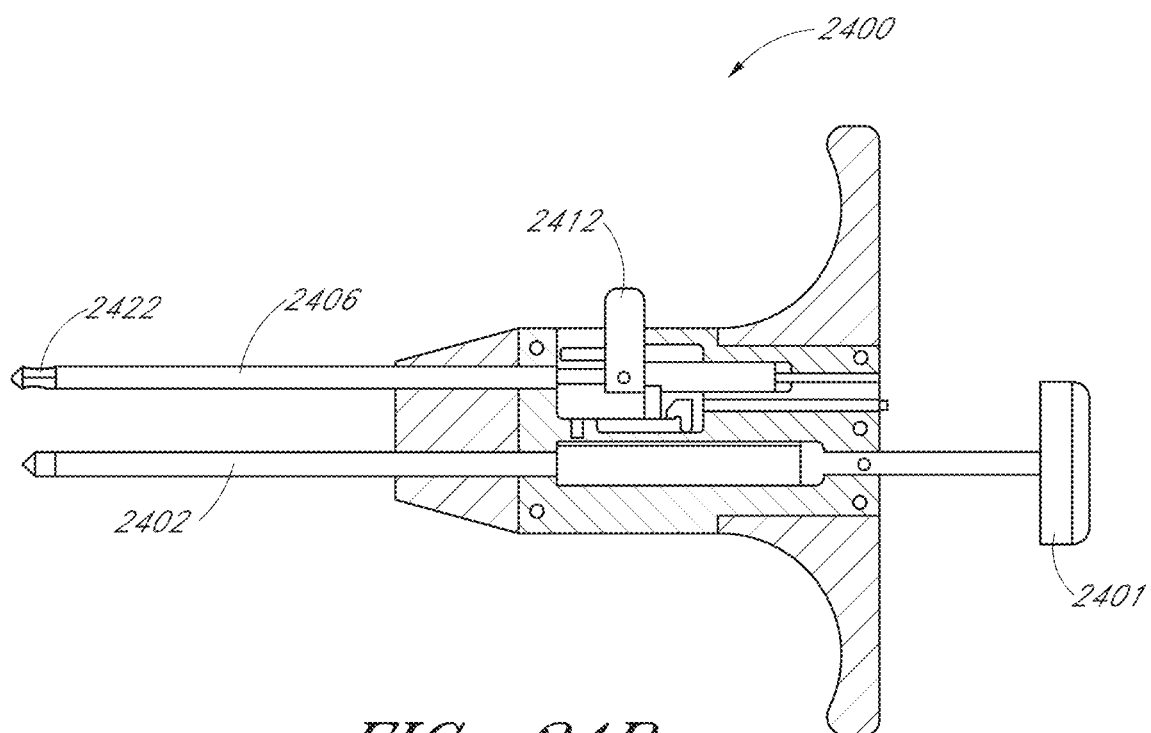
FIG. 24B illustrates a cross-sectional view of the suture passer system in FIG. 24A.

FIG. 24A illustrates an embodiment of a suture passer system 2400 having a dual-shaft configuration with a first elongate shaft 2402 and a second elongate shaft 2406 that may have some elements that are as described in connection with FIGS. 5G-5I above. FIG. 24B illustrates the suture passer system 2400 in cross-sectional view illustrating additional mechanics and controls of the system 2400. The illustrated suture passer 2400, unlike the embodiment illustrated in FIGS. 5G-5I, has a single actuator control 2401 for actuating both the suture needle (not shown) and the retrieval element 2422 at the same time, rather than separate actuators deploying the suture needle and the retrieval element 2422, e.g., the capture window. The capture window 2422 closes when actuator 2401 moves proximally and trips a pin or other element in the path of the actuator control lumen, closing the window 2422. Window 2422 can be later reset to an open position using a separate control 2412.

With this embodiment and other embodiments described earlier, the suture passer system 2400 may be configured to provide automatic depth control. Generally, with bulky shafts, it can be challenging in certain clinical situations to determine if the distal tips of the first and second elongate shafts 2402, 2406 are truly at a desired depth, or if they have merely compressed tissues during insertion. In some embodiments of a method of automatically detecting depth control, a blunt, thin, but stiff guidewire may be inserted into the muscle and back to the mucosa. The suture passer system 2400 may be delivered over the guidewire or use a depth reading from the shaft of the guidewire to determine the desired depth to penetrate. Alternatively, a suture pass may be automatically triggered when high resistance at the distal tips of the shafts are encountered and they contact the mucosal layer. In some embodiments, the suture passer system 2400 includes one, two, or more force or resistance sensors configured to determine whether a portion, such as a distal tip of the system, has passed from a first tissue into a second tissue. In other embodiments, other elements that can be used to help determine position of the device while being deployed, such as an ultrasonic tip, fiberoptic camera, or the like could also be incorporated.

Figure 25A:
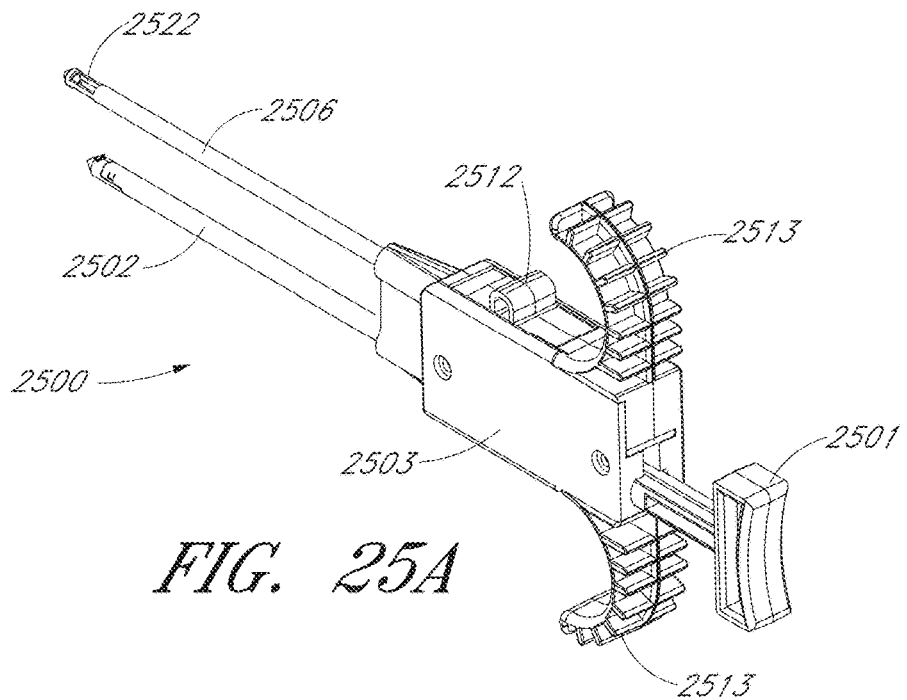
FIG. 25A illustrates a perspective view of another embodiment of a suture passer system.
Figure 25B:
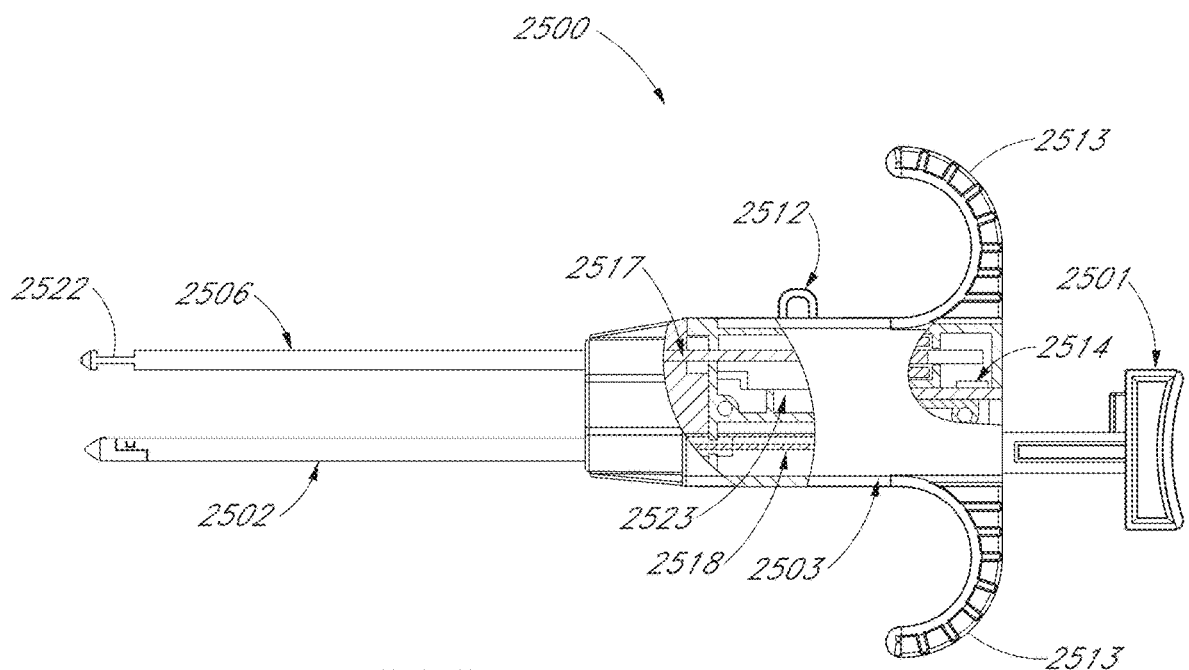
FIG. 25B illustrates a cross-sectional view of the suture passer system in FIG. 25A.

FIG. 25A illustrates another embodiment of a suture passer system 2500 having a dual-shaft configuration, similar to that shown in FIGS. 24A-24B. FIG. 25B illustrates the suture passer system 2500 of FIG. 25A in partial cross-sectional view showing additional mechanics and controls of the system 2500. The suture passer system 2500 includes a single actuator control 2501 at a proximal end for a user to actuate both the suture needle (not shown) within the first elongate shaft 2502 and the retrieval element 2522 (e.g., capture window) within or operably connected to the second elongate shaft 2506 at the same time, specifically via a needle pushrod 2518 and the actuator control 2501. The suture passer system 2500 further includes a handle or body 2503 housing the different mechanical components of the system 2500. The suture passer system 2500 also includes finger grips 2513 extending from opposite sidewalls of the body 2503. The finger grips 2513 can be arcuate in shape to facilitate ease of gripping near the proximal end of the suture passer system 2500.

Among the different mechanical components in the suture passer system 2500, there is also a secondary control 2512 along one of the sidewalls of the body 2503 to reset the capture window 2522 to an open position by actuation of a window release spring 2523 as described above in connection with FIGS. 24A-B. Capture window rod 2517 is axially movable within a lumen of the second elongate shaft 2506 to facilitate opening and closing of the capture window; corresponding needle pushrod 2518 is axially movable within a lumen of the first elongate shaft 2502. Both can be actuated in concert by the single actuator control 2501 as previously noted. When the actuator control 2501 is actuated, the needle exits the first elongate shaft 2502 toward the capture window 2522 of the second elongate shaft 2506. The needle moves into the window 2522 and the capture window 2522 closes when actuator 2501 moves distally and trips trigger 2514 in the path of the actuator control 2501, releasing the window release spring 2523 and closing the window by allowing the capture window rod 2517 to move distally under spring force (spring not shown). Secondary control 2513, which is connected to capture window rod 2517, is used to reset the capture window in an open position by moving it from a distal activated position to a proximal set position, which in turn moves the capture window rod 2517 into a proximal position which opens the capture window. Window release spring 2523 locks the secondary control 2512 in a proximal position against a coaxial bias spring force provided by a capture window spring (not shown).

A first elongate shaft 2502 and a second elongate shaft 2506 extend distally from the body 2503. In some embodiments, the first elongate shaft 2502 may extend about 3 inches to about 3.5 inches distally from the body 2503 of the device in its fully extended configuration, such as about 3.16 inches, and the second elongate shaft 2506 may extend about 3.1 inches to about 3.6 inches distally from the body of the device in its fully extended configuration, such as about 3.27 inches. The distance between the distal end of the first elongate shaft 2502 and the distal end of the second elongate shaft 2506 may be about 0.1 inches to about 0.6 inches. Regarding the body 2503 of the suture passer system 2500, the length of the body 2503 may be about 2.56 inches. The thickness of the body 2503 may be about 0.54 inches, and the height of the body 2503, including the curved, teethed flanges, may be about 3.25 inches. Other dimensions of the suture passer system 2500 can vary according to the desired design and performance. In addition, the suture passer system 2500 may include the same features described previously in the suture passer system 2400. FIGS. 25C and 25D represent rotated side views, and FIG. 25E is a view of the proximal end of the suture passer system 2500, with one non-limiting example of various dimensions of the device.

Figure 26A:
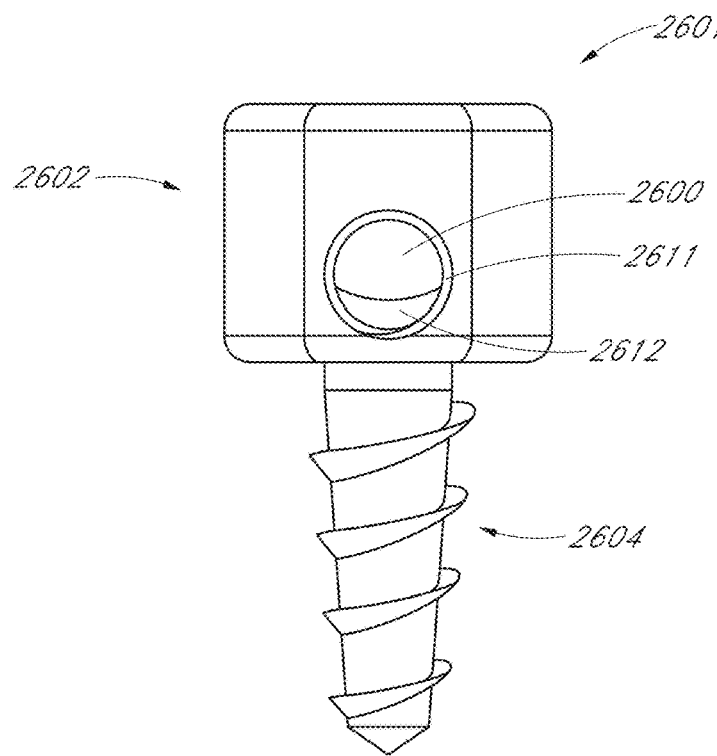
FIG. 26A illustrates an embodiment of a bone anchor with a suture locking and tension mechanism.
Figure 26B:
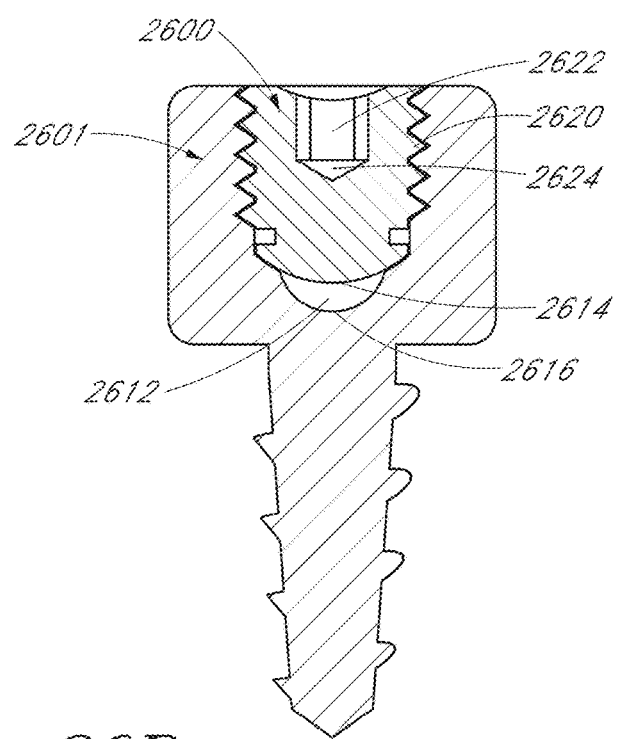
FIG. 26B illustrates a cross-sectional view of the bone anchor in FIG. 26A with a gap between the suture locking and tension mechanism and the bone anchor.

FIGS. 26A and 26B illustrate a bone anchor 2601 with a proximal head portion 2602 and a distal threaded portion 2604. The bone anchor 2601 has a suture locking and tension mechanism 2600 (e.g., locking screw) within an eyelet 2611 of the bone anchor 2601. The eyelet 2611 can extend completely through two sides of the proximal head portion 2602 of the bone anchor and have a longitudinal axis that is transverse to the longitudinal axis of the bone anchor 2601. In some embodiments, the locking screw 2600 has an enlarged proximal head portion 2622 having an opening on its upper surface, e.g., a hex configuration that may be used to engage a screwdriver or other instrument. The locking screw 2600 has a drive portion 2624 configured to rotate and threadably engage an internally threaded surface 2620 extending from the upper surface of the proximal head portion 2602 and in communication with the eyelet 2611. Appropriate rotation of the locking screw 2600 with respect to the internally threaded surface 2620 will decrease the available space within the eyelet 2611 such that a suture is reversibly trapped within the eyelet 2611 by the locking screw 2600. The eyelet 2611 defines a cavity within the bone anchor 2601 that the locking and tension mechanism 2600 may not entirely fill. Rather, between a distal surface 2614 of the locking and tension mechanism 2600 and a distal surface 2616 of the eyelet 2611 defines a gap 2612. The gap 2612 is sufficiently small that the suture remains fixed within the eyelet 2611 while the locking screw 2600 is appropriately secured within the eyelet 2611 (e.g., via complementary threaded surfaces of the locking screw 2600 and eyelet 2611 as noted above), however, the gap 2612 advantageously helps to minimize damage to the suture (not shown). In other words, the height (a distance measured parallel to the longitudinal axis of the bone anchor 2601) of the gap 2612 should be sized and configured to adequately secure the suture while avoiding over-compression of the locking and tension mechanism 2600 to the suture. In one embodiment, the gap 2612 or height dimension is between about 0.005 inches and 0.02 inches, such as about 0.01 inches. When the height of the gap is configured to adequately secure the suture without over-compressing, a desired minimum pull-out force for the suture can be in some embodiments about 4 kgf to about 8 kgf, or more preferably about 5 kgf to about 7 kgf, or at least about 4 kgf, 5 kgf, 6 kgf, 7 kgf, 8 kgf, or more in some embodiments.

FIGS. 27A-27B illustrate a suture adjustment tool 2700 for controllably pulling a suture 2705 through a bone anchor 2701 to provide more precise tongue advancement. As described elsewhere herein, one or more sutures 2705 may form a suture loop (not shown) via use of a suture passer within the tissue (e.g., tongue). The tongue may be suspended by securing the free ends of the suture loop through a structure such as the bone anchor 2701, which can be implanted in the mandible or hyoid bone. Typically, as the free ends of the suture loop are pulled through the bone anchor 2701, the tongue can be effectively suspended or advanced in the anterior-posterior direction.

The suture adjustment tool 2700 can provide precise control of the amount of tongue advancement as a result of pulling the one or more sutures 2705 through the bone anchor 2701. In FIG. 27A, the suture adjustment tool 2700 has a hemostat-like structure comprising a handle 2702 at a proximal end and a capture element 2703 at a distal end. In FIG. 27B, a magnified view of the capture element 2703 is provided. In some embodiments, the capture element 2703 may be conical, frusto-conical, or tubular in shape. The capture element 2703 further includes clamping jaws 2703a that actuate between an open and closed position. A user may grasp the suture adjustment tool 2700 at the handle 2702 to actuate between the open and closed position. In addition, the capture element 2703 includes a groove 2703b circumscribed around the capture element 2703. The groove 2703b has a predetermined circumference such that when the groove 2703b is rotated about the longitudinal axis of the capture element 2703 in an appropriate direction, the suture 2705 spools around the groove 2703b or releases from the groove 2703b to either increase or decrease tension depending on the desired clinical result.

In connection with FIGS. 27A and 27B, the user may grasp the suture adjustment tool 2700 at the handle 2702 and position the capture element 2703 over the sutures 2705. The user may actuate the clamping jaws 2703a of the capture element 2703 to the open position, and then secure the sutures 2705 by actuating the clamping jaws 2703a to the closed position. While in the closed position, the user may rotate the suture adjustment tool 2700 about the longitudinal axis of the capture element 2703. In one embodiment, as the user rotates the tool 2700 toward the bone anchor 2701, e.g., clockwise in FIG. 27B, the sutures 2705 spools around groove 2703b. As the user rotates the tool 2700 away from the bone anchor 2701, e.g., counterclockwise in FIG. 27B, the sutures 2705 release from the groove 2703b. In one embodiment, the groove 2703b has a circumference of about 1 cm, so that a full revolution pulls in or releases out about 1 cm in length of the suture 2705. Following adjustment to a desired tension, the suture 2705 can be locked with respect to the bone anchor 2701 as described elsewhere herein and the suture 270 released from the adjustment tool 2700.

Figure 28A:
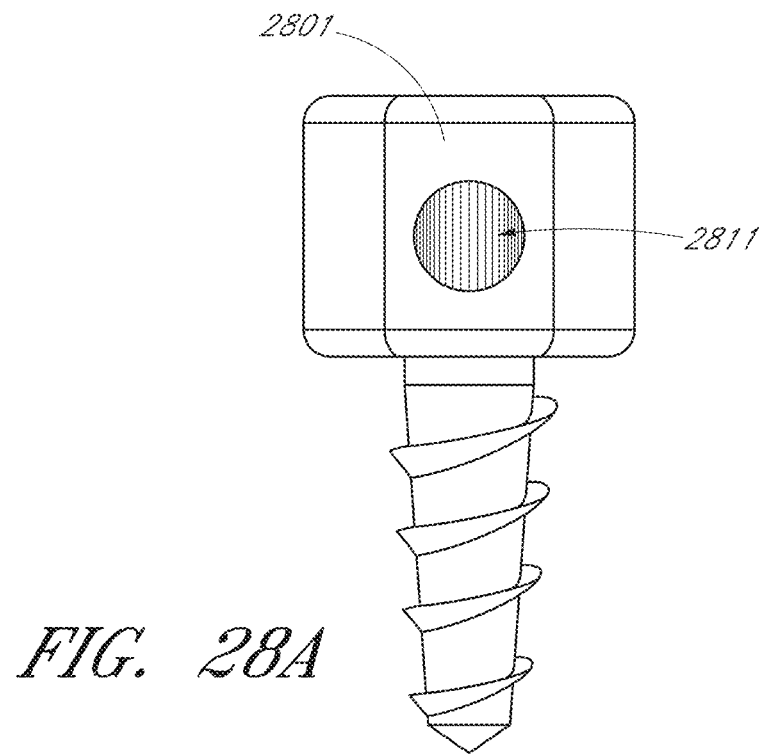
FIG. 28A illustrates an embodiment of a bone anchor having a rotatable inner shaft with engaging structures configured to engage one or more sutures.
Figure 28B:
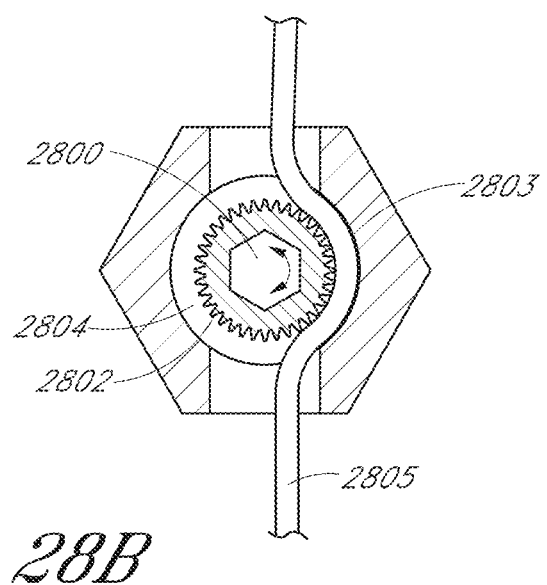
FIG. 28B illustrates a cross-sectional top view of the bone anchor of FIG. 28A.

FIGS. 28A and 28B illustrate an embodiment of a bone anchor 2801 having a rotatable inner shaft 2800 with engaging structures 2802 (e.g., teeth) configured to engage one or more sutures 2805. As disclosed elsewhere herein, the suture 2805 may be secured at one or both ends to a structure such as the bone anchor 2801. As illustrated in FIG. 28B, an inner shaft 2800 and an inner wall 2803 of the bone anchor 2801 define a cavity 2804 therebetween which is sized and configured to house the suture 2805. The suture 2805 may pass through an eyelet 2811 and through the cavity 2804, so that the suture 2805 can be secured between the inner shaft 2800 and the inner wall 2803.

In some embodiments, the inner shaft 2800 may further comprise a plurality of teeth 2802 around the shaft 2800 and configured to engage the suture 2805. The teeth 2802 may protrude radially outwardly from the inner shaft 2800 to directly contact the suture 2805. The inner shaft 2800 may further be configured to rotate about its longitudinal axis to cause the suture 2805 to slide in and out of the bone anchor 2801. In some embodiments, the teeth 2802 have a fixed pitch so that rotation of the inner shaft 2800 (referred to herein as a "tractor drive") moves the suture 2805 by a fixed amount. As a result, the "tractor drive" can provide precise control as well as advancement of the suture 2805, which can effectively suspend or advance the tongue in the anterior-posterior direction.

FIGS. 29A-29C illustrate an embodiment of a bone anchor 2901 having a first eyelet 2911 as well as at least a second eyelet 2900 extending radially outwardly from one or more of the sides of the bone anchor 2901. In the illustrated embodiment, the first eyelet 2911 may be positioned on bone anchor 2901 as described with respect to FIGS. 26A-B and FIGS. 28A-B, which is discussed earlier herein. In one embodiment as illustrated in FIGS. 29A and 29B, the second eyelet 2900 may have a central axis through the eyelet that is orthogonal to the central axis of the first eyelet 2911.

As discussed earlier herein, multiple suture loops having the same or differing orientations can provide more localized control of tissue suspension. Therefore, it may be desirable to stabilize another suture loop to the bone anchor 2901, which can be accomplished with the second eyelet 2900. In FIG. 29C, both the first suture loop 2905*a* and the second suture loop 2905*b* are secured to the bone anchor 2901 with the suture simply passing through the second eyelet 2900. This ensures that there are no compressive forces in the suture 2905, and that the advancement forces in the anterior direction are uniform. In some embodiments, a single suture line may also be tied to the second eyelet 2900, forming two suture lengths each sufficiently long for creating its own suture loop within the tongue. After looping through the tongue, the free end of these suture lengths would be secured in the first eyelet 2911 of the bone anchor 2901. This use of the second eyelet 2900 also ensures that there are no compressive forces in the suture, and that the advancement forces of each loop can be independently adjusted. In other embodiments, additional eyelets, such as a third, fourth, or more may also be present to stabilize additional suture loops, depending on the desired clinical result.

FIG. 30A illustrates an embodiment of a suture 3000 having one, two, or more radiopaque markers 3002 anywhere along its length such that implantation and desired positioning can be confirmed via x-ray or fluoroscopy. In some embodiments, the radioopaque marker elements are made of a metal or a metal alloy, such as, for example, one or more of nitinol, Elgiloy®, Phynox®, MP35N, stainless steel, nickel, titanium, gold, rhenium, tungsten, palladium, rhodium, tantalum, silver, ruthenium, and hafnium. The marker element could be a 90% platinum and 10% iridium alloy in one particular embodiment. The suture 3000 can also include a portion 3004 that is shaped into a relatively flattened configuration similar to that of a ribbon, such that it has, for example, a first dimension such as a width that is at least about 25%, 50%, 100%, 200%, 300%, 400%, 500% or more greater than a second dimension such as a height. In some embodiments, the suture 3000 can be flattened by compression. The suture 3000 can be made of a polymer material, e.g., polypropylene, that is amenable to flattening without substantial fraying. Also, the suture 3000 can be made from a monofilament suture or braided out of a multifilament suture. The suture 3000 may also include a non-flattened portion 3006 that has a width and height that are substantially the same, or the entire suture 3000 may be in the flattened configuration. FIG. 30B illustrates a suture 3000 with a flattened section 3004 but without radiopaque markers 3002. The suture 3000 may in one embodiment be a suture initially placed by any of the suture passers described herein. In another embodiment, the suture 3000 may be a second suture delivered into tissue, such as tongue tissue, using a guide suture placed by a suture passer, as described previously. The size, shape, and material of the second suture can add strength and greater tension so as to provide additional tissue control. Additionally, the size, shape, and material of the second suture can be configured in a fashion to avoid fraying, tearing, or stretching For example, the second suture may have a width greater than 25%, 50%, 80%, 90%, 100%, 200%, 400% or greater than the width of the first suture.

Figure 31A:
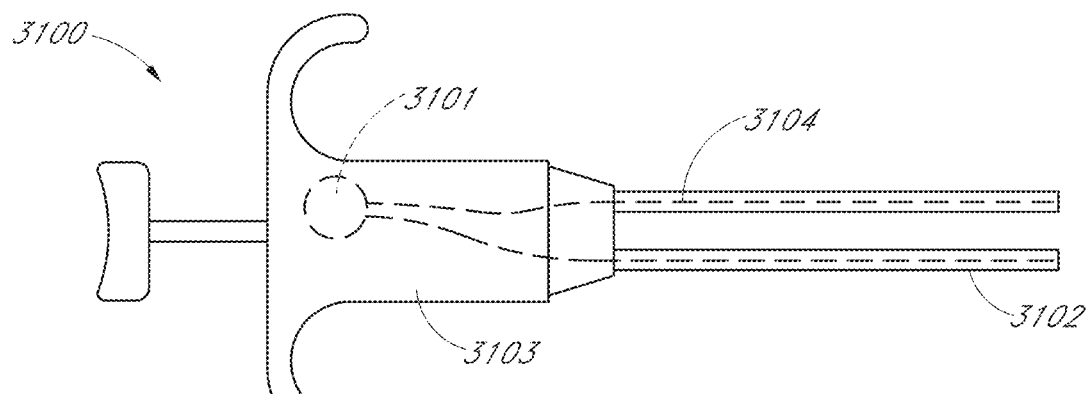
FIGS. 31A-31B illustrate an embodiment of a suture passer system with a light source to provide illumination at the mucosal layer.
Figure 31B:
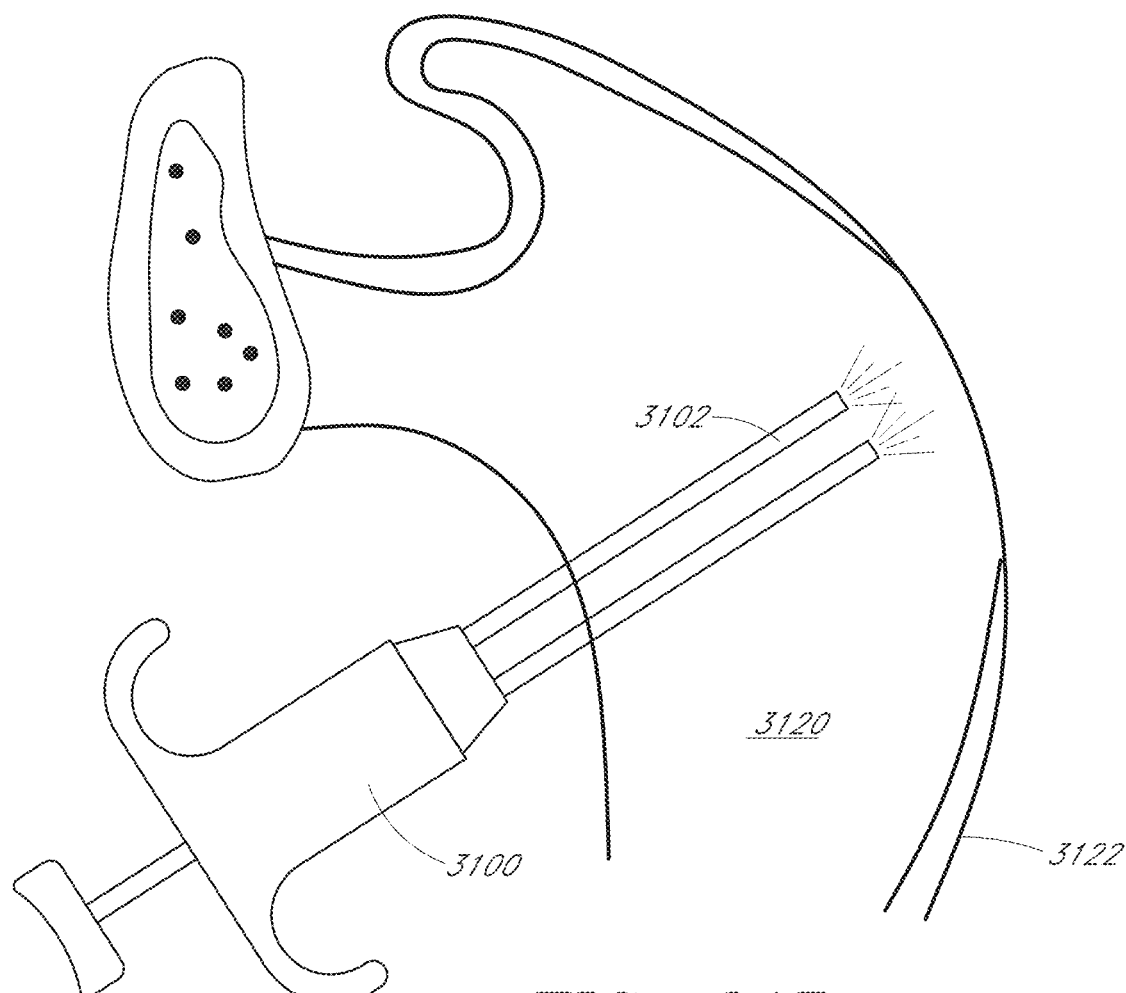

With reference to FIGS. 31A-31B, an embodiment of a suture passer system 3100 may be configured to carry one, two, or more light sources 3101 to help identify the location and depth of the distal tips 3102 of the suture passer 3100 within the tongue 3120 or other tissue before performing a suture pass or other procedural step. The suture passer 3100 may include the light source(s) 3101 in or attached to the body 3103 or within a lumen of or attached to the distal tips 3102. The light source 3101 may include an LCD, LED, incandescent, fluorescent, laser or any other visible, ultraviolet, or infrared light source for example, or a combination of the above. The light source 3101 may be turned on and off via, for example, a control on the body 3103 of the suture passer 3100. In FIG. 31A, the body 3103 contains the light source 3101, and a self-contained power source, such as a battery, or an external power conduit extending proximally toward the operator and connected to power source remote to the suture passer 3100. Other positioning elements that may assist with location, depth, or orientation of the device when within the body such as an accelerometer, gyroscope, or another sensing element may also be included In some embodiments where the light source 3101 is not contained within the distal tips 3102 of the suture passer 3100, the body 3103 may further contain fiber optics 3104 or other light guide pathways from the light source 3101 extending through the distal tips 3102 so as to direct light therethrough.

In FIG. 31B, the suture passer 3100 is shown with distal tips 3102 inside the tongue 3120 and illuminating mucosal layer 3122. As the distal tips 3102 approaches the mucosal layer 3122, light will begin to penetrate through the mucosal layer 3122 to provide visible transillumination through the mucosal layer 3122. In some embodiments, light can be visible to an operator directly observing the external surface of the tongue when the distal tips 3102 are within approximately 0.6 cm, 0.5 cm, 0.4 cm, 0.3 cm, or less of the mucosal layer 3122 of the tongue 3120. Without using fluoroscopy or x-ray modalities that involve radiation or additional equipment, the degree of light penetration through the mucosal layer 3122 can provide both depth and location of one or both of the distal tips 3102 of the suture passer 3100. Moreover, the degree of light penetration through the mucosal layer 3122 can also provide information regarding anatomical characteristics of the tongue 3120. For example, there may be a high degree of light penetration through the mucosal layer 3122 for a relatively flattened and thinned tongue 3120, while there may be a low degree of light penetration through the mucosal layer 3122 for a relatively extended and thickened tongue 3120.

Figure 32A:
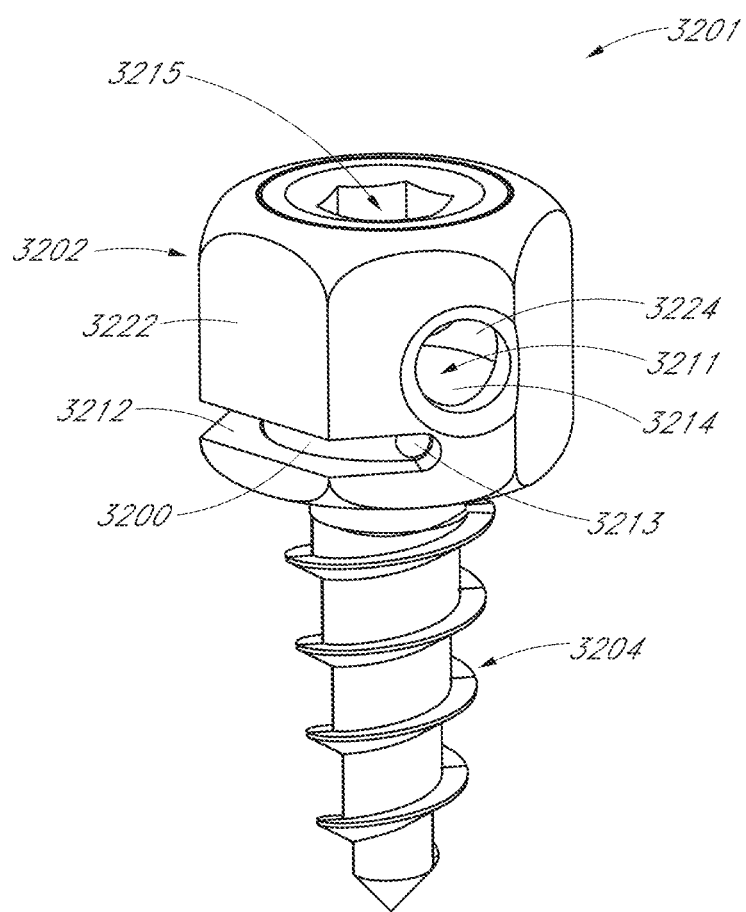
FIGS. 32A-32D illustrates an embodiment of a bone anchor with a suture locking and tensioning mechanism.

FIG. 32A illustrates a bone anchor 3201 with a suture locking and tension mechanism, e.g., cam lock 3200. The bone anchor 3201 includes a proximal head portion 3202 and a distal threaded portion 3204. In FIGS. 32A-32G, the cam lock 3200 is within the proximal head portion 3202. The proximal head portion 3202 can include a drive portion 3215 recessed in the top surface of the proximal head portion 3202 to provide torque to the cam lock 3200 by actuating the cam from a first position to a second position, such as, for example when an adjustment tool (not shown) is placed into a cavity of the drive portion 3215 and rotated in an appropriate direction. The proximal head portion 3202 may additionally include outer wall 3222 with a plurality of faces forming a polygonal shape (e.g., hexagonal). The proximal head portion 3202 may also include an aperture or eyelet 3211 configured to carry a tension element, such as a suture therethrough that can extend completely through two faces, such as opposing faces of the proximal head portion 3202, with a longitudinal axis that is transverse to, substantially transverse to, or at an angle with respect to the longitudinal axis of the bone anchor 3201. In some embodiments, the eyelet 3211 can be laterally offset from an axis of symmetry of the proximal head portion 3202, as illustrated in FIG. 32A.

In some embodiments, the cam lock 3200 is rotatable within the proximal head portion 3202. The cam lock 3200 may be a separate component from the proximal head portion 3202. A groove or pathway 3212 may be formed around a portion of the outer wall 3222 of the proximal head portion 3202. The pathway 3212 can be formed below the eyelet 3211 and circumferentially around the proximal head portion 3202 for between about, for example, 60° and about 360°, such as about 180°. In the illustrated embodiment, the pathway 3212 exposes a portion of the cam lock 3200.

Figure 32B:
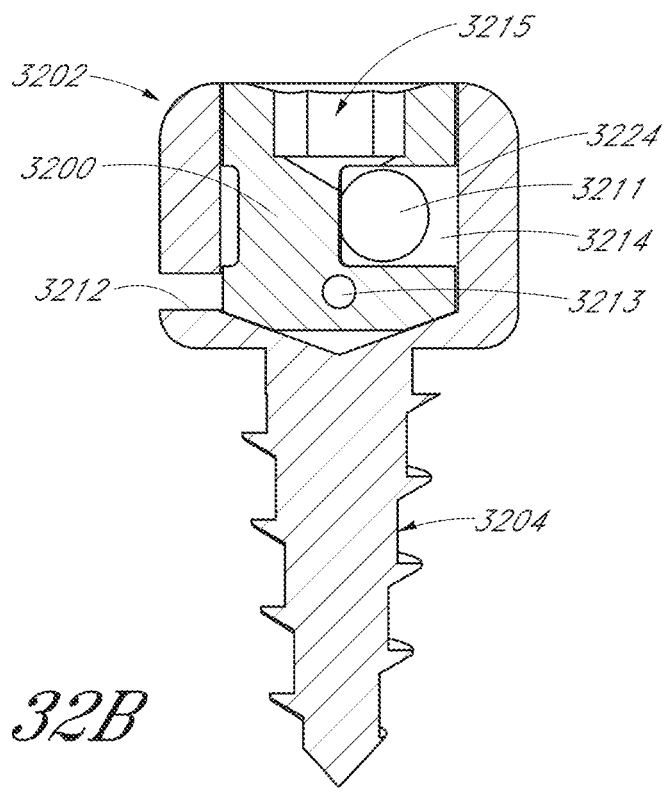
Figure 32C:
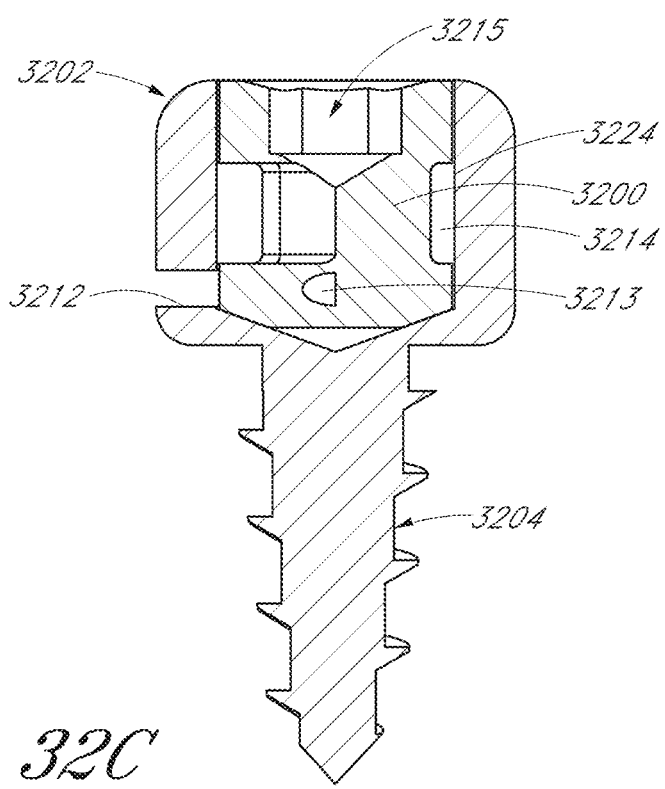

The portion of the cam lock 3200 exposed by the pathway 3212 can have a radially-outwardly extending pin, stop, or other rotation limiting member 3213 configured to limit rotation of the cam lock 3200 within the pathway 3212. Appropriate rotation of the engagement member 3215 rotates the cam lock 3200 between an open position and a closed position. FIG. 32B illustrates a cross-sectional view of the cam lock 3200 in the open position, permitting passage through the eyelet 3211. In the open position, a space 3214 within the cam lock 3200 is aligned with the eyelet 3211 so that a tension element such as a suture may thread through the bone anchor 3201 by passing through the eyelet 3211. FIG. 32C illustrates a cross-sectional view of the cam lock 3200 in the closed position. In the closed position, the space 3214 within the cam lock 3200 moves out of alignment with the eyelet 3211 so that the suture is compressed between the cam lock 3200 and an inner wall 3224 of the proximal head portion 3202, causing the suture to be reversibly trapped within the eyelet 3211. The rotation limiting member 3213 ensures that the user does not over-rotate the cam lock 3200, which thereby preserves optimal positioning. In one embodiment, appropriate rotation of the cam lock 3200 can be between about 60° and about 360° to rotate between an open and closed position, such as about 180°.

Figure 32D:
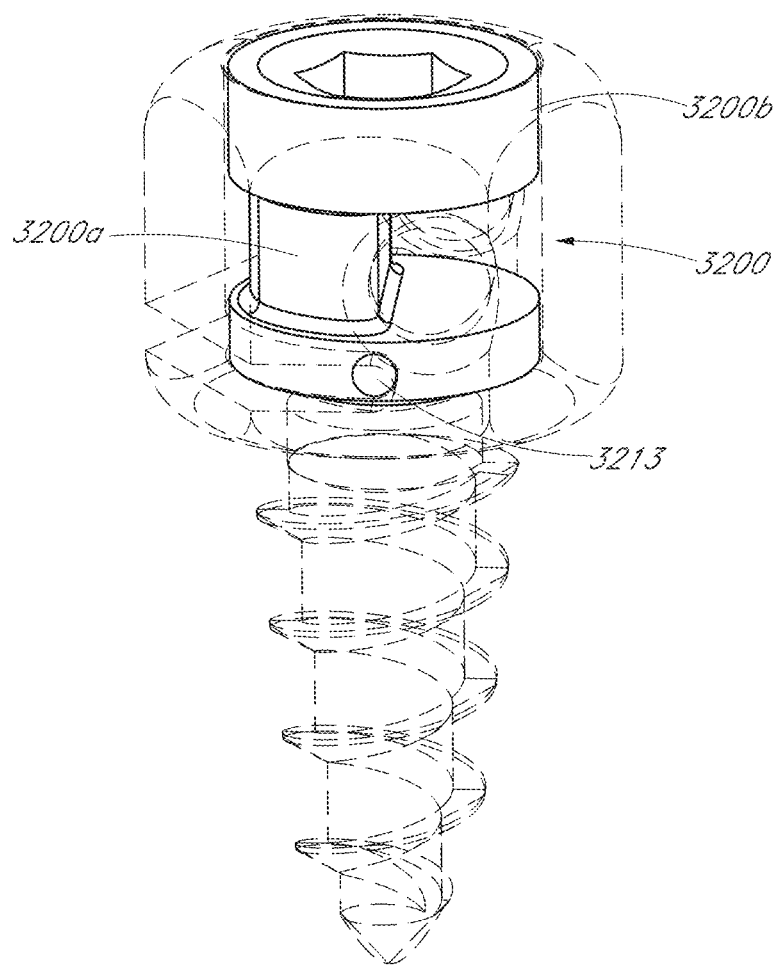

FIG. 32D illustrates an example of a cam lock 3200 configured to rotate within the proximal head portion 3202 of the bone anchor 3201 (shown in phantom). The cam lock 3200 may include a cam surface or shaft 3200a between at least two bearings 3200b. In some embodiments, the shaft 3200a may have a semi-cylindrical shape, having a contour that is substantially curved near and/or along the edges. The shaft 3200a can be radially offset from the longitudinal axis of the cam lock 3200 so that when the cam lock 3200 rotates, the shaft 3200a rotates about the longitudinal axis of the cam lock 3200.

Figure 32E:
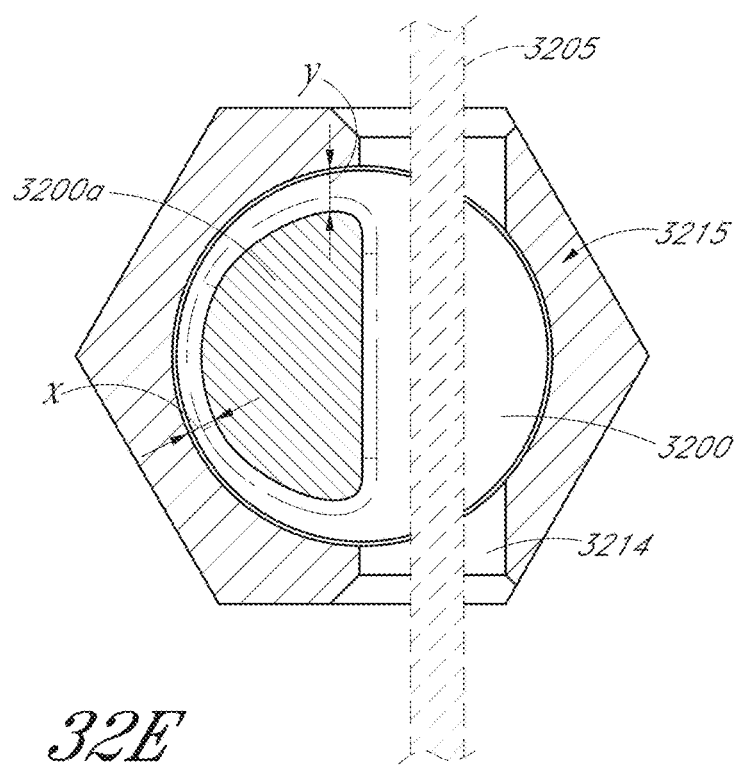
FIGS. 32E-32H illustrate a method of locking a suture using the bone anchor having the suture locking and tensioning mechanism of FIGS. 32A-32D.
Figure 32F:
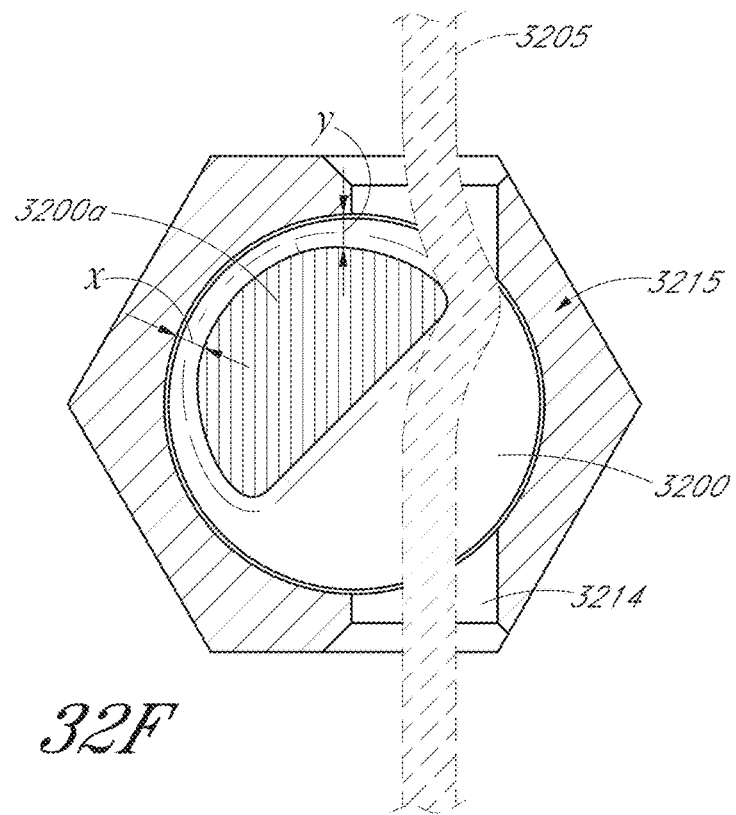
Figure 32G:
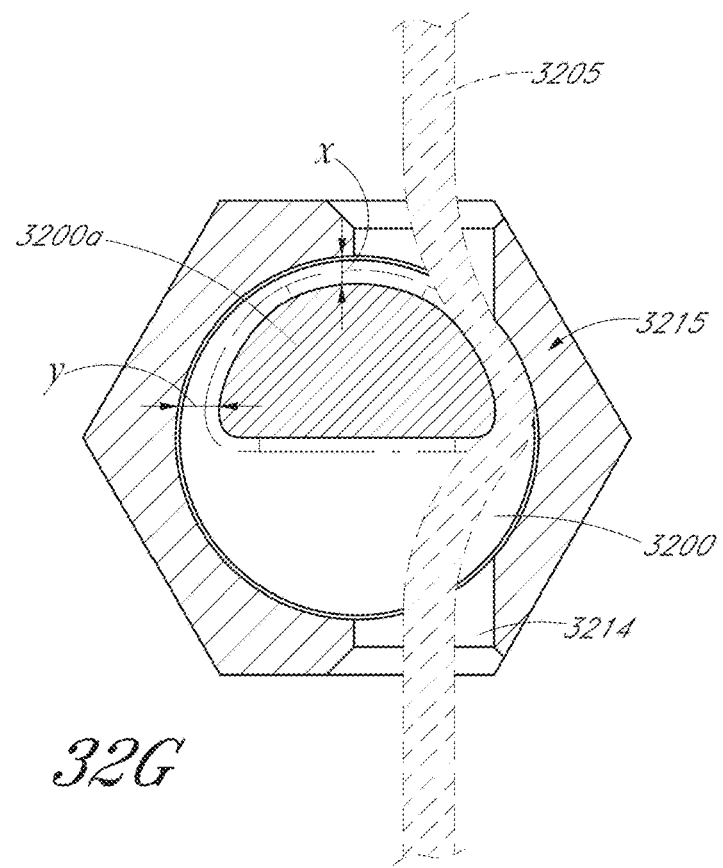
Figure 32H:
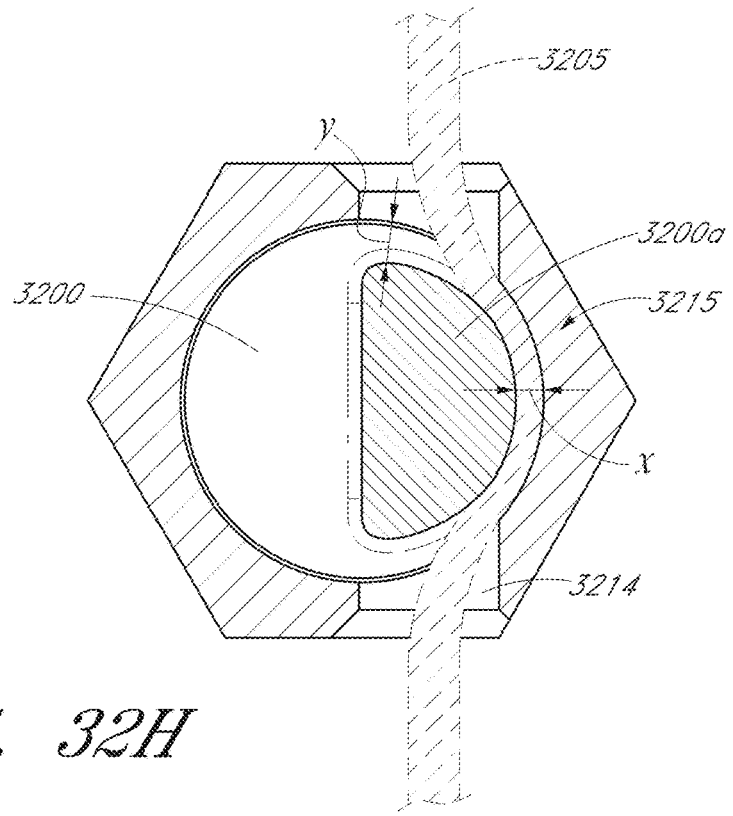

FIGS. 32E-32H illustrate a process of securing a suture 3205 within the bone anchor 3205 using the cam lock 3200. When the cam lock 3200 is in the open position, the suture 3205 passes freely through space 3214, as shown in FIG. 32E. In FIG. 32F, when the cam lock 3200 is rotated about 45° clockwise, a portion of the shaft 3200a can begin to make contact with the suture 3205. When the cam lock 3200 is rotated further, such as about 90° in some embodiments, more surface area of the shaft 3200a contacts and compresses the suture 3205, as illustrated in FIG. 32G. The amount of compression of suture 3205 can be proportional to a distance Y of the shaft 3200a to the inner wall 3224. In FIG. 32H, the cam lock 3200 is rotated by about 180°, so that even more surface area of the shaft 3200a contacts and compresses the suture 3205. Here, the amount of compression of the suture 3205 can proportional to a distance X of the shaft 3200a to the inner wall 3224, which represents the minimum gap distance for optimal compression. The gap distance X is generally less than the distance Y, such as less than about 95%, 90%, 85%, 80%, 75%, 70%, 65%, 60%, 55%, 50%, 45%, 40%, 35%, 30%, 25%, 20% or less. The minimum gap distance X is sufficiently small so that the suture 3205 remains fixed within the eyelet 3211. In the illustrated embodiment, because the eyelet 3211 is laterally offset from an axis of symmetry of the proximal head portion 3202, the configuration provides additional strength in securing suture 3205.

While this invention has been particularly shown and described with references to embodiments thereof, it will be understood by those skilled in the art that various changes in form and details may be made therein without departing from the scope of the invention. For example, additional suture passers that can be used or modified for use with the methods described herein can be found in U.S. Pat. No. 5,988,171 to Sohn et al. (such as those described and illustrated in connection with FIGS. 14 through 17"), and U.S. Pat. Pub. No. 2009/0018554 A1 to Thorne et al. (such as those described and illustrated in connection with FIGS. 1-7), both of which are hereby incorporated by reference in their entireties. For all of the embodiments described above, the steps of the methods need not be performed sequentially and the individual components of the devices may be combined permanently or be designed for removable attachment at the clinical site. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present invention herein disclosed should not be limited by the particular disclosed embodiments described above.

What is claimed is:

1. A method, comprising:
    passing a first tension element proximate to a hyoid bone and around the hyoid bone;
    coupling a bone anchor to a mandible, wherein the bone anchor comprises a locking mechanism;
    passing the first tension element through the locking mechanism of the bone anchor after passing the first tension element around the hyoid bone;
    applying tension to the first tension element to move the hyoid bone; and
    securing the locking mechanism, thereby reversibly locking the first tension element with respect to the hyoid bone and the mandible.

2. The method of claim 1, further comprising:
    releasing the locking mechanism; and adjusting the tension of the first tension element with respect to the hyoid bone after releasing the locking mechanism; and securing the locking mechanism after adjusting the tension of the first tension element.

3. The method of claim 1, wherein the bone anchor is coupled near the midline of the mandible.

4. The method of claim 1, further comprising compressing the tongue to reduce an anterior-posterior dimension of the tongue.

5. The method of claim 1, further comprising suspending the tongue.

6. The method of claim 1, further comprising increasing the size of the oral cavity.

7. The method of claim 1, further comprising utilizing a second tension element to provide tissue suspension.

8. The method of claim 1, further comprising coupling another tension element to the bone anchor.

9. The method of claim 8, wherein each tension element is independently adjusted.

10. The method of claim 1, wherein the first tension element comprises a suture.

11. A method, comprising:

passing a first suture at least partially around a hyoid bone;

attaching a bone anchor to a mandible;

after passing the first suture at least partially around the hyoid bone, suspending the hyoid bone by releasably attaching the first suture to the bone anchor, wherein the first suture can be released from, tensioned, and/or reattached to the bone anchor thereby moving the hyoid bone; and locking the first suture with respect to the bone anchor.

12. The method of claim 11, further comprising releasing the first suture from the bone anchor.

13. The method of claim 11, wherein locking the first suture with respect to the bone anchor comprises passing the first suture through a locking mechanism coupled to the bone anchor.

14. The method of claim 11, wherein the bone anchor is attached near the midline of the mandible.

15. The method of claim 11, further comprising compressing the tongue to reduce an anterior-posterior dimension of the tongue.

16. The method of claim 11, further comprising suspending the tongue.

17. The method of claim 11, further comprising increasing the size of the oral cavity.

18. The method of claim 11, further comprising utilizing a second suture to provide tissue suspension.

19. The method of claim 11, further comprising attaching another suture to the bone anchor.

20. The method of claim 19, wherein each suture is independently adjusted.

* * * * *